(12) United States Patent
Kass et al.

(10) Patent No.: US 8,299,083 B2
(45) Date of Patent: Oct. 30, 2012

(54) PDE5 INHIBITOR COMPOSITIONS AND METHODS FOR TREATING CARDIAC INDICATIONS

(75) Inventors: David Kass, Columbia, MD (US); Eiki Takimoto, Baltimore, MD (US); Hunter Champion, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 752 days.

(21) Appl. No.: 11/660,440

(22) PCT Filed: Aug. 17, 2005

(86) PCT No.: PCT/US2005/029327
§ 371 (c)(1),
(2), (4) Date: Sep. 20, 2007

(87) PCT Pub. No.: WO2006/023603
PCT Pub. Date: Mar. 2, 2006

(65) Prior Publication Data
US 2009/0062313 A1    Mar. 5, 2009

Related U.S. Application Data

(60) Provisional application No. 60/602,134, filed on Aug. 17, 2004.

(51) Int. Cl.
*A61K 31/52*    (2006.01)
*A61K 31/50*    (2006.01)
(52) U.S. Cl. .................................. 514/263.1; 514/250
(58) Field of Classification Search ............... 514/263.1, 514/250
See application file for complete search history.

(56) References Cited

U.S. PATENT DOCUMENTS

| | | | |
|---|---|---|---|
| 5,155,120 A | 10/1992 | Lazar et al. | |
| 6,090,047 A | 7/2000 | Kass et al. | |
| 6,251,904 B1 * | 6/2001 | Bunnage et al. | 514/252.02 |
| 6,451,807 B1 * | 9/2002 | Emmick et al. | 514/287 |
| 7,312,223 B2 * | 12/2007 | Ghosal et al. | 514/263.34 |
| 2003/0124150 A1 | 7/2003 | Abel et al. | |
| 2003/0139429 A1 | 7/2003 | Cohen | |
| 2004/0038947 A1 | 2/2004 | Wink et al. | |
| 2004/0138306 A1 | 7/2004 | Guth et al. | |

FOREIGN PATENT DOCUMENTS

| EP | 0463756 A1 | 1/1992 |
|---|---|---|
| WO | WO/0043392 A2 | 7/2000 |
| WO | WO/2004/037183 A2 | 5/2004 |

OTHER PUBLICATIONS

Zarain-Herzberg, Angel, et al., "Transcriptional Modulators Targeted at Fuel Metabolism of Hypertrophied Heart", Am. J. Cardiol, vol. 83, No. 3, (1999), pp. 31H-37H.
Kang et al., "DA-8159, a new PDE5 inhibitor, attenuates the development of compensatory right ventricular hypertrophy in a rat model of pulmonary hypertension" Journal of International Medical Research, Cambridge Medical Publications Ltd, GB, vol. 31(6), 2003, pp. 517-528.
Kang et al., DA-8159, A potent CGMP Phosphodiesterase Inhibitor, Attenuates Monocrotaline-Induced Pulmonary Hypertension in Rats II Archives of Pharmacal Research, Natl Fisheries University, Pusan, KR, vol. 26(8), 2003, pp. 612-619.
Zhao Lan et al., "Beneficial effects of phosphodiesterase 5 inhibition in pulmonary hypertension are influenced by natriuretic Peptide activity." Circulation, 2003, vol. 107(2), pp. 234-237.
Takimoto Eiki et al., "Role of PDE5a in cardiac stress response" BMC Pharmacology, Biomed Central, London, GB, vol. 5(1), 2005, p. S26.
Takimoto Eiki et al., "Chronic inhibition of cyclic GMP phosphodiesterase 5A prevents and reverses cardiac hypertrophy." Nature Medicine, 2005, vol. II(2), pp. 214-222.
Ghofrani Ha et al. "Sildenafil increased exercise capacity during hypoxia at low altitudes and at Mount Everest base camp: a randomized, double-blind, placebo-controlled crossover trial." ACC Current Journal Review. Nov. 2004: 13-14.
Hanasato N. et al. "E-4010, a selective phosphodiesterase 5 inhibitor, attenuates hypoxic pulmonary hypertension in rats." Am J Physiol. Aug. 1999;277(2 Pt 1):L225-32.
Inoue H. et al. "Acute and chronic effects of T-1032, a novel selective phosphodiesterase type 5 inhibitor, on monocrotaline-induced pulmonary hypertension in rats." Biol Pharm Bull. Nov. 2002;25(11):1422-6.
Kodama K. et al. "Improvement of mortality by long-term E4010 treatment in monocrotaline-induced pulmonary hypertensive rats." J Pharmacol Exp Ther. Aug. 1999;290(2):748-52.
Ockaili R. et al. "Sildenafil (Viagra) induces powerful cardioprotective effect via opening of mitochondrial K(ATP) channels in rabbits." Am J Physiol Heart Circ Physiol. Sep. 2002;283(3):H1263-9.
Schermuly RT. et al. "Chronic sildenafil treatment inhibits monocrotaline-induced pulmonary hypertension in rats." Am J Respir Crit Care Med. Jan. 1, 2004;169(1):39-45. Epub Sep. 4, 2003.
Office Action mailed Apr. 15, 2011 in Chinese Patent Application No. 200580035426.X, inventors Kass et al., filed Aug. 17, 2005, and Unverified English Translation of Office Action.

\* cited by examiner

*Primary Examiner* — Raymond Henley, III
(74) *Attorney, Agent, or Firm* — Edwards Wildman Palmer LLP; Peter F. Corless; Melissa Hunter-Ensor, Esq.

(57) ABSTRACT

The invention features methods and compositions featuring a PDE5 inhibitor for treating or preventing a cardiac indication in a subject.

13 Claims, 25 Drawing Sheets

Figure 9
A
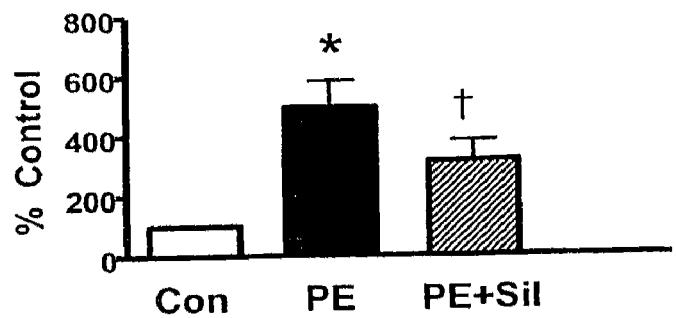
B
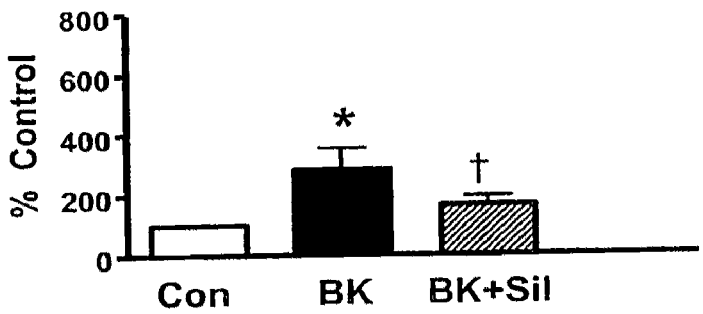
C
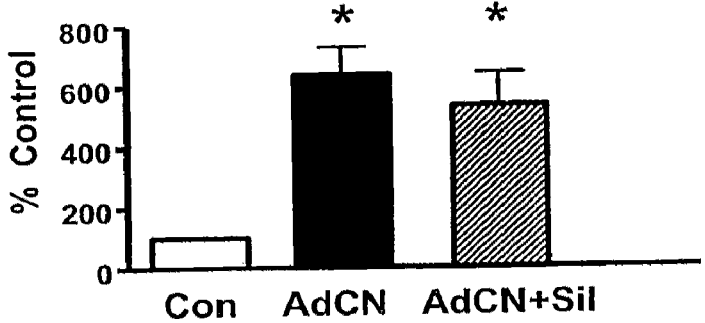

Antiadrenergic effect of PDE5A-I in isolated adult murine myocytes

Takimoto et al. Circ Res 2005;96:100-109

Figure 13 A-B
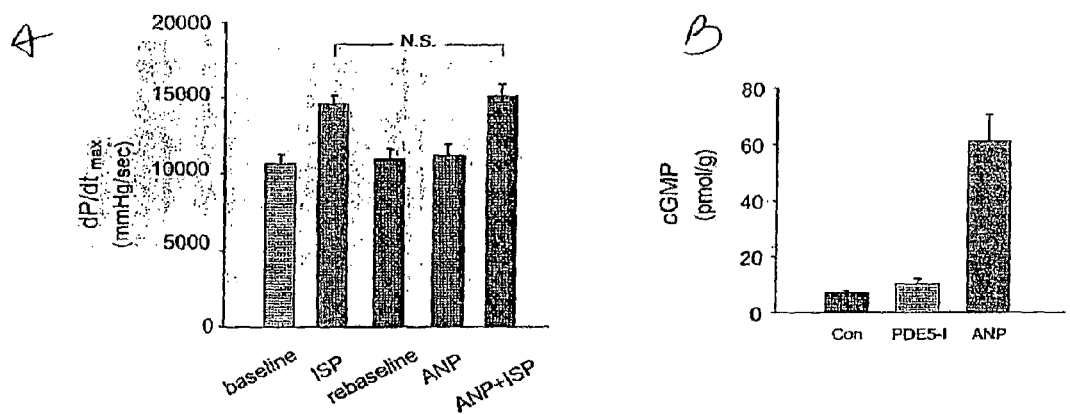

14B

Figures 16A, 16D and 16E
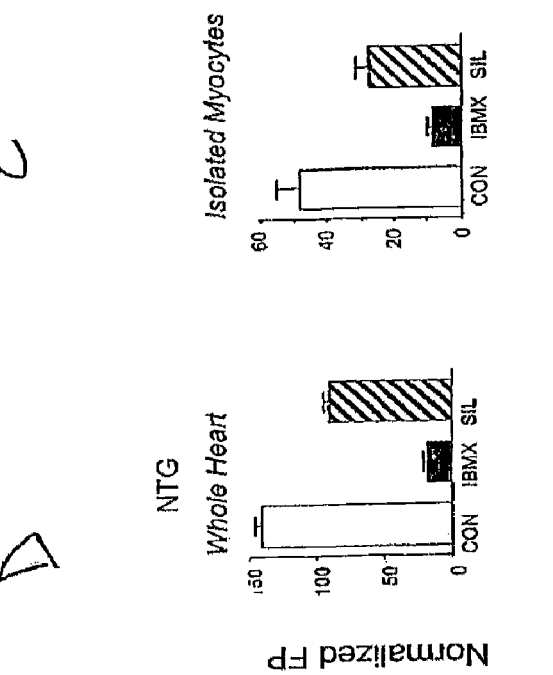
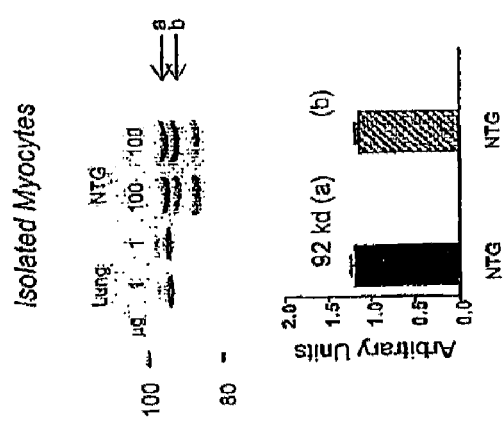

PDE5a in the Murine Heart: Low expression

PDE5a – effect on NOS3 coupling and MMP activation

Takimoto, et al. JCI, 2005; 115:1221-1231

PDE5a inhibition and RhoA/Rho Kinase

Figure 23 A & B
Increased STAT3 Phosphorylation by TAC and IL-6 (gp130) Stimulation is blunted by sildenafil co-treatment
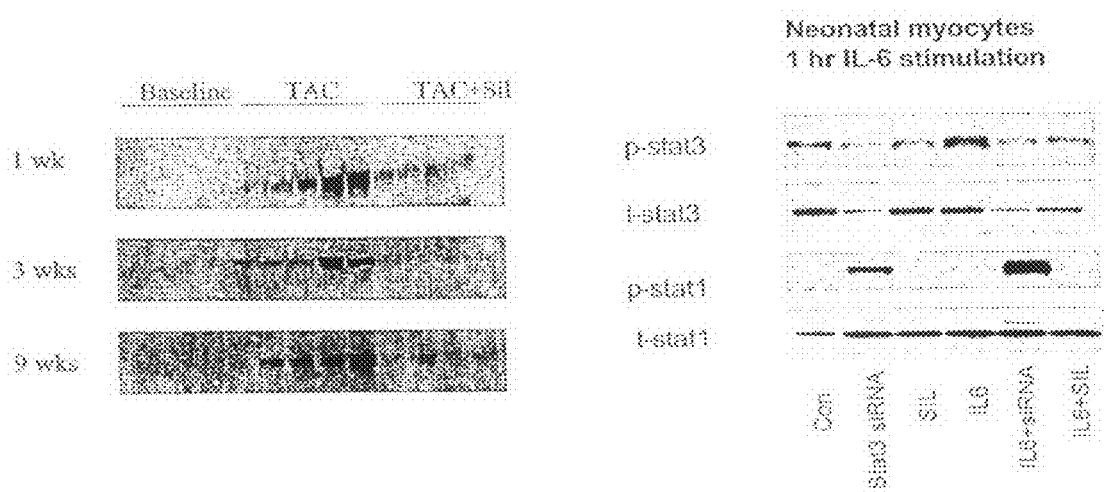

PDE5 INHIBITOR COMPOSITIONS AND METHODS FOR TREATING CARDIAC INDICATIONS

REFERENCE TO RELATED APPLICATIONS

This application claims benefit of U.S. Provisional Application Ser. No. 60/602,134, filed on Aug. 17, 2004, the contents of which are incorporated herein by reference.

STATEMENT OF RIGHTS TO INVENTIONS MADE UNDER FEDERALLY SPONSORED RESEARCH

This work was supported by a grant from the National Institutes of Health, Grant Nos: RO1-AG-18324-03, T32 HL07227-29, and HL-47511. The government may have certain rights in the invention.

BACKGROUND OF THE INVENTION

Hearts exposed to sustained hemodynamic overload undergo molecular, cellular, muscular, and chamber morphologic changes that are typically maladaptive and contribute to progressive cardiac dysfunction and ultimately heart failure. Pathophysiological stimuli that trigger such responses include hypertension, valvular disease, neurohormonal stress, and excessive chamber filling associated with a decline in pump function. These trigger alterations in multiple cellar signaling and transcription pathways that induce muscle cell growth, worsened function of the heart muscle, hypertrophic remodeling and cardiac dilation. Existing therapies cannot adequately prevent these pathological changes. Enlargement of the heart is a chronic and progressive condition that ultimately results in heart failure. Heart failure affects over 5 million Americans, with more than 500,000 new diagnoses annually in the United States alone, and remains the leading cause of death. Nearly half of these patients have hypertension and cardiac hypertrophy with apparent preservation of contraction of the heart, a syndrome for which there are currently no specifically tested and approved treatments. Improved therapeutic compositions and methods for the treatment of cardiac conditions, such as cardiac hypertrophy, are urgently required.

SUMMARY OF THE INVENTION

The invention features methods and compositions for the treatment and prevention of cardiac conditions. This invention is based on the discovery that PDE5A plays an important role in hearts subjected to chronic stresses, such as sustained pressure load, catecholamine stimulation, and other forms of hemodynamic loading, and that PDE5A inhibition in this setting prevents and reverses morphological, cellular, and molecular cardiac remodeling.

In one aspect, the invention generally features a method of enhancing cardiac function in a subject (e.g., a human patient) having a cardiac condition selected from the group consisting of cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, post ischemic cardiac remodeling and cardiac failure, the method comprising administering to the subject an effective amount of a PDE5 inhibitor, where the administration of the inhibitor enhances cardiac function. In one embodiment, the method reduces or reverses cardiac chamber remodeling, cardiac dilation, cardiac muscle cell remodeling (e.g., reduces myocyte hypertrophy) or molecular remodeling. In other embodiments, the PDE5 inhibitor reduces the expression or biological activity of an agent selected from the group consisting of metalloproteinases, calcineurin, mitogen activated kinase, Akt kinase, nuclear factor of activated T-cells (NFAT), RhoA and Rho kinase, PI3 kinase, components of a gp130/Stat-3 pathway, nitrotyrosine, nitric oxide synthase, an agent associated with nitric oxide synthase uncoupling, and an agent associated with oxidative stress. In another embodiment, the PDE5 inhibitor enhances cGMP-dependent signaling via Protein Kinase G. In yet another embodiment, the cardiac chamber, cellular or molecular remodeling is induced by a stimulus (e.g., pressure-overload, neurohormonal stress, a myocardial infarction, or volume-overload). In yet another embodiment, cardiac function is assessed by measuring relaxation rate independent of load, by measuring cardiac contractility independent of load, by measuring cardiac ejection volume independent of load, or by measuring end-systolic volume independent of load. Cardiac function is determined using an assay selected from the group consisting of: Doppler echocardiography, 2-dimensional echo-Doppler, Pulse-wave Doppler, continuous wave Doppler, oscillometric arm cuff, cardiac catheterization, magnetic resonance imaging, positron emission tomography, chest X-ray, ejection fraction test, electrocardiogram, nuclear scanning, invasive cardiac pressures, invasive and non-invasively measured cardiac pressure-volume loops (conductance catheter).

In another aspect, the invention provides a method of preventing, reducing, or reversing cardiac hypertrophy in a subject (e.g., a human patient) having or having a propensity to develop cardiac hypertrophy, the method comprising administering to the subject an effective amount of a PDE5 inhibitor, where the administration of the inhibitor prevents cardiac hypertrophy.

In another aspect, the invention provides a method of preventing, reducing, or reversing cardiac dilation in a subject (e.g., a human patient) having or having a propensity to develop cardiac dilation, the method comprising administering to the subject an effective amount of a PDE5 inhibitor, where the administration of the inhibitor prevents cardiac dilation.

In various embodiments of any of the above aspects, the PDE5 inhibitor reduces cardiac chamber remodeling, reduces cellular remodeling (e.g., by reducing myocyte size), or reduces molecular remodeling (e.g., by modulating the expression or biological activity of an agent selected from the group consisting of metalloproteinases, calcineurin, mitogen activated kinase, Akt kinase, nuclear factor of activated T-cells (NFAT), RhoA and Rho kinase, PI3 kinase, components of the gp130/Stat-3 pathway, nitrotyrosine, nitric oxide synthase, an agent associated with nitric oxide synthase uncoupling and an agent associated with oxidative stress. In one embodiment, the PDE5 inhibitor alters activation of the agent. In another embodiment, the PDE5 inhibitor enhances cGMP-dependent signaling via Protein Kinase G.

In various embodiments of any of the above aspects, the PDE5 inhibitor does not require modulation of a fibrotic process or modulation of a pressure load to treat a cardiac condition. In other embodiments of any of the above aspects, the PDE5 inhibitor enhances cardiac function independent of an effect on arterial blood pressure; independent of an effect on pulmonary blood pressure; or independent of an effect on vasodilation. In various embodiments of any of the above aspects, the PDE5 inhibitor is administered to achieve a concentration that is $0.25 \times IC_{50}$, $0.5 \times IC_{50}$, equal to the $IC_{50}$, $5 \times IC_{50}$, $10 \times IC_{50}$, or $50 \times IC_{50}$ of the PDE5 inhibitor in plasma. In yet other embodiments of any of the above aspects, the PDE5 inhibitor selectively inhibits PDE5. In yet other embodiments of any of the above aspects, the PDE5 inhibitor is administered to achieve an $IC_{50}$ of 10 nM in plasma. In yet other embodiments of any of the above aspects, the PDE5 inhibitor is administered to achieve a peak concentration of 50 nM in plasma. In yet other embodiments of any of the above aspects, the PDE5 inhibitor is administered to achieve an effective concentration of 0.1 nM-100 nM, 0.1-75.0, 0.5-50.0, 5-10, 10-20, 20-30, or 30-40 nM in plasma. In yet other embodiments of any of the above aspects, the effective concentration is sustained over the course of at least 4-8, 8-12, or 12-24 hours.

In another aspect, the invention provides a method for preventing, reducing, or reversing a maladaptive cardiac alteration in a subject having or having a propensity to develop the alteration, the method comprising administering to the subject an effective amount of a PDE5 inhibitor, where the inhibitor prevents the maladaptive cardiac alteration (e.g., an alteration associated with hypertension or a condition selected from the group consisting of cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, post ischemic cardiac remodeling and cardiac failure).

In another aspect, the invention provides a method for enhancing myocardial energetics in a subject in need thereof, the method comprising administering to the subject an effective amount of a PDE5 inhibitor, where the administration of the inhibitor enhances myocardial energetics. In other embodiments, myocardial energetics are assayed by assessment of high energy phosphate storage (phosphocreatine) relative to higher energy phosphate utilization (adenosine tri-phosphate—ATP), assessment of ATP flux to ADP, assessment of levels of ADP and inorganic phosphate, assessment of oxygen consumption by the heart in relation to total cardiac workload, assessment of oxygen consumption by isolated cardiac muscle in relation to total muscle workload.

In another aspect, the invention provides a composition for the treatment of a condition selected from the group consisting of cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, post ischemic cardiac remodeling and cardiac failure, the composition comprising at least 0.1-200 mg of a PDE5 inhibitor in a pharmaceutically acceptable excipient, where administration of the composition to a subject results in an effective concentration of at least 0.1-100 nM (e.g., 0.1-75 nM) in plasma.

In another aspect, the invention provides a composition for the treatment of cardiac hypertrophy, the composition comprising at least 0.1-200 mg of a PDE5 inhibitor in a pharmaceutically acceptable excipient.

In various embodiments of the above aspects, administration of the composition to a subject results in an effective concentration of at least 0.1-100 nM (e.g., 0.1-75 nM, 0.5-50 mM, 1-25 nM, 5-10 nM, 10-20 nM, 20-30 nM, or 30-40 nM) in plasma. In other embodiments, the composition comprises at least 10, 20, 100, or 150 mg of a PDE5 inhibitor. In yet other embodiments of the above aspects, the composition provides for the sustained release of the PDE5 inhibitor In still other embodiments, the composition provides for release of the PDE5 inhibitor over at least 4-8, 8-12, or 12-24 hours. In yet other embodiments of the above aspects, the composition consists essentially of a PDE5 inhibitor.

In another aspect, the invention provides pharmaceutical pack comprising a composition comprising at least 5 mg of a PDE5 inhibitor in a pharmaceutically acceptable excipient, where the pharmaceutical pack is labeled for use in the treatment or prevention of a condition selected from the group consisting of cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, post ischemic cardiac remodeling and cardiac failure.

In a related aspect, the invention provides pharmaceutical pack comprising a composition comprising at least 5 mg of a PDE5 inhibitor in a pharmaceutically acceptable excipient, where the pharmaceutical pack is labeled for use in the treatment or prevention of cardiac hypertrophy.

In various embodiments of the previous aspects, the pack comprises at least 10 mg, 20 mg, or 100 mg of a PDE5 inhibitor. In other embodiments, the PDE5 inhibitor is provided in a sustained release formulation. In other embodiments, the composition consists essentially of a PDE5 inhibitor. In other embodiments, further comprising written instructions for administering the composition to a subject for the treatment or prevention of cardiac hypertrophy.

BRIEF DESCRIPTION OF THE DRAWINGS

FIG. 1A shows heart sections (upper) and M-mode echocardiogram (lower), scale is one mm. Abbreviations and their meanings follow: Con: sham Operated mice—3 weeks after operation, TAC: transverse aortic constriction (which induces pressure overload), +/−Sil: with or without sildenafil treatment. In non-sildenafil treated animals, sustained pressure-load results in marked heart hypertrophy and dilation. By 9-weeks, hearts were profoundly remodeled and display a significant reduction in cardiac function. Note the echocardiograms show dilation and reduced wall shortening. Sildenafil treated animals show a marked reduction in the development of both hypertrophy and chamber dilation, and have preserved cardiac function. FIG. 1B provides three summary graphs for the ratio of heart weight to tibia length; percent fractional shortening (derived from echocardiography); and left ventricular end-systolic diameter (a measure of cardiac dilation/remodeling and systolic function) in control, and TAC mice three and nine weeks after the operation. Abbreviations and their meanings for FIG. 1B follow: HW/TL heart weight/tibia length, fractional shortening (FS) and LV end-systolic diameter (LV-ESD) by echocardiography (mean±sem.; n≧6); *$p<0.001$ vs vehicle. Cardiac hypertrophy increased profoundly in non-sildenafil treated animals, and was reduced by more than 50% by sildenafil treatment. Heart function also improved with treatment. FIG. 1C displays six micrographs and a summary graph. The micrographs show PAS-methenamine-stained myocardium from vehicle versus Sil treated animals. The dark blue color reflects interstitial fibrosis. Scale bar represents 100 μm. Lower bar graph shows summary data for myocyte cross sectional diameter (CSD); *$p<0.01$ vs vehicle treatment. Sildenafil treatment during sustained pressure overload blocked the enlargement of cardiac muscle cell hypertrophy, and also inhibited the development of interstitial fibrosis.

FIG. 3A includes three graphs showing that one week of TAC induces cardiac hypertrophy without chamber dilatation. Abbreviations are as in FIG. 1. Wall thickness and LV-end-diastolic volume (LV-EDD) were determined by echocardiography. FIG. 3B (left panel) includes two micrographs showing PAS-methenamine-stained myocardium that displays myocyte hypertrophy and interstitial fibrosis at one week TAC (before treatment). This hypertrophy and fibrosis was reduced by subsequent two weeks of treatment with sildenafil (TAC-3 week, 2 week Sil). Scale is 100 μm. FIG. 3B (right panel) is a graph providing summary data; *$p<0.05$ vs Con; †$p<0.05$ vs TAC 1 week. FIG. 3C is a graph showing the reversal of hypertrophy by sildenafil. Data start after 1-week of TAC (both groups had the same initial level of hypertrophy at this time). Animals were then randomized to receive either placebo or sildenafil treatment. The sildenafil treated group shows reduction in cardiac hypertrophy and sustained cardiac function (fractional shortening) over the ensuing 2-week period. In contrast, placebo treated hearts undergo progressive hypertrophy and cardiac dysfunction. P-values are for analysis of covariance for treatment effect.

FIGS. 4A and 4B show that sildenafil treated hearts have less cardiac remodeling and improved contractile and diastolic function relative to controls. FIG. 4A shows in vivo heart function assessed comprehensively by pressure-volume relations in sham control mice (Con), control mice treated with 3-weeks of sildenafil (3-week Sil), 3 weeks TAC with or without sildenafil, and mice with hypertrophy induced by 1-week TAC and then sildenafil added for two additional weeks (3-week TAC+Delay Sil 2 week). In all examples with TAC, the increase in systolic pressure was similar and was unaltered by treatment by sildenafil. Thus, all of the previously shown and present changes in heart morphology and function were independent of any changes in the pressure load itself. Untreated hearts also showed a rightward shift of the loops and end-systolic pressure-volume relation (line connecting upper left corner) consistent with hypertrophy-remodeling. Treatment of sham control hearts—i.e. without TAC induced pressure overload—by sildenafil did not change cardiac function. Only when the heart was under increased stress, in this case by the TAC pressure-load was an effect of sildenafil observed. In this instance, the pressure-volume loops were shifted to smaller volumes, and the end-systolic pressure-volume relation remained in its normal position. This reflects the prevention of remodeling and improved overall heart function. FIG. 4B is a series of six graphs presenting summary data relating to cardiac function parameters in mice. The top left shows arterial elastance—a measure of afterload (Ea). This was similarly increased by TAC in all models in which TAC was employed, and was not reduced with sildenafil treatment. The top right shows ejection fraction (EF) a measure of net systolic function. EF declined with chronic TAC, and was restored to normal levels in animals treated concomitantly with sildenafil, and those in which sildenafil treatment was delayed for 1 week (i.e. reversal experiments). Importantly, this recovery of EF occurred without altering the pressure load with sildenafil treatment. The two middle panels show measures of contractility that were independent of heart loading: PMXI—maximal power index, and Msw—preload recruitable stroke work. These measures were both significantly improved in the hearts receiving sildenafil as compared to non-treated TAC. The lower panels display measures of diastolic function: Tau (isovolumic relaxation time constant); $dP/dt_{mn}$—peak rate of pressure decline. TAC resulted in a prolongation of cardiac relaxation reflected in both parameters, and this too was restored to normal levels in the sildenafil treated animals. *$p<0.001$ vs Con and 3-week Sil; † $p<0.05$ vs all other groups; ‡ $p<0.01$ vs Con, 3-week Sil, and 3-week TAC.

FIG. 5A is a series of formalin fixed heart sections (left panel), and two graphs showing the heart weight/tibia length (HW/TL) ratio (middle panel) and myocyte cross sectional diameter (CSD, right panel) from sham control mice and 3-week post-operation TAC mice in the presence or absence of EMD360527 treatment. The abbreviations for FIG. 5A follow: Con: 3 wk vehicle-treated sham, EMD: 3 wk EMD360527-treated sham, TAC: 3 wk vehicle-treated TAC, TAC+EMD; 3 wk EMD360527-treated TAC. *$p<0.05$ vs Con; †$p<0.05$ vs vehicle-treated TAC. As with sildenafil, EMD360527 treatment prevented the development of both cardiac hypertrophy and accompanying chamber dilation and remodeling. FIG. 5B displays representative M-mode echocardiography (left panel) and three graphs showing a summary of cardiac mechanics based on invasive pressure-volume catheterization (right panels). Abbreviations for FIG. 5B are described as previously or as follows: Ea—ventricular afterload was identically increased by TAC with or without concomitant EMD360527. Maximal cardiac power index (PMXI) rose and isovolumic relaxation (Tau) was shortened significantly in EMD-TAC as compared to TAC. These data were nearly identical to those obtained using sildenafil (i.e. FIG. 5C shows a dot blot and a graph that summarizes the analysis of cardiac fetal gene expression. Abbreviations for FIG. 5C are as follows: ANP: A-type natriuretic peptide; B-type natriuretic peptide, βMHC: β-myosin heavy chain, and αSkA: α skeletal actin, and calcium handling proteins PLB: phospholamban, SERCA: sarcoplasmic reticular calcium ATPase (upper panel). Summary data are shown normalized to GAPDH expression (lower panel). TAC resulted in fetal gene recapitulation—with increases in natriuretic peptide, βNHC, and αSkA expression, and reductions in PLB and SERCA. PDE5A inhibition reversed fetal gene recapitulation and improved expression of $Ca^{2+}$ handling proteins altered by TAC. *$p<0.05$ vs Con, †$p<0.05$ vs TAC. FIG. 5D is a graph showing whole myocardial cGMP levels increased with TAC itself, but there was a slight decline in TAC treated with EMD360527. As displayed in the next figure, this response was similar to that observed with sildenafil, and corresponds to a marked fall in natriuretic peptide expression despite inhibition of PDE5. *$p<0.05$ vs Con and EMD, †$p<0.05$ vs TAC.

FIG. 6A is a graph showing whole heart PKG-1 activity. *$p<0.05$ vs Con; †$p<0.05$ vs vehicle-treated TAC. PKG-1 is activated by cGMP, which in turn is increased if PDE5 is inhibited by sildenafil. Under rest conditions, there was little net effect from PDE5 inhibition on PKG-1 activation. In contrast, in hearts with hypertrophy/remodeling following 3-weeks TAC, sildenafil markedly increased PKG-1 activity. FIG. 6B is a graph showing total cGMP-esterase activity in sham control hearts (Con) and three week TAC hearts (TAC). At baseline, the percent of total activity that was blocked by co-incubation with a selective PDE5A inhibitor (sildenafil or tadalafil) was approximately 30%. Broad PDE inhibition by IBMX is shown as a control. With sustained pressure-overload (TAC), total cGMP-esterase activity increased (*p<0.005). The proportion of this activity attributable to PDE5 also rose to nearly 60% of the total (100% increase in enzyme activity) (p<0.001 by 2-way ANOVA). FIG. 6C is a graph showing whole heart cGMP levels. *p<0.05 vs Con. FIG. 6D (upper panel) displays two Western blots for the calcium-dependent phosphatase calcineurin (Cn) and mitogen activated kinase—extracellular signal-regulated kinase (ERK1/2). FIG. 6D (lower panel) provides two graphs summarizing the Western blot results (n=4-5 for each). ERK1/2 summary results are shown as the ratio of phospho (p) to total (t) protein. *p<0.05 vs Con; †p<0.05 vs vehicle-treated TAC (TAC). One week TAC increased expression and activity of both enzymes. This effect was blunted by sildenafil. At the later TAC time point (9 weeks), only calcineurin remained markedly increased. Calcineurin was still diminished in heart co-treated by sildenafil.

FIG. 7A (left panel) is a series of three micrographs. These micrographs show the effect of phenylephrine (PE) on myocyte hypertrophy as shown by increased sarcomere organization (FIG. 7A α-actinin staining, (×1000)). FIG. 7B (right panel) is a graph that quantitates protein synthesis as 3H-leucine incorporation percent in myocytes with organized sarcomeres (*p<0.05 vs Con; †p<0.05 vs PE). Sildenafil treatment reduced sarcomere organization and protein synthesis in PE-stimulated myocytes. FIG. 7C is a series of ten micrographs showing myocytes transfected with NFAT-promoter coupled to β-galactosidase (×200). Blue staining indicates NFAT activation. Abbreviations for FIG. 7C are as follows: PE—phenylephrine; BK—BayK 8644; AdCn—calcineurin overexpression by adenovirus. Panels (1,3,5) are with phase contrast filter (+fil), others are without (−fil). FIG. 7D is a series of three graphs showing the quantitative analysis of NFAT (i.e. β-galactosidase) activity (*p<0.05 vs Con; †p<0.05 vs hypertrophy stimulation (PE, BK or AdCn)). Sildenafil treatment inhibited NFAT activation by PE and by BayK 8644. However, NFAT activated in cells with calcineurin constitutively active could not been blocked by sildenafil. This supports a more proximal target for the drug effect.

FIG. 9A-9C are graphs showing the assessment of NFAT promoter activation in neonatal myocytes transfected with an adenovirus coding for the NFAT promoter coupled to luciferase. Cells were then exposed to phenylephrine (PE), calcium enhancement (BK), or an adenovirus encoding active calcineurin (AdCn), and co-incubated with vehicle or sildenafil. After a forty-eight hour incubation, cells were assessed for luciferase activity by luminometer. Data are shown as percent change normalized to control level. Sildenafil (Sil) inhibited PE and BK induced NFAT promoter activity, but not AdCn-induced activity. These results were similar with the findings using an NFAT-promoter coupled to beta-galactosidase virus. *p<0.05 vs Con, †p<0.05 vs hypertrophy stimulation (PE, BK, or AdCn).

FIG. 10A is a Western blot and summary data of phospho (p) and total (t) Akt at 1 and 9 week TAC. FIG. 10B is a graph showing the results of an Akt activity assay. FIG. 10C is a graph showing the results of a PI3K activity assay (data at 3 week TAC, S: sildenafil treatment only). PI3K activity and Akt activity were both significantly increased at 1 and 9 weeks of TAC, and were inhibited towards control levels by treatment with sildenafil. FIG. 10D is a Western blot and a graph showing a summary of data for GSK3 expression and activation. GSK3, is a downstream kinase that regulated hypertrophy, and is activated by Akt and other kinases. TAC induced GSK3β activity was reduced by sildenafil at 9-week but not at 1-week. FIG. 10E shows the effect of chronic effect of sildenafil on transgenic mice overexpressing constitutive active Akt in the heart. Post-mortem hearts are displayed at the top, and summary data based on echo and post-mortem analysis below. Scale marks are 1 mm. LV mass from serial echocardiography and post-mortem study is shown below, with higher LV mass in AktTG (p<0.05) for all comparisons. Akt overexpression itself resulted in greater ventricular hypertrophy, and sildenafil did not alter this mass increase. This indicates that the effect of sildenafil on Akt signaling (i.e. panels A-C) is upstream of Akt itself. *p<0.05 vs control; †p<0.05 vs TAC; C: control; T: TAC; T+S: TAC+sildenafil; applies to all panels.

FIG. 11A is a trace showing that sarcomere shortening increased with ISO, but was markedly blunted by the concomitant exposure to the PDE5 inhibitor, sildenafil. FIG. 11B shows calcium transients measured by the fluorescent dye Indo-2AM. The dye signal is expressed as a ratio of two emission wavelengths. FIGS. 11C and 11D are graphs quantitating the results shown in FIGS. 11A and 11B. FIG. 11E includes two pressure volume loops showing results from intact mouse hearts. ISO produces a widening of the pressure volume loop and shift of the upper corner point (end-systole) to the left. This reflects an increase in contractility. With SIL treatment, the ISO response was blunted, and there was a negligible increase in contractility. FIG. 11F is a graph that summarizes data based on the maximal rate of rise in pressure ($dP/dt_{max}$). With ISO, there was a rise in $dP/dt_{max}$, after re-establishing baseline, sildenafil was given alone. This had no effect on the heart at rest. When ISO was added, the expected contractile rise in $dP/dt_{max}$, was not observed.

FIGS. 12A and 12B includes three panels (FIG. 12A) and a graph (FIG. 12B). FIG. 12A shows the effect of PDE5A inhibition on chronic ISO-induced cardiac hypertrophy in intact hearts. FIG. 12B shows the effect of PDE5A inhibition on the heart weight/tibia length ratio. ISO was infused by osmotic pumps in mice for 2 weeks, resulting in a near 50% increase in left ventricular hypertrophy (mass/tibia length). Concomitant treatment with a PDE5a inhibitor prevented this response.

FIGS. 14A and 14B are traces showing the direct effect of a PDE5a inhibitor (sildenafil; SIL) on isoproterenol (ISO) stimulated isolated adult cardiac muscle cell contraction and calcium transients with or without inhibition of guanylate cyclase (sGC) by ODQ. sGC generates cGMP which in turn is catabolized by PDE5a. Blocking the synthesis of cGMP by sGC(ODQ) prevented the PDE5a inhibitor from blunting an ISO response. This supports the importance of a cGMP regulated mechanism for the PDE5a inhibitory effect.

FIG. 15A shows Protein kinase G-1 (PKG-1) activity in myocytes. Treatment with sildenafil (SIL) or tadalafil (TAD) alone slightly raised PKG-1 activity ($p<0.05$), but increased it by 70% ($p<0.001$) when combined with ISO (30% over ISO alone, $p<0.001$). FIG. 15B shows cGMP production as measured by a cGMP-sensitive fluorescent energy resonance transfer (FRET) probe in control rat neonatal myocytes. SIL (500 nM) and ISO (100 nM) raised cellular cGMP ($p<0.01$), with a greater change by their combination. Addition of the NO donor DEA/NO (5 μM) increased this further. FIG. 12C shows a summary of data for relative FRET change (*$p<0.05$ vs untreated cells).

FIGS. 16A-16E show PDE5A protein expression and activity in isolated adult myocytes and in whole cardiac myocardium. FIG. 16A shows a Western blot (upper panel) for PDE5A protein expression in isolated adult myocytes (protein loading shown) with summary data (lower panel) from 4-6 separate blots ($n \geq 6$ hearts in each group) displayed. A double banding pattern is observed (a, b). Loading for myocytes was at 100 μg, while for lung it was 1 μg. FIG. 16B is a graph showing relative levels of PDE5a gene expression in lung, isolated cardiac muscle cells (MYO), and whole myocardium (HRT). There were very low levels of expression of PDE5a in the heart compared with lung, and 10-fold lower levels in isolated myocytes than in whole heart. FIG. 16C is a Western blot showing PDE5A protein expression in whole murine heart, and 20 μg loading used for lung and heart—confirming these differences in expression at the protein level. FIGS. 16D and 16E are graphs showing results of cGMP-esterase activity assays in both total heart and isolated adult heart muscle cells. Total activity (CON, normalized fluorescence polarization (FP) units) was largely blocked by the broad PDE inhibitor IBMX (50 μM), whereas sildenafil (SIL, 100 nM) lowered this activity by ~30% ($p<0.001$). This shows that about 30% of the total cGMP-esterase activity was attributable to PDE5a in normal heart muscle and muscle cells.

FIG. 17A shows that PDE5A immunostaining in myocytes was present in cytosol and in more prominent at z-bands (left panel). Corresponding staining was for z-band protein α-actinin (right panel). FIG. 17B shows that PDE5A staining was prevented by co-incubation with blocking peptide (Cell Signaling, 5:1 BP/Ab (left); right: α-actinin). FIG. 17C shows that PDE1C staining was unaffected by this blocking peptide (PDE1C: left; right panel: α-actinin). FIG. 17D shows PDE5A staining in another cardiomyocyte. FIG. 17E shows the same cell stained for nitric oxide synthase 3 (NOS3, or eNOS), and FIG. 17F shows that this staining co-localized with PDE5a at z-bands.

FIG. 18A is a series of four panels showing an exemplary Doppler flow and pressure. FIG. 18B is a graph showing that maximal LV ventricular power index was used to assess cardiac contractility. Dobutamine increased this parameter nearly 200% for the initial test (1); after sildenafil (dotted line; 2), the dobutamine stimulation effect was markedly diminished.

FIG. 21A shows hypertrophic changes in a TAC heart relative to the normal heart of a sham mouse. FIG. 21B is a Western blot performed in a non-denatured gel showing that levels of NOS3-dimers (NOS3-d) were decreased in TAC hearts at 3 weeks post-surgery, while levels of NOS3 monomers (NOS3-m) were increased. This is indicative of NOS uncoupling, wherein NOS3 converts from an enzyme which synthesizes principally nitric oxide to one that generates superoxide. FIG. 21C (lower panel) is a pair of micrographs showing dihydroethidium (DHE)—an oxidative stress sensitive dye—staining in the myocardium of sham and TAC mice. FIG. 21C (upper panel) is a pair of graphs showing that calcium dependent NOS activity to generate nitric oxide was reduced in TAC mice three weeks after surgery. FIG. 21D is a graph showing that superoxide levels formed by NOS3 were increased. FIG. 21E is a Western blot showing that NOS3 dimer levels (280 kD) were reduced in TAC mice three weeks after pressure-overload, and that sildenafil treatment prevented the loss of NOS dimer (280 kD band) in these animals. FIG. 21F is a gelatinase zymogram showing that sildenafil inhibited gelatinase activity (metalloproteinase MMP-2 and MMP-9, both gelatinases)

FIG. 22A shows that RhoA and ROCK2 protein expression were increased in mice exposed to 3-weeks of TAC. Both were blunted by PDE5A inhibition treatment by sildenafil. FIGS. 22B and 22C show that RhoA and total ROCK activity was increased in mice exposed to TAC for three weeks. This increase in activity was inhibited by sildenafil.

FIGS. 23A and 23B are a series of six phospho-blots showing STAT3 phosphorylation. FIG. 23A shows that STAT3 (signal transducer and activator of transcription 3) phosphorylation (i.e. activation) increases at one week, three weeks, and nine weeks after TAC surgery. Treatment with sildenafil prevented this activation. FIG. 23B results of experiments in neonatal rat myocytes, showing that interleukin 6 (IL-6) activates STAT3 and not STAT1. Treatment with sildenafil prevented the STAT activation. p-STAT3 and t-STAT3 are for phosphorylated and total levels respectively, and similar abbreviations apply for the STAT1 lanes. The sildenafil effect on STAT3 was not working at the transcriptional level since t-STAT3 was unaltered. This was further confirmed by comparison to cells in which STAT3 expression is blocked by a silencing RNA (siRNA). This lowered STAT3, but reciprocally increased STAT1 expression and activity. This was not observed with sildenafil treatment.

FIG. 24A (left panel) is an NMR spectroscopic image of a TAC heart three weeks after surgery. The heart is shown in cross-section. FIG. 24A (right panel) is an NMR spectra showing high energy phosphate metabolism in the heart. FIG. 24B is a graph showing that the ratio of phosphocreatine (PCr) to total ATP was reduced in TAC cardiac tissues three weeks after surgery. This effect was blunted by sildenafil treatment.

DETAILED DESCRIPTION OF THE INVENTION

Definitions

Figure 1:
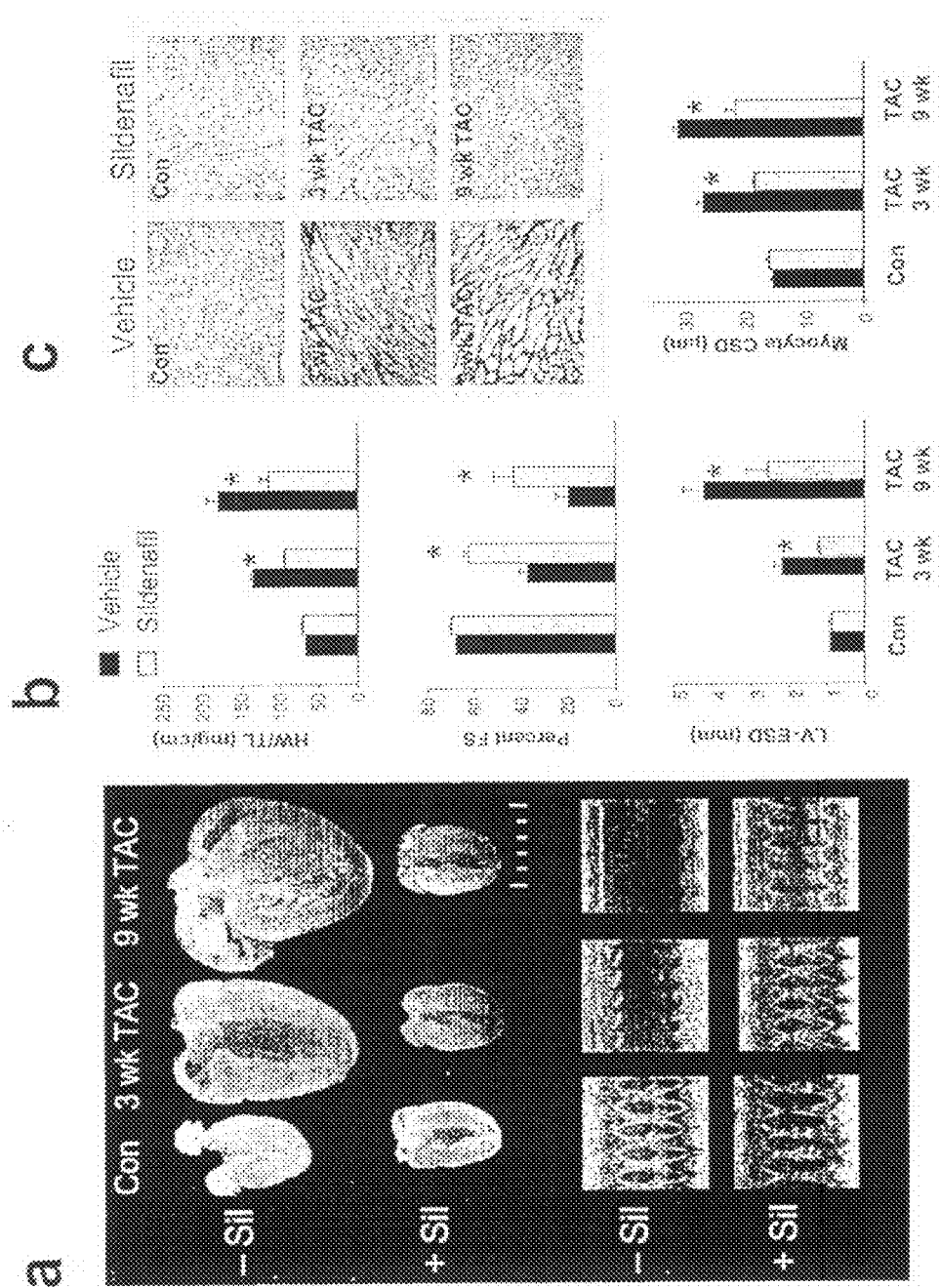
FIGS. 1A, 1B, and 1C show that inhibition of PDE5A with sildenafil prevents pressure load-induced cardiac hypertrophy.

By "cardiac hypertrophy" is meant any undesirable cardiac muscle cell growth, increase in cardiac chamber mass relative to body size, or increase in cardiac chamber wall thickness at normal or increased chamber volume.

By "cardiac condition" is meant any cardiac disease or disorder.

By "cardiac chamber remodeling" is meant an undesirable morphological alteration in a cardiac tissue in response to a pathophysiologic stimulus (e.g., hypertension, myocardial infarction, neurohormonal stress, volume over-load).

By "cellular remodeling" is meant an undesirable alteration in a cardiac cell in response to a pathophysiologic stimulus. Changes in cellular remodeling include, but are not limited to, changes in any one or more of the following: myocyte hypertrophy, calcium handling (e.g., cyclic changes in intracellular calcium with myocyte stimulation, uptake and release of calcium from internal cellular stores, such as the sarcoplasmic reticulum, interaction of calcium with a contractile protein or regulatory protein), activating current (e.g., sodium), and repolarizing current (e.g., potassium).

By "molecular remodeling" is meant an alteration in the transcription or expression of a gene or an alteration in the biological activity of a protein in a cardiac tissue in response to a pathophysiologic stimuli.

By "enhancing cardiac function" is meant producing a beneficial alteration in the pumping performance and capacity of the heart.

By "maladaptive cardiac alteration" is meant an undesirable change in the heart, or in a cell thereof, in response to a pathophysiologic stimulus.

By "PDE5 inhibitor" is meant a compound that inhibits cGMP hydrolysis by phosphodiesterase-5. PDE5 inhibitors preferably reduce PDE5 enzymatic activity by at least 5% (e.g., 10%, 15%, 20%, 30%, 50%, 60%, 75%, 85%, 90% or 95%). Methods for assaying the activity of a PDE5 inhibitor are known in the art and are described herein (e.g., at Example 4).

By "treat" is meant decrease, suppress, attenuate, diminish, arrest, or stabilize the development or progression of a disease.

By "disease" is meant any condition or disorder that damages or interferes with the normal function of a cell, tissue, or organ.

By "modulation" is meant any alteration (e.g., increase or decrease) in a biological function or activity.

By "reduce" or "increase" is meant alter negatively or positively, respectively, by at least 5%. An alteration may be by 5%, 10%, 25%, 30%, 50%, 75%, or even by 100%.

By "reduces cardiac hypertrophy" is meant produces at least a 5% decrease in a morphological, cellular, or molecular remodeling.

By "reverses cardiac hypertrophy" is meant produces a desirable alteration in a morphological, cellular, or molecular cardiac phenotype, wherein the altered phenotype is substantially that characterizing normal cardiac tissue.

By "subject" is meant a mammal, such as a human patient or an animal (e.g., a rodent, bovine, equine, porcine, ovine, canine, feline, or other domestic mammal).

An "effective amount" is an amount sufficient to effect a beneficial or desired clinical result.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Methods of the Invention

The invention generally provides compositions comprising PDE5 inhibitors that are useful for the prevention or treatment of a cardiac condition. Compositions and methods of the invention are particularly useful for the treatment or prevention of cardiac conditions that are characterized by morphological, cellular, or molecular remodeling. Typically, such remodeling occurs in response to hemodynamic stress such as hypertension, valvular disease, neurohormonal stress, cardiac infarction, or volume over-load. This invention is based, in part, on the discoveries that PDE5 is expressed at functionally significant levels in cardiac tissue; that these levels target potent regulators of cardiac remodeling and function; and that inhibition of specific cyclic guanosine 3',5'-monophosphate phosphodiesterases (PDE5) treats or prevents cardiac hypertrophy and other cardiac conditions.

The methods herein include administering to the subject (including a subject identified as in need of such treatment) an effective amount of a compound described herein, or a composition described herein to produce a beneficial effect on a cardiac tissue. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of a compound described herein, such as a PDE5 inhibitor (e.g., vardenafil, tadalafil, or sildenafil) to a subject (e.g., animal, human) in need thereof, including a mammal, particularly a human. Such treatment will be suitably administered to subjects, particularly humans, suffering from, having, susceptible to, or at risk for a cardiac disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which hypertrophy, including morphological, cellular, or molecular remodeling Cardiovascular Function Cardiac conditions, such as cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy (e.g., hypertrophic cardiomyopathy originating from a genetic or a secondary cause), post ischemic and post-infarction cardiac remodeling and cardiac failure, are associated with maladaptive cardiac alterations, cardiac chamber, cellular, and molecular remodeling. Compositions of the invention may be used to enhance cardiac function in a subject having reduced cardiac function. Desirably, cardiac function is increased by at least 5%, 10% or 20%, or even by as much as 25%, 50% or 75%. Most advantageously, cardiac function is enhanced or damage is reversed, such that the function is substantially normal (e.g., 85%, 90%, 95%, or 100% of the cardiac function of a healthy control subject). Alternatively, such assays are used to monitor the condition of a subject prior to, during, or following treatment with a PDE5A inhibitor. Treatments that increase cardiac function are useful in the methods of the invention.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X-ray contrast ventriculography, nuclear imaging ventriculography, computed tomography imaging, rapid spiral computerized tomographic imaging, 3-D echocardiography, invasive cardiac pressures, invasive cardiac flows, invasive cardiac pressure-volume loops (conductance catheter), non-invasive cardiac pressure-volume loops.

Prophylactic and Therapeutic Applications

Heart disease is typically a chronic and progressive illness that kills more than 2.4 million Americans each year. There are ~500,000 new cases of heart failure per year, with an estimated 5 million patients in the United States alone having this disease. Early intervention is likely to be most effective in preserving cardiac function. Desirably, methods of the invention are used to prevent as well to reverse the morphological, cellular, and molecular remodeling that is associated with heart disease. In one embodiment, heart disease is prevented by administering an effective amount of a PDE5 inhibitor to a subject at risk of developing a cardiac condition. To determine a subject's propensity to develop a cardiac condition, the subject's cardiac risk is assessed using any standard method known in the art. The most important indicators of cardiac risk are age, hereditary factors, weight, smoking, blood pressure, exercise history, and diabetes. Other indicators of cardiac risk include the subject's lipid profile, which is typically assayed using a blood test, or any other biomarker associated with heart disease or hypertension. Other methods for assaying cardiac risk include, but are not limited to, an EKG stress test, thallium stress test, EKG, CT scan, echocardiogram, magnetic resonance imaging study, non-invasive and invasive arteriogram, and cardiac catheterization.

PDE5 inhibition is also useful for treating maladaptive cardiac alterations that involve chamber, cellular, and molecular remodeling leading to cardiac dysfunction, hypertrophy, and dilation, and by other cardiac indications. Advantageously, the methods of the invention are useful for the reduction of morphological, cellular and molecular remodeling in cardiac tissues that are under stress related to pressure-overload, neurohormonal stress, myocardial infarction, or volume-overload. Accordingly, the methods of the invention are particularly useful in patient's having uncontrolled hypertension or any other chronic condition that places stress on the heart.

PDE5 Inhibitors

PDE5 is expressed in systemic and pulmonary arterial and venous smooth muscle cells—particularly in the corpus cavernosum. In light of this expression, PDE5 inhibitors were initially of interest for their vasodilatory effects. Sildenafil, for example, was first studied as an anti-anginal medication in anticipation of its capacity to dilate coronary arteries. Early clinical studies of sildenafil for the treatment of angina, however, were disappointing, as its impact on arterial vasodilation was very modest. These clinical studies did lead to the finding that erectile function was improved as a common side effect of sildenafil administration. Sildenafil enhances an erection by decreasing the breakdown of cGMP and thus prolonging the vasodilatory effects induced in the penile circulation by nitric oxide in response to sexual stimulation. This same cyclic nucleotide signaling pathway mediates the smooth-muscle relaxing effects of nitric oxide necessary for normal erectile function. Down-regulation of this pathway is central to the pathophysiology of many forms of erectile dysfunction.

Sildenafil is selective for PDE5. Prior to the discovery reported herein, PDE5 levels in cardiac muscle were thought to be functionally insignificant. Indeed, as recently as 2003, major reviews on this class of pharmaceuticals noted no known direct influences on cardiac muscle, and minimal effects on the arterial blood pressure. This suggested that PDE5 inhibitors would not reduce the load on the left heart sufficient to alter heart function, or morphology (i.e. hypertrophy), nor modify molecular and cellular remodeling. In fact, PDE5 plays only a minor role in regulating the heart under rest conditions—much as an automotive brake has little effect on an idling car.

Surprisingly, the results reported herein indicated that PDE5A plays an important role in hearts subjected to stress, and that PDE5A inhibition prevents and reverses morphological, cellular, and molecular remodeling in hearts that are subject to stress related to pressure-overload, neurohormonal stress, myocardial infarction, or volume-overload. Surprisingly, the therapeutic effects of PDE5 inhibitors on heart function, left heart function, hypertrophy, and molecular and cellular remodeling are achieved in the complete absence of any change in the load imposed on the heart.

PDE5 inhibitors are known in the art, and include, but are not limited to, sildenafil (Compound 1), vardenafil (Compound 2), tadalafil (Compound 3), EMD 360527, DA 8159, or analogs thereof, or any other compound that inhibits cGMP hydrolysis by phosphodiesterase-5 (PDE5).

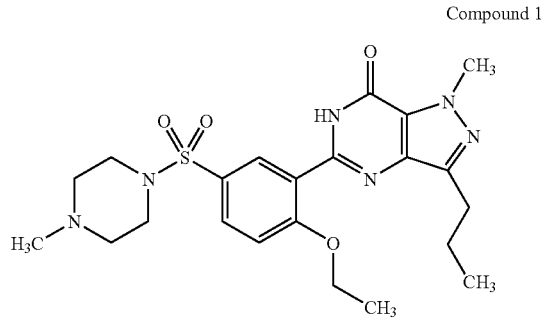

Compound 1

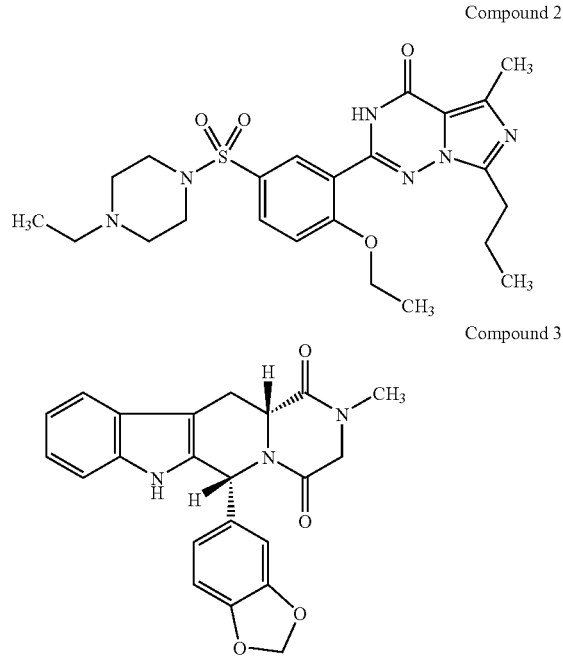

Compound 2

Compound 3

Certain compounds useful in the present invention can be represented by the structure (Formula I):

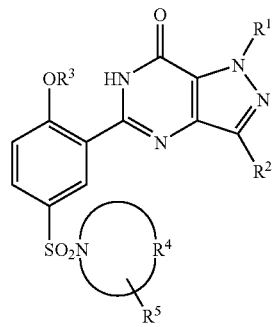

Formula I in which $R^1$ is H, $C_1$-$C_3$ alkyl, $C_3$-$C_5$ cycloalkyl or $C_1$-$C_3$ perfluoroalkyl; $R^2$ is H, $C_1$-$C_6$ alkyl optionally substituted by OH, $C_1$-$C_3$ alkoxy or $C_3$-$C_6$ cycloalkyl, or $C_1$-$C_3$ perfluoroalkyl; $R^3$ is $C_1$-$C_6$ alkyl, $C_3$-$C_6$ alkenyl, $C_3$-$C_6$ alkynyl, $C_3$-$C_{67}$ cycloalkyl, $C_1$-$C_6$ perfluoroalkyl or ($C_3$-$C_6$ cycloalkyl) $C_1$-$C_6$ alkyl; $R^4$ taken together with the nitrogen atom to which it is attached completes a 4-N—($R^6$)-piperazinyl group; $R^5$ is H, $C_1$-$C_4$ alkyl, $C_1$-$C_3$ alkoxy, $NR^7R^8$, or $CONR^7R^8$; $R^8$ is H, $C_1$-$C_6$ alkyl, ($C_1$-$C_3$ alkoxy) $C_2$-$C_6$ alkyl hydroxy $C_2$-$C_6$ alkyl, ($R^7R^8N$) $C_2$-$C_6$ alkyl, ($R^7R^8NCO$) $C_1$-$C_6$ alkyl, $CONR^7R^8$, $CSNR^7R^8$ or $C(NH)N\ R^7R^8$; $R^7$ and $R^8$ are each independently H, $C_1$-$C_4$ alkyl, ($C_1$-$C_3$ alkoxy) $C_2$-$C_4$ alkyl or hydroxy $C_2$-$C_4$ alkyl; and pharmaceutically acceptable salts thereof.

Other preferred compounds for use in the present invention are disclosed in U.S. Pat. No. 6,362,178 and can be represented by the structure (Formula II):

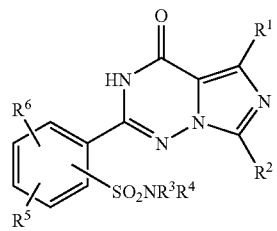

Formula II in which

R¹ represents hydrogen or straight-chain or branched alkyl having up to 4 carbon atoms, R² represents straight-chain alkyl having up to 4 carbon atoms, R³ and R⁴ are identical or different and each represents hydrogen or represents straight-chain or branched alkenyl or alkoxy having in each case up to 8 carbon atoms, or represents a straight-chain or branched alkyl chain having up to 10 carbon atoms which is optionally interrupted by an oxygen atom and which is optionally mono- or polysubstituted by identical or different substituents selected from the group consisting of trifluoromethyl, trifluoromethoxy, hydroxyl, halogen, carboxyl, benzyloxycarbonyl, straight-chain or branched alkoxycarbonyl having up to 6 carbon atoms and/or by radicals of the formulae —SO₃H, -(A)$_a$-NR⁷R⁸, —O—CO—NR⁷R⁸', —S(O)$_b$—R⁹, —P(O)(OR¹⁰)(OR¹¹),

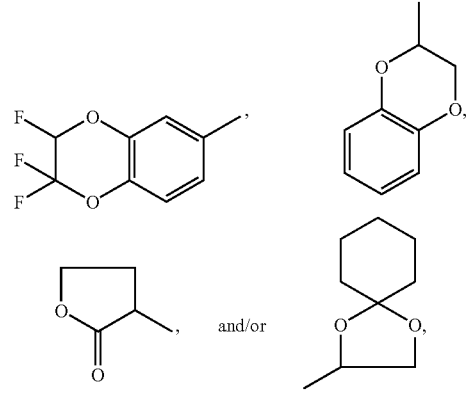

in which a and b are identical or different and each represents a number 0 or 1, A represents a radical CO or SO₂, R⁷, R⁷', R⁸ and R⁸' are identical or different and each represents hydrogen, or represents cycloalkyl having 3 to 8 carbon atoms, aryl having 6 to 10 carbon atoms, a 5- to 6-membered unsaturated, partially unsaturated or saturated, optionally benzo-fused heterocycle having up to 3 heteroatoms from the group consisting of S, N and O, where the abovementioned ring systems are optionally mono- or polysubstituted by identical or different substituents selected from the group consisting of hydroxyl, nitro, trifluoromethyl, trifluoromethoxy, carboxyl, halogen, straight-chain or branched alkoxy or alkoxycarbonyl having in each case up to 6 carbon atoms or by a group of the formula —(SO₂)$_c$—NR¹²R¹³, in which c represents a number 0 or 1, R¹² and R¹³ are identical or different and each represents hydrogen or straight-chain or branched alkyl having up to 5 carbon atoms, or R⁷, R⁷', R⁸ and R⁸' each represent straight-chain or branched alkoxy having up to 6 carbon atoms, or represents straight-chain or branched alkyl having up to 8 carbon atoms which is optionally mono- or polysubstituted by identical or different substituents selected from the group consisting of hydroxyl, halogen, aryl having 6 to 10 carbon atoms, straight-chain or branched alkoxy or alkoxycarbonyl having in each case up to 6 carbon atoms or by a group of the formula —(CO)$_d$—NR¹⁴R¹⁵, in which R¹⁴ and R¹⁵ are identical or different and each represents hydrogen or straight-chain or branched alkyl having up to 4 carbon atoms, and d represents a number 0 or 1, or R⁷ and R⁸ and/or R⁷' and R⁸' together with the nitrogen atom form a 5- to 7-membered saturated heterocycle which may optionally contain a further heteroatom from the group consisting of S and O or a radical of the formula —NR¹⁶, in which R¹⁶ represents hydrogen, aryl having 6 to 10 carbon atoms, benzyl, a 5- to 7-membered aromatic or saturated heterocycle having up to 3 heteroatoms from the group consisting of S, N and O which is optionally substituted by methyl, or represents straight-chain or branched alkyl having up to 6 carbon atoms which is optionally substituted by hydroxyl, R⁹ represents aryl having 6 to 10 carbon atoms, or represents straight-chain or branched alkyl having up to 4 carbon atoms, R¹⁰ and R¹¹ are identical or different and each represents hydrogen or straight-chain or branched alkyl having up to 4 carbon atoms, and/or the alkyl chain listed above under R³/R⁴ is optionally substituted by cycloalkyl having 3 to 8 carbon atoms, aryl having 6 to 10 carbon atoms or by a 5- to 7-membered partially unsaturated, saturated or unsaturated, optionally benzo-fused heterocycle which may contain up to 4 heteroatoms from the group consisting of S, N and O or a radical of the formula —NR¹⁷, in which R¹⁷ represents hydrogen, hydroxyl, formyl, trifluoromethyl, straight-chain or branched acyl or alkoxy having in each case up to 4 carbon atoms, or represents straight-chain or branched alkyl having up to 6 carbon atoms which is optionally mono- or polysubstituted by identical or different substituents selected from the group consisting of hydroxyl and straight-chain or branched alkoxy having up to 6 carbon atoms, and where aryl and the heterocycle are optionally mono- or polysubstituted by identical or different substituents selected from the group consisting of nitro, halogen, —SO₃H, straight-chain or branched alkyl or alkoxy having in each case up to 6 carbon atoms, hydroxyl, trifluoromethyl, trifluoromethoxy and/or by a radical of the formula —SO₂—NR¹⁸R¹⁹, in which R¹⁸ and R¹⁹ are identical or different and each represents hydrogen or straight-chain or branched alkyl having up to 6 carbon atoms, and/or R³ or R⁴ represents a group of the formula —NR²⁰R²¹, in which R²⁰ and R²¹ have the meanings of R¹⁸ and R¹⁹ given above and are identical to or different from them, and/or R³ or R⁴ represents adamantyl, or represents radicals of the formulae

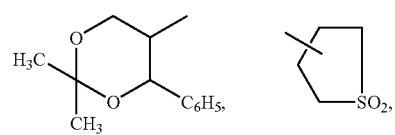

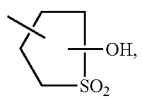 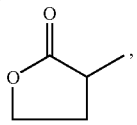

or represents cycloalkyl having 3 to 8 carbon atoms, aryl having 6 to 10 carbon atoms or represents a 5- to 7-membered partially unsaturated, saturated or unsaturated, optionally benzo-fused heterocycle which may contain up to 4 heteroatoms from the group consisting of S, N and O, or a radical of the formula —$NR^{22}$, in which $R^{22}$ has the meaning of $R^{16}$ given above and is identical to or different from it, or represents carboxyl, formyl or straight-chain or branched acyl having up to 5 carbon atoms, and where cycloalkyl, aryl and/or the heterocycle are optionally mono- or polysubstituted by identical or different substituents selected from the group consisting of halogen, triazolyl, trifluoromethyl, trifluoromethoxy, carboxyl, straight-chain or branched acyl or alkoxycarbonyl having in each case up to 6 carbon atoms, nitro and/or by groups of the formulae —$SO_3H$, —$OR^{23}$, $(SO_2)_e NR^{24}R^{25}$, —$P(O)(OR^{26})(OR^{27})$ in which e represents a number 0 or 1, $R^{23}$ represents a radical of the formula

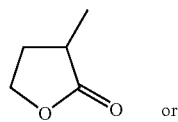

represents cycloalkyl having 3 to 7 carbon atoms, or represents hydrogen or straight-chain or branched alkyl having up to 4 carbon atoms which is optionally substituted by cycloalkyl having 3 to 7 carbon atoms, benzyloxy, tetrahydropyranyl, tetrahydrofuranyl, straight-chain or branched alkoxy or alkoxycarbonyl having in each case up to 6 carbon atoms, carboxyl, benzyloxycarbonyl or phenyl which for its part may be mono- or polysubstituted by identical or different substituents selected from the group consisting of straight-chain or branched alkoxy having up to 4 carbon atoms, hydroxyl and halogen, and/or alkyl which is optionally substituted by radicals of the formulae —CO—$NR^{28}R^{29}$ or —CO—$R^{30}$, in which $R^{28}$ and $R^{29}$ are identical or different and each represents hydrogen or straight-chain or branched alkyl having up to 8 carbon atoms, or $R^{28}$ and $R^{29}$ together with the nitrogen atom form a 5- to 7-membered saturated heterocycle which may optionally contain a further heteroatom from the group consisting of S and O, and $R^{30}$ represents phenyl or adamantyl, $R^{24}$ and $R^{25}$ have the meanings of $R^{18}$ and $R^{19}$ given above and are identical to or different from them, $R^{26}$ and $R^{27}$ have the meanings of $R^{10}$ and $R^{11}$ given above and are identical to or different from them and/or cycloalkyl, aryl and/or the heterocycle are optionally substituted by straight-chain or branched alkyl having up to 6 carbon atoms which is optionally substituted by hydroxyl, carboxyl, by a 5- to 7-membered heterocycle having up to 3 heteroatoms from the group consisting of S, N and O, or by groups of the formula —$SO_2$—$R^{31}$, $P(O)(OR^{32})(OR^{33})$ or —$NR^{34}R^{35}$, in which $R^{31}$ represents hydrogen or has the meaning of $R^9$ given above and is identical to or different from it, $R^{32}$ and $R^{33}$ have the meanings of $R^{10}$ and $R^{11}$ given above and are identical to or different from them, $R^{34}$ and $R^{35}$ are identical or different and each represents hydrogen or straight-chain or branched alkyl having up to 6 carbon atoms which is optionally substituted by hydroxyl or by straight-chain or branched alkoxy having up to 4 carbon atoms, or $R^{34}$ and $R^{35}$ together with the nitrogen atom form a 5- to 6-membered saturated heterocycle which may contain a further heteroatom from the group consisting of S and O, or a radical of the formula —$NR^{36}$, in which $R^{36}$ represents hydrogen, hydroxyl, straight-chain or branched alkoxycarbonyl having up to 7 carbon atoms or straight-chain or branched alkyl having up to 5 carbon atoms which is optionally substituted by hydroxyl, or $R^3$ and $R^4$ together with the nitrogen atom form a 5- to 7-membered unsaturated or saturated or partially unsaturated, optionally benzo-fused heterocycle which may optionally contain up to 3 heteroatoms from the group consisting of S, N and O, or a radical of the formula —$NR^{37}$, in which $R^{37}$ represents hydrogen, hydroxyl, formyl, trifluoromethyl, straight-chain or branched acyl, alkoxy or alkoxycarbonyl having in each case up to 4 carbon atoms, or represents straight-chain or branched alkyl having up to 6 carbon atoms which is optionally mono- or polysubstituted by identical or different substituents selected from the group consisting of hydroxyl, trifluoromethyl, carboxyl, straight-chain or branched alkoxy or alkoxycarbonyl having in each case up to 6 carbon atoms, or by groups of the formula -$(D)_f$-$NR^{38}R^{39}$, —CO—$(CH_2)_g$—O—CO—$R^{40}$, —CO—$(CH_2)_h$—$OR^{41}$ or —$P(O)(OR^{42})(OR^{43})$, in which g and h are identical or different and each represents a number 1, 2, 3 or 4, and f represents a number 0 or 1, D represents a group of the formula —CO or —$SO_2$, $R^{38}$ and $R^{39}$ are identical or different and each has the meaning of $R^7$ and $R^8$ given above, $R^{40}$ represents straight-chain or branched alkyl having up to 6 carbon atoms, $R^{41}$ represents straight-chain or branched alkyl having up to 6 carbon atoms, $R^{42}$ and $R^{43}$ are identical or different and each represents hydrogen or straight-chain or branched alkyl having up to 4 carbon atoms, or $R^{37}$ represents a radical of the formula —$(CO)_i$-E, in which i represents a number 0 or 1, E represents cycloalkyl having 3 to 7 carbon atoms or benzyl, represents aryl having 6 to 10 carbon atoms or a 5- to 6-membered aromatic heterocycle having up to 4 heteroatoms from the group consisting of S, N and O, where the abovementioned ring systems are optionally mono- or polysubstituted by identical or different constituents selected from the group consisting of nitro, halogen, —$SO_3H$, straight-chain or branched alkoxy having up to 6 carbon atoms, hydroxyl, trifluoromethyl, trifluoromethoxy, or by a radical of the formula —$SO_2$—$NR^{44}R^{45}$, in which $R^{44}$ and $R^{45}$ have the meaning of $R^{18}$ and $R^{19}$ given above and are identical to or different from them, or E represents radicals of the formulae

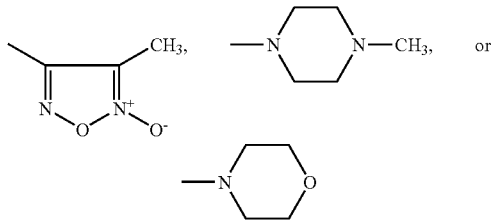

and the heterocycle listed under $R^3$ and $R^4$, which is formed together with the nitrogen atom, is optionally mono- or polysubstituted, if appropriate also geminally, by identical or different substituents selected from the group consisting of hydroxyl, formyl, carboxyl, straight-chain or branched acyl or alkoxycarbonyl having in each case up to 6 carbon atoms, nitro and groups of the formulae —P(O)(OR$^{46}$)(OR$^{47}$),

=NR$^{48}$, or —C(O)$_j$NR$^{49}$R$^{50}$,
in which $R^{46}$ and $R^{47}$ have the meanings of $R^{10}$ and $R^{11}$ given above and are identical to or different from them, $R^{48}$ represents hydroxyl or straight-chain or branched alkyl having up to 4 carbon atoms, j represents a number 0 or 1, and $R^{49}$ and $R^{50}$ are identical or different and have the meanings of $R^{14}$ and $R^{15}$ given above, a nd/or the heterocycle listed under $R^3$ and $R^4$, which is formed together with the nitrogen atom, is optionally substituted by straight-chain or branched alkyl having up to 6 carbon atoms which is optionally mono- or polysubstituted by identical or different substituents selected from the group consisting of hydroxyl, halogen, carboxyl, cycloalkyl or cycloalkyloxy having in each case 3 to 8 carbon atoms, straight-chain or branched alkoxy or alkoxycarbonyl having in each case up to 6 carbon atoms, or by a radical of the formula —SO$_3$H, —NR$^{51}$R$^{52}$ or P(O)OR$^{53}$OR$^{54}$, in which $R^{51}$ and $R^{52}$ are identical or different and each represents hydrogen, phenyl, carboxyl, benzyl or straight-chain or branched alkyl or alkoxy having in each case up to 6 carbon atoms, $R^{53}$ and $R^{54}$ are identical or different and have the meanings of $R^{10}$ and $R^{11}$ given above, and/or the alkyl is optionally substituted by aryl having 6 to 10 carbon atoms which for its part may be mono- or polysubstituted by identical or different substituents selected from the group consisting of halogen, hydroxyl, straight-chain or branched alkoxy having up to 6 carbon atoms, or by a group of the formula —NR$^{51'}$R$^{52'}$, in which $R^{51'}$ and $R^{52'}$ have the meanings of $R^{51'}$ and $R^{52'}$ given above and are identical to or different from them, and/or the heterocycle listed under $R^3$ and $R^4$, which is formed together with the nitrogen atom, is optionally substituted by aryl having 6 to 10 carbon atoms or by a 5- to 7-membered saturated, partially unsaturated or unsaturated heterocycle having up to 3 heteroatoms from the group consisting of S, N and O, optionally also attached via a nitrogen function, where the ring systems for their part may be substituted by hydroxyl or by straight-chain or branched alkyl or alkoxy having in each case up to 6 carbon atoms, or $R^3$ and $R^4$ together with the nitrogen atom form radicals of the formulae

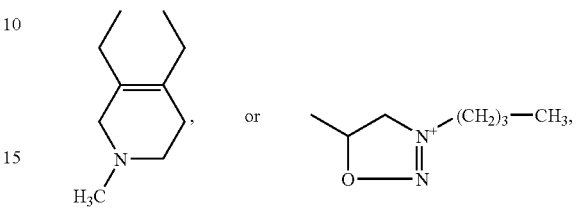

$R^5$ and $R^6$ are identical or different and each represents hydrogen, straight-chain or branched alkyl having up to 6 carbon atoms, hydroxyl or represents straight-chain or branched alkoxy having up to 6 carbon atoms, and their salts, hydrates, N-oxides and structural isomers.

Other suitable compounds include those of the following Formula III:

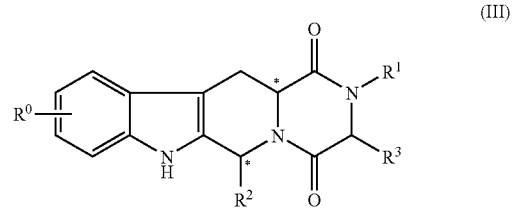

(III)

wherein in Formula III, $R^0$ represents hydrogen, halogen, or C$_{1-6}$ alkyl;

$R^1$ represents hydrogen, C$_{1-6}$ alkyl, C$_{2-6}$ alkenyl, C$_{2-6}$ alkynyl, haloC$_{1-6}$ alkyl, C$_{3-8}$ cycloalkyl, C$_{3-8}$ cycloalkylC$_{1-3}$ alkyl, arylC$_{1-3}$ alkyl, or heteroarylC$_{1-3}$ alkyl;

$R^2$ represents an optionally substituted monocyclic aromatic ring selected from benzene, thiophene, furan, and pyridine, or an optionally substituted bicyclic ring;

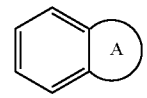

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen; and $R^3$ represents hydrogen of C$_{1-3}$ alkyl, or $R^1$ and $R^3$ together represent a 3- or 4-membered alkyl or alkenyl chain; and pharmaceutically and salts and solvates (e.g., hydrates) thereof.

Certain preferred compounds also include those of the following Formula IV:

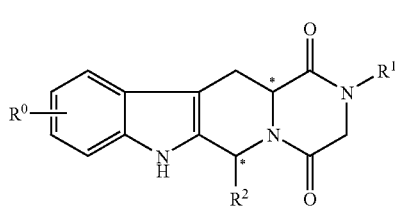

wherein in Formula IV, $R^0$ represents hydrogen, halogen, or $C_{1-6}$ alkyl;
$R^1$ represents hydrogen, $C_{1-6}$ alkyl, halo$C_{1-6}$ alkyl, $C_{3-8}$ cycloalkyl$C_{1-3}$ alkyl, aryl$C_{1-3}$ alkyl, or heteroaryl$C_{1-3}$ alkyl; and
$R^2$ represents an optionally substituted monocyclic aromatic ring selected from benzene, thiophene, furan, and pyridine, or an optionally substituted bicyclic ring

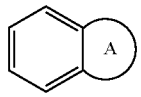

attached to the rest of the molecule via one of the benzene ring carbon atoms, and wherein the fused ring A is a 5- or 6-membered ring which can be saturated or partially or fully unsaturated and comprises carbon atoms and optionally one or two heteroatoms selected from oxygen, sulphur, and nitrogen; and pharmaceutically acceptable salts and solvates (e.g., hydrates) thereof.

A further group of compounds preferred for use in the invention are compounds of the following Formula V:

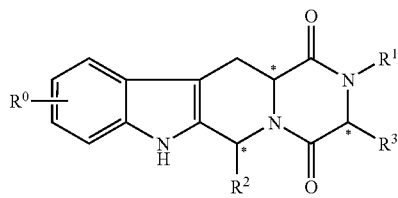

wherein in Formula V:
$R^0$ represents hydrogen, halogen, or $C_{1-6}$ alkyl;
$R^1$ represents hydrogen or $C_{1-6}$ alkyl
$R^2$ represents the bicyclic ring

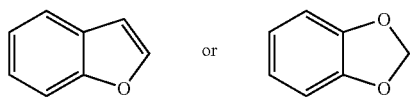

which can be optionally substituted by one or more groups selected from halogen and $C_{1-3}$ alkyl; and
$R^3$ represents hydrogen or $C_{1-3}$ alkyl; and pharmaceutically acceptable salts and solvates (e.g., hydrates) thereof.
In Formula IV above, with respect to $R^1$, the term "aryl" as part of an aryl$C_{1-3}$ alkyl group means phenyl or phenyl substituted by one or more (e.g., 1, 2, or 3) substituents selected from halogen, $C_{1-6}$ alkyl, $C_{1-6}$ alkoxy, and methylenedioxy.

The term "heteroaryl" as part of a heteroaryl$C_{1-3}$ alkyl group means thienyl, furyl, or pyridyl, each optionally substituted by one or more (e.g., 1, 2, or 3) substituents selected from halogen, $C_{1-6}$ alkyl, and $C_{1-6}$ alkoxy. The term "$C_{3-8}$ cycloalkyl" as a group or part of a $C_{3-8}$ cycloalkyl$C_{1-3}$ alkyl group means a monocyclic ring comprising three to eight carbon atoms. Examples of suitable cycloalkyl rings include the $C_{3-6}$ cycloalkyl rings cyclopropyl, cyclobutyl, cyclopentyl, and cyclohexyl.

In formula IV above, with respect to $R^2$, optional benzene ring substituents are selected from one or more (e.g., 1, 2, or 3) atoms or groups comprising halogen, hydroxy, $C_{1-6}$ alkyl, $C_{1-6}$ alkoxy, $CO_2R^b$, halo$C_{1-6}$ alkyl, halo$C_{1-6}$ alkoxy, cyano, nitro, and $NR^aR^b$, where $R^a$ and $R^b$ are each hydrogen or $C_{1-6}$ alkyl, or $R^a$ also can represent $C_{2-7}$ alkanoyl or $C_{1-6}$ alkylsulphonyl. Optional substituents for the remaining ring systems are selected from one or more (e.g., 1, 2, or 3 atoms or groups comprising halogen, $C_{1-6}$ alkyl, $C_{1-6}$ alkoxy, and aryl$C_{1-3}$ alkyl as defined above. The bicyclic ring

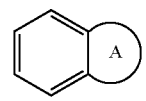

can, for example, represent naphthalene, a heterocycle such as benzoxazole, benzothiazole, benzisoxazole, benzimidazole, quinoline, indole, benzothiophene, benzofuran, or

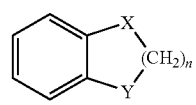

wherein n is an integer 1 or 2 and X and Y each can represent $CH_2$, O, S, or NH.

See also U.S. Pat. Nos. 6,916,927, 6,911,542, 6,903,099, 6,878,711, 6,872,721, 6,858,620, 6,825,197, 6,774,128, 6,723,719, 6,699,870, 6,670,366, 5,859,006 and 5,250,534. Other PDE5 inhibitors useful in the methods of the invention are described in WO 03/063875; WO 03/1012761 WO 2004/037183, and WO 98/38168. All of these patents and patent applications are incorporated herein by reference in their entirety.

Sildenafil is commercially available in three dosages of 25, 50, or 100 mg and has an $IC_{50}$ of approximately 10 nM. Effective plasma concentrations are between 1 nM and 250 nM, where the bottom of the range is any integer between 1 and 249; and the top of the range is any integer between 2 nM and 250 nM. Preferably, an effective plasma concentration is between 5 nM and 100 nM, more preferably it is between 10 nM and 50 nM (e.g., 15 nM, 20 nM, 25 nM, 30 nM, 40 nM, or 45 nM).

Tadalafil is commercially available in three dosages of 5, 10, or 20 mg and has an $IC_{50}$ of approximately 1 nM. Following oral administration of a 20 mg dose of tadalafil to healthy subjects, tadalafil is rapidly absorbed with the peak plasma concentration of 378 ng/ml occurring two hours post-dose. Preferably an effective plasma concentration is between 5 nM and 100 nM, more preferably it is between 10 nM and 50 nM (e.g., 15 nM, 20 nM, 25 nM, 30 nM, 40 nM, or 45 nM). Tadalafil has a relative large apparent volume of distribution (Vd/F) of 62.6 L, and a low apparent oral clearance (CL/F) of 2.48 L/h. As a result, the mean elimination half-life of tadalafil is about 17.5 h, which is substantially longer than that of sildenafil or vardenafil.

Vardenafil is commercially available in three dosages of 5 mg, 10 mg, and 20 mg and has an $IC_{50}$ of 0.7 nM. Effective plasma concentrations of vardenafil are between 0.1 and 5.0 nM.

The skilled artisan appreciates that any compound that reduces the activity of PDE5 is useful in the methods of the invention. Other exemplary compounds useful in the methods of the invention include UK-343,664 (Walker et al., Xenobiotica, 31: 651-664), UK-427,387, UK-357903 [1-ethyl-4-{3-[3-ethyl-6,7-dihydro-7-oxo-2-(2-pyridylmethyl)-2H-pyrazolo[4,3-d]pyrimidin-5-yl]-2-(2-methoxyethoxy)-5-pyridylsulphonyl}piperazine] (Gardiner et al. *J Pharmacol Exp Ther.* 2005; 312: 265-271), UK-371800 (Pfizer), UK-313794 (Pfizer) and UK-343664 (Abel et al., Xenobiotica. 2001 31:665-76); TA-1790 from Tanabe Seiyaku; CP-248, CP-461 and exisulind (Degucli et al., Molecular Cancer Therapeutics 803-809, 2002), which are available from Osi Pharmaceuticals; pyrazolinone; EMD82639 (4-(4-[2-ethyl-phenylamino)-methylene]-3-methyl-5-oxo-4,5-dihydro-pyrazol-1-yl)-benzoic acid (Senzaki et al., FASEB Journal. 2001; 15:1718-1726); [7-(3-Chloro-4-methoxy-benzylamino)-1-methyl-3-propyl-1H-pyrazolo[4,3-d]pyrimidin-5-ylmethoxy]-acetic acid (EMD360527), 4-[4-(3-Chloro-4-methoxy-benzylamino)-benzo[4,5]thieno[2,3-d]-pyrimidin-2-yl]-cyclohexanecarboxylic acid, ethanolamin salt (EMD221829) and 5-[4-(3-Chloro-4-methoxy-benzylamino)-5,6,7,8-tetrahydro-benzo[4,5]thieno[2,3-d]pyrimidin-2-yl]-pentanoic acid (EMD171827), which are commercially available from Merck KgaA (Darmstadt, Del.) and are described, for example, in Scutt et al. (BMC Pharmacol. 2004; 4: 10); 3-(1-Methyl-7-oxo-3-propyl-6,7-dihydro-1H-pyrazolo-[4,3-d]pyrimidin-5-yl)-N-[2-(1-methylpyrrolidin-2-yl)ethyl]-4-propoxybenzenesulfonamide (DA-8259); E-4021 (Dukarm et al., Am. J. Respir. Crit. Care Med., 1999, 160:858-865); pentoxifylline and FR22934 (Fujisawa).

Pharmaceutical Compositions

The present invention features pharmaceutical preparations comprising a PDE5A inhibitor (e.g., sildenafil, vardenafil, tadalafil, or analogs thereof) together with pharmaceutically acceptable carriers, where the compounds provide for the treatment of virtually any cardiac indication characterized by the hypertrophic morphological, cellular, or molecular remodeling of a cardiac tissue. Pharmaceutical preparations of the invention have both therapeutic and prophylactic applications. In one embodiment, a pharmaceutical composition includes an effective amount of a PDE5 inhibitor. The compositions should be sterile and contain a therapeutically effective amount of a PDE5 inhibitor in a unit of weight or volume suitable for administration to a subject (e.g., a human patient). The compositions and combinations of the invention can be part of a pharmaceutical pack, where the PDE5 inhibitor is present in individual dosage amounts.

Pharmaceutical compositions of the invention to be used for prophylactic or therapeutic administration should be sterile. Sterility is readily accomplished by filtration through sterile filtration membranes (e.g., 0.2 μm membranes), by gamma irradiation, or any other suitable means known to those skilled in the art. Therapeutic compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

A PDE5 inhibitor may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with a PDE5 inhibitor of the present invention, and with each other, in a manner such that there is no interaction that would substantially impair the desired pharmaceutical efficacy.

Compounds of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a cardiac disease or disorder associated with hypertrophic morphological, cellular, or molecular remodeling, an effective amount is sufficient to prevent, reduce, stabilize, or reverse an alteration associated with cardiac hypertrophy. With respect to a subject having a cardiac disease or disorder, an effective amount is an amount sufficient to stabilize, slow, or reduce a symptom associated with the cardiac condition. Generally, doses of the compounds of the present invention would be from about 0.01 mg/kg per day to about 1000 mg/kg per day. In one embodiment, 25, 50, 75, 100, 125, 150 or 200 mg of a PDE5 inhibitor, such as sildenafil, is administered to a subject. Preferably, 100 mg of a PDE5 inhibitor is administered. Desirably, the PDE5 inhibitor is administered in an amount sufficient to achieve a peak concentration of 10, 25, 50, 75, or 100 nM in plasma. Preferably, the peak concentration is 50 nM. Effective doses range from 0.1 nM to 200 nM, where the bottom of the range is any integer between 1 and 199, and the top of the range is any integer between 2 and 200. Desirably, an effective dose results in a free plasma PDE5 inhibitor concentration ranging from 10-50 nM; but it can be as much as 200 nM or as low as 1-2 nM. Exemplary concentrations include 0.1, 1, 5, 10, 20, 25, 30, 40, or 50 nM. It is expected that doses ranging from about 5 to about 2000 mg/kg will be suitable—depending on the specific PDE5a inhibitor used. Lower doses will result from certain forms of administration, such as intravenous administration and pharmaceutical. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one preferred embodiment, a composition of the invention is administered orally. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising a compound of the present invention can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least −70° C., but can also be stored at higher temperatures of at least 0° C., or between about 0.1° C. and about 42° C., depending on the properties of the composition. It is generally known to the skilled artisan that proteins and polypeptides are sensitive to changes in pH, temperature, and a multiplicity of other factors that may affect therapeutic efficacy.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 μm, can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications, for example, in DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into a mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly (ortho)esters, poly(butic acid), poly(valeric acid), and poly (lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Methods of Treatment

In one embodiment, the present invention provides a method of inhibiting PDE5 in the heart of a subject comprising the step of administering to the subject an effective amount of a PDE5 inhibitor, preferably as part of a composition additionally comprising a pharmaceutically acceptable carrier. Preferably this method is employed to treat a subject suffering from or susceptible to a cardiac condition selected from cardiac hypertrophy, reduced systolic function, reduced diastolic function, maladaptive hypertrophy, heart failure with preserved systolic function, diastolic heart failure, hypertensive heart disease, aortic stenosis, hypertrophic cardiomyopathy, post ischemic cardiac remodeling and cardiac failure. Other embodiments include any of the methods herein wherein the subject is identified as in need of the indicated treatment.

Another aspect of the invention is the use of a PDE5 inhibitor in the manufacture of a medicament for enhancing cardiac function or reducing morphological, cellular, or molecular remodeling in a subject. Preferably, the medicament is used for treatment or prevention in a subject of a disease, disorder or symptom set forth above.

Kits

The invention provides kits for the treatment or prevention of a cardiac condition associated with cardiac hypertrophy, including morphological, cellular, or molecular remodeling. In one embodiment, the kit includes a pharmaceutical pack comprising an effective amount of a PDE5 inhibitor (e.g., a PDE5a inhibitor, such as sildenafil). Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject having or at risk of developing a cardiac condition associated with hypertrophy. The instructions will generally include information about the use of the compounds for the treatment or prevention of a cardiac condition associated with hypertrophy. In other embodiments, the instructions include at least one of the following: description of the compound or combination of compounds; dosage schedule and administration for treatment of a cardiac condition or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The following examples are provided to illustrate the invention, not to limit it. Those skilled in the art will understand that the specific constructions provided below may be changed in numerous ways, consistent with the above described invention while retaining the critical properties of the compounds or combinations thereof.

EXAMPLES

Example 1

PDE5A-Inhibition Blunts Cardiac Hypertrophy, Remodeling, and Fibrosis

Adult C57BL6 mice were subjected to constriction of the chronic pressure overload induced by transverse aorta constriction (TAC) for 1-9 weeks or to sham-surgery, and then treated concurrently with the PDE5A inhibitor sildenafil (100 mg/kg/day) or a vehicle mixed in solid food. TAC induced marked heart chamber and cellular hypertrophy (+100% by 3-weeks) that progressed to chamber dilation with reduced fractional shortening after 9 weeks. Both the hypertrophy and chamber remodeling were inhibited by the PDE5A inhibitor, sildenafil, in TAC animals (FIGS. 1A and 1B), whereas sildenafil had no impact on sham-operated controls. Free plasma sildenafil concentration averaged ~10 nM (FIG. 2), well within the range specific for PDE5A and similar to that achieved using standard clinical dosing. TAC induced a time-dependent increase in myocardial fibrosis and myocyte hypertrophy and both were suppressed by PDE5A inhibition (FIG. 1C, e.g. 67% reduction in fibrosis in 9-week hearts, $p<0.0001$). This effect was achieved at pharmacologically appropriate doses (FIG. 2). At the 100 mg/kg/day oral dose, a free plasma sildenafil concentration of 10 nM was obtained. Separate studies performed using an alternative highly selective PDE5A inhibitor (EMD 360527) yielded identical findings (FIG. 5A) supporting a drug class effect.

Example 2

PDE5A-Inhibition Reverses Established Hypertrophy

Figure 3:
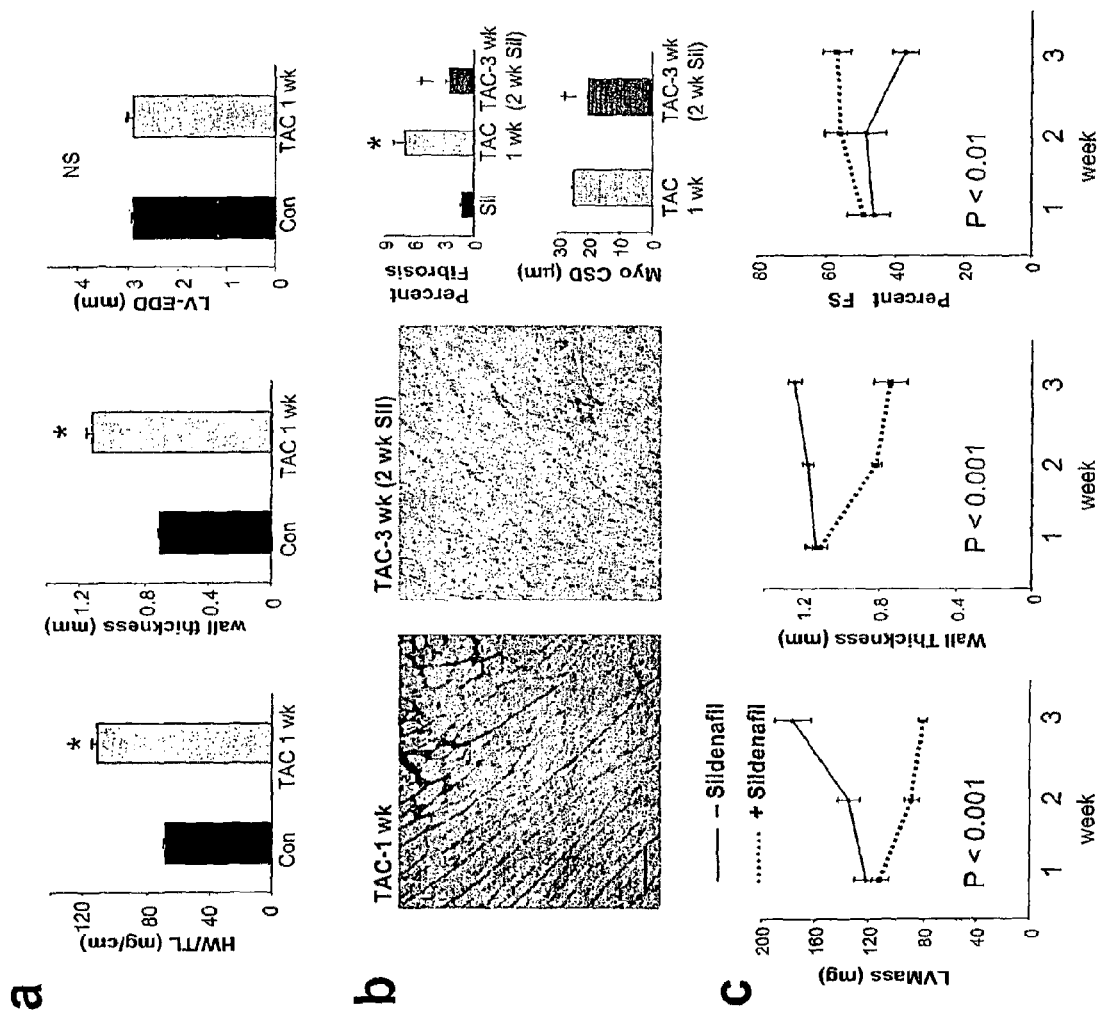
FIGS. 3A-3C show that inhibition of PDE5A with sildenafil reverses established cardiac hypertrophy.

The more clinically applicable question of whether PDE5A-inhibition could reverse already existing hypertrophy was tested. Mice were exposed to TAC for 7-10 days which increased heart mass by 63% ($p<0.005$) without chamber dilation (FIG. 3A). The animals were then divided into two groups, one that received sildenafil for an additional 2 weeks, and a control group receiving vehicle only. Myocyte hypertrophy and interstitial fibrosis were observed with 1-week TAC and both reversed towards baseline with sildenafil treatment (FIG. 3B). Serial echocardiography showed a gradual decline in LV mass and wall thickness, with preservation of systolic ejection in sildenafil-treated animals (FIG. 3C).

Example 3

Cardiac Function is Enhanced Despite Sustained Afterload

Figure 4:
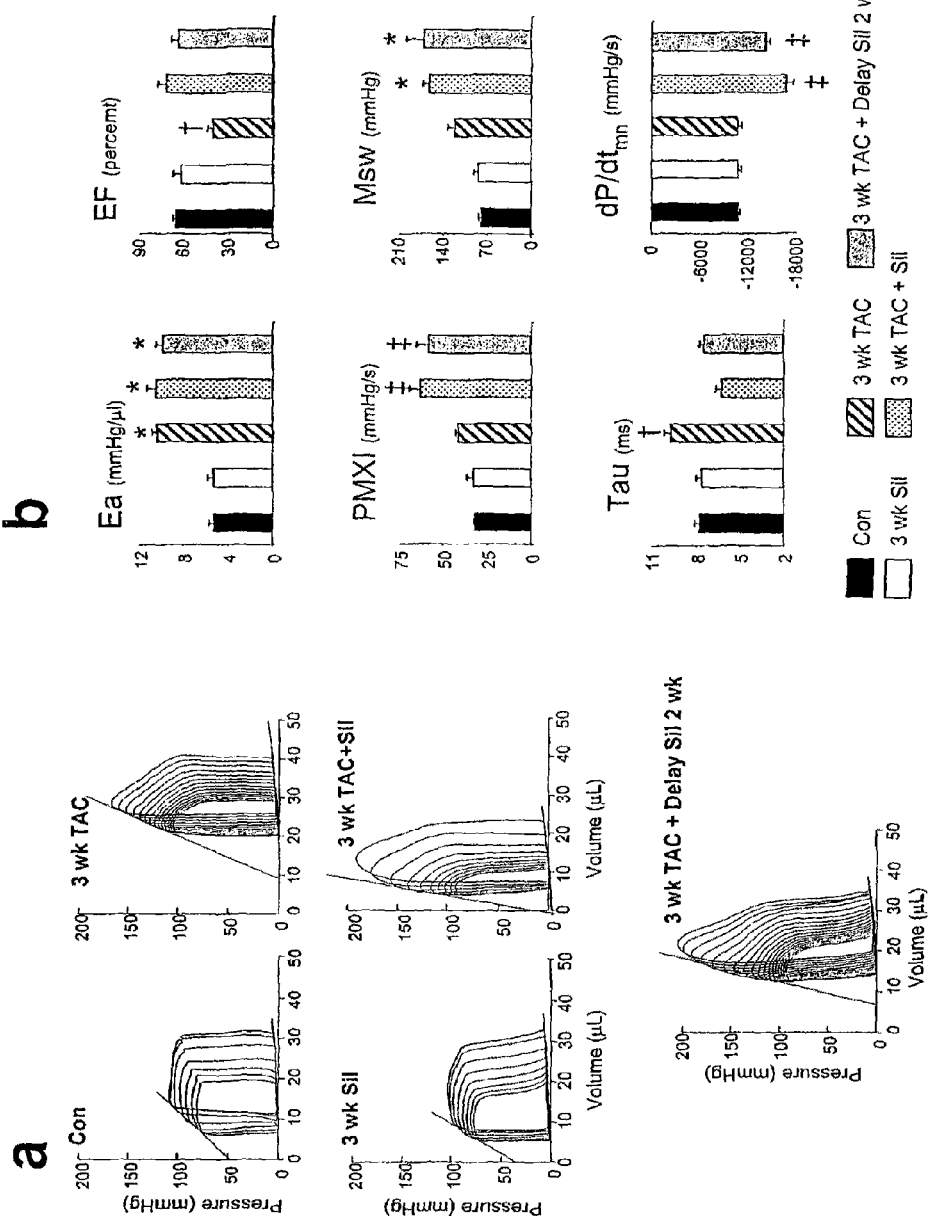
FIG. 4). *$p<0.05$ vs Con and EMD; †$p<0.05$ vs all other groups.

Detailed examination of heart function was performed by invasive pressure-volume (PV) analysis. FIG. 4A shows PV loops measured before and during transient reduction of chamber preload to generate specific systolic and diastolic function indexes. As shown by the examples, PV loops and corresponding systolic and diastolic boundary relations shifted rightward with TAC (3 weeks)—consistent with chamber remodeling. Co-treatment with sildenafil resulted in preservation of cardiac volumes and an increase in systolic function (e.g. slope of end-systolic pressure-volume relation, solid line). Sham controls similarly treated for 3 weeks displayed no change. Cardiac function also improved when sildenafil was administered after hypertrophy was already established. Thus, PDE5 inhibitor treatment prevented or reversed alterations in cardiac function associated with cardiac hypertrophy.

Summary results from this analysis are shown in FIG. 4B. Ventricular afterload (indexed by Ea) was identically elevated by TAC regardless of treatment, yet only vehicle-treated TAC animals showed a decline in ejection fraction (EF). Contractile function assessed by load-independent parameters (maximal power index: PMXI, and preload recruitable stroke work: Msw) was restored or improved by sildenafil over control and TAC-only hearts, and similar results were observed for diastolic function (tau, and peak rate of pressure fall—$dP/dt_{min}$). Additional functional and echocardiographic data are provided in Tables 1 and 2, below.

TABLE 1

Effect of sildenafil treatment on serial echocardiographic measurements of left ventricular structure and function in conscious mice.

|  |  | Control | TAC-3 wks | TAC-6 wks | TAC-9 wks |
|---|---|---|---|---|---|
| Treated Vehicle |  | n = 7 | n = 12 | n = 7 | n = 8 |
| Wall Thickness | mm | 0.69 ± 0.05 | 1.24 ± 0.03† | 0.90 ± 0.03†‡ | 0.90 ± 0.05†‡ |
| LV Dim (dia) | mm | 2.85 ± 0.05 | 3.40 ± 0.14 | 4.94 ± 0.23†‡ | 5.16 ± 0.36†‡ |
| LV Dim (sys) | mm | 0.92 ± 0.01 | 2.18 ± 0.21† | 3.98 ± 0.36†‡ | 4.31 ± 0.49†‡ |
| LV Mass | mg | 55.4 ± 1.5 | 175.7 ± 13.5† | 195.3 ± 9.3† | 208.3 ± 14.1† |
| EF | % | 96.6 ± 0.2 | 70.9 ± 4.7† | 45.3 ± 7.3†‡ | 41.3 ± 8.0†‡ |
| HR | min$^{-1}$ | 631 ± 21 | 631 ± 15 | 610 ± 23 | 531 ± 33† |
| Sildenafil Treated |  | n = 9 | n = 18 | n = 7 | n = 7 |
| Wall Thickness | mm | 0.71 ± 0.02 | 0.82 ± 0.02*† | 0.86 ± 0.03† | 0.86 ± 0.03† |
| LV Dim (dia) | mm | 2.87 ± 0.09 | 3.09 ± 0.06* | 3.67 ± 0.24*† | 4.14 ± 0.36*†‡ |
| LV Dim (sys) | mm | 0.89 ± 0.05 | 1.17 ± 0.08* | 2.24 ± 0.37*†‡ | 2.54 ± 0.57*†‡ |
| LV Mass | mg | 59.1 ± 5.6 | 82.2 ± 5.0* | 115.6 ± 14.2*† | 142.5 ± 21.5*†‡ |
| EF | % | 96.5 ± 0.2 | 93.4 ± 1.1* | 74.9 ± 7.1*†‡ | 71.7 ± 9.9*†‡ |
| HR | min$^{-1}$ | 634 ± 9 | 595 ± 7 | 617 ± 18 | 608 ± 25 |

Data are mean ± sem.

LV Dim (LV short axis dimension), dia—diastole;

sys—systole.

LV Mass - estimated LV mass based on truncated ellipsoid model;

EF—ejection fraction;

HR—heart rate.

*p < 0.05 vs vehicle treated;

†p < 0.05 vs control;

‡p < 0.05 vs TAC-3 wks.

TABLE 2

Effect of sildenafil treatment with and without TAC on in vivo cardiac hemodynamics obtained by pressure-volume analysis.

|  |  | Control n = 5 | Sildenafil 3 wk n = 5 | 3 wk TAC n = 6 | 3 wkTAC + Sil n = 5 | 3 wk TAC + Delay(2 wk)Sil n = 4 | ANOVA |
|---|---|---|---|---|---|---|---|
| HR | MIN$^{-}$ | 522.6 ± 13.7 | 558.5 ± 22.9 | 520.0 ± 12.9 (a) | 598.8 ± 23.8 | 574.6 ± 21.7 | 0.032 |
| ESP | mmHg | 102.0 ± 2.0 | 101.5 ± 2.6 | 159.6 ± 4.6 (b) | 163.6 ± 5.6 (b) | 184.0 ± 9.1 (b) | <0.0001 |
| EDP | mmHg | 5.4 ± 1.0 | 6.5 ± 1.0 | 7.1 ± 1.4 | 7.6 ± 1.4 | 7.5 ± 0.6 | NS |
| Ea | mmHg/μL | 5.5 ± 0.4 | 5.3 ± 0.5 | 10.4 ± 0.5 (b) | 10.5 ± 0.8 (b) | 9.9 ± 0.6 (b) | <0.0001 |
| EDV | μL | 29.0 ± 2.0 | 32.8 ± 2.3 | 38.8 ± 3.4 (c) | 22.2 ± 1.5 | 29.4 ± 2.0 | <0.001 |
| ESV | μL | 10.2 ± 1.0 | 13.0 ± 2.7 | 23.3 ± 3.3 (d) | 6.4 ± 1.7 | 10.9 ± 2.1 | <0.0005 |
| EF | % | 65.1 ± 2.1 | 61.4 ± 6.1 | 41.3 ± 3.5 (d) | 72.6 ± 5.7 | 64.0 ± 4.7 | 0.001 |
| CO | mL/min | 9.9 ± 0.7 | 11.1 ± 1.1 | 8.0 ± 0.3 (e) | 9.4 ± 0.5 | 10.7 ± 0.5 | 0.026 |
| dP/dt$_{max}$ | mmHg/s | 13368 ± 370 | 11843 ± 681 | 12602 ± 620 | 18638 ± 1379 (f) | 14879 ± 898 | <0.001 |
| dP/dt$_{mx}$/IP | sec$^{-1}$ | 205.1 ± 6.6 | 183.7 ± 6.9 | 192.2 ± 6.9 | 256.5 ± 8.4 (g) | 209.4 ± 11.1 | <0.001 |
| PMXI | mmHg/s | 31.6 ± 0.9 | 32.7 ± 3.5 | 41.5 ± 1.9 | 63.0 ± 6.7 (h) | 58.6 ± 7.1 (i) | <0.0005 |
| Msw | mmHg | 79.4 ± 4.1 | 84.0 ± 5.7 | 120.8 ± 12.6 | 162.5 ± 10.5 (i) | 171.3 ± 27.6 (i) | <0.0001 |
| Ees$_n$ | mmHg/μL/g | 37.9 ± 5.8 | 47.6 ± 5.8 | 70.2 ± 13.4 | 133.0 ± 25.1 (i) | 111.0 ± 31.4 | <0.005 |
| Tau | Msec | 7.8 ± 0.3 | 7.6 ± 0.4 | 9.7 ± 0.5 (d) | 6.3 ± 0.4 | 7.5 ± 0.3 | <0.0001 |

TABLE 2-continued

Effect of sildenafil treatment with and without TAC on in vivo cardiac hemodynamics obtained by pressure-volume analysis.

|  |  | Control n = 5 | Sildenafil 3 wk n = 5 | 3 wk TAC n = 6 | 3 wkTAC + Sil n = 5 | 3 wk TAC + Delay(2 wk)Sil n = 4 | ANOVA |
|---|---|---|---|---|---|---|---|
| $dP/dt_{min}$ | mmHg/s | −10728 ± 236 | −10689 ± 399 | −10508 ± 500 | −16758 ± 917 (f) | −14325 ± 445 (j) | <0.001 |
| PFR/EDV | $sec^{-1}$ | 37.1 ± 5.6 | 34.1 ± 1.9 | 24.4 ± 1.4 | 43.1 ± 4.9 (k) | 30.6 ± 3.6 | 0.014 |

Table 2 Legend:
Data are mean ± sem.
HR—heart rate;
ESP—LV end-systolic pressure;
EDP—LV end-diastolic pressure;
Ea—effective arterial elastance[1] - an index of total ventricular afterload;
EDV—LV end-diastolic volume;
ESV—LV end-systolic volume;
EF—ejection fraction;
CO—cardiac output.
Contractile systolic indexes are:
$dP/dt_{max}$ - maximal rate of pressure rise;
$dP/dt_{max}/IP$ - $dP/dt_{max}$ normalized to instantaneous developed pressure;
PMXI - power index: maximal ventricular power divided by $EDV^2$;
Msw - preload recruitable stroke work[3];
$Ees_n$ - End-systolic elastance normalized to measured heart mass.
The latter four indexes are load-independent measures of LV contractile function.
Diastolic indexes are: Tau - time constant of pressure relaxation derived using a monoexponential fit incorporating a non-zero pressure asympotote[4];
$dP/dt_{min}$ - peak rate of LV pressure decline;
PFR/EDV - peak ventricular diastolic filling rate normalized to EDV.
The latter reflects early diastolic properties, i.e. relaxation and passive stiffness during early filling. A higher value reflects improved diastolic function. p-values shown are for 1-way analysis of variance. A Tukey post-hoc multiple comparisons test was used to identify specific differences between groups:
(a) p = 0.042 vs 3 wkTAC + Sil;
(b) p < 0.001 vs Con and Sildenafil 3 wk;
(c) p < 0.05 vs Con, p < 0.001 vs 3 wk TAC + Sil;
(d) p < 0.05 vs all other groups;
(e) p = 0.02 vs Sildenafil 3 wk;
(f) p < 0.005 vs Con, Sildenafil 3 wk and 3 wk TAC;
(g) p < 0.01 vs all other groups;
(h) p < 0.05 vs Con, Sildenafil 3 wk and 3 wk TAC;
(i) p < 0.05 vs Con and Sildenafil;
(j) p < 0.01 vs Con, Sildenafil 3 wk and 3 wk TAC;
(k) p < 0.01 vs 3 wk TAC.

Figure 5:
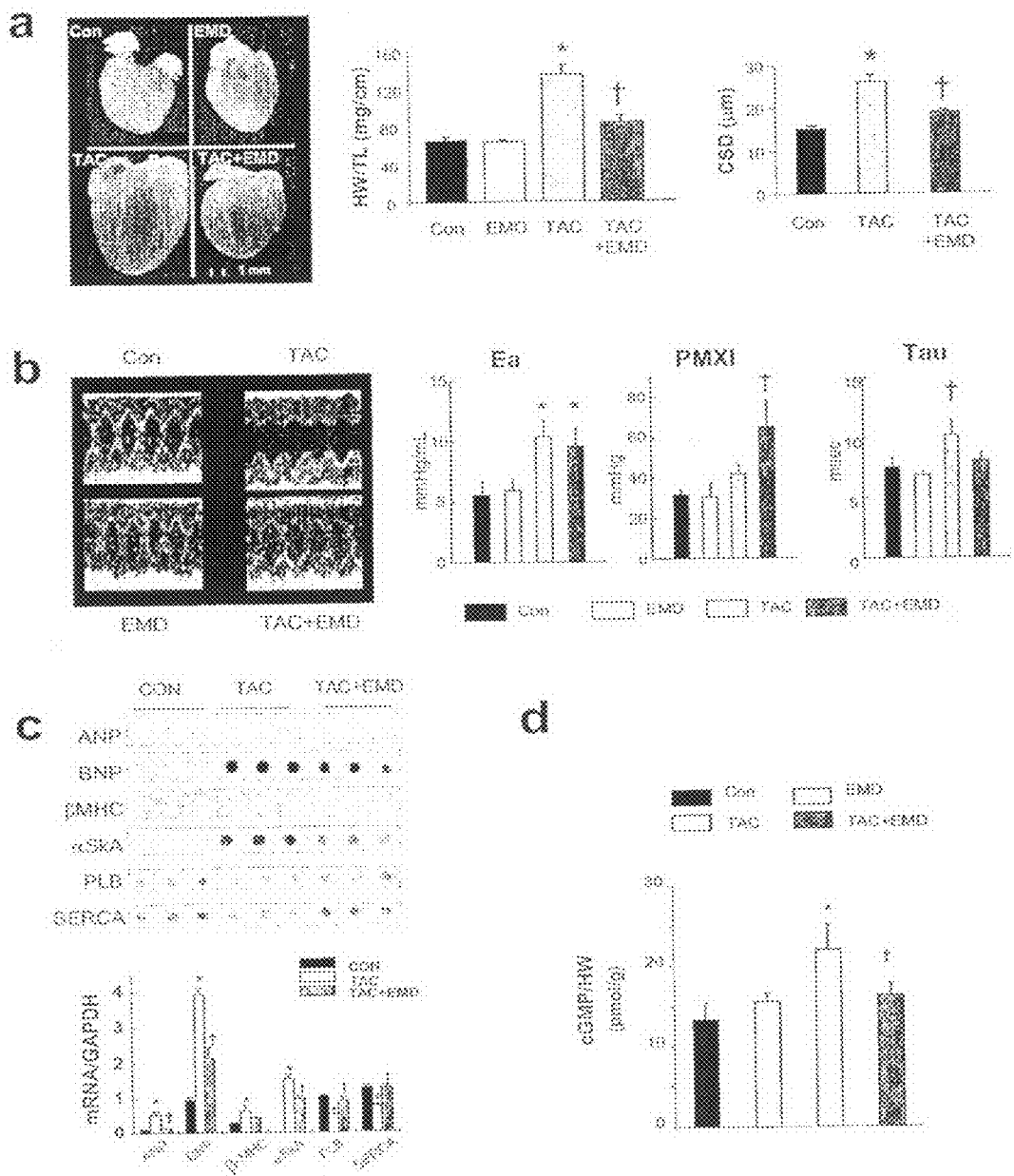
FIGS. 5A-5D demonstrate the ability of an alternative specific PDE5a inhibitor (EMD360527) to prevent the development of TAC (3-wk)-induced hypertrophy while concomitantly improving cardiac function.

PDE5A inhibition with EMD 360527 yielded near identical physiologic results (FIG. 5B). These studies further demonstrated that PDE5A inhibition reversed the TAC-induced rise in fetal gene expression (e.g. natriuretic peptides, α-skeletal actin) and depression of phospholamban and sarcoplasmic reticulum $Ca^{2+}$ ATPase expression (FIGS. 5C and 5D).

Example 4

TAC Hearts have Higher PDE5A Activity and Sildenafil-Induced PKG-1 Activity

The principal downstream effector kinase for cGMP in heart muscle is thought to be PKG-1, and elevation of PKG-1 either directly (genetic activation) or by natriuretic peptide signaling impedes hypertrophic responses. The premise that chronic sildenafil augments PKG-1 activity (FIG. 6A) was tested. In sham controls, sildenafil had no effect on activity—consistent with its negligible effect on resting heart function. In TAC hearts, PDE5A inhibition more than doubled PKG-1 activity. This result suggests that PDE5A activity is selectively enhanced in hypertrophied myocardium. cGMP-esterase activity and the component of activity attributable to PDE5A (FIG. 6B) was therefore measured. In sham controls, PDE5A contributed 35-45% of total activity, similar to data obtained in the dog[1]. In TAC hearts, total cGMP-esterase activity increased 20% over controls (p<0.005), and the component attributable to PDE5A was 60% of this total (p<0.001 vs control). Thus, TAC raised PDE5A activity which in turn likely explained the augmented effect of its inhibition by sildenafil on PKG-1 activation.

Figure 6:
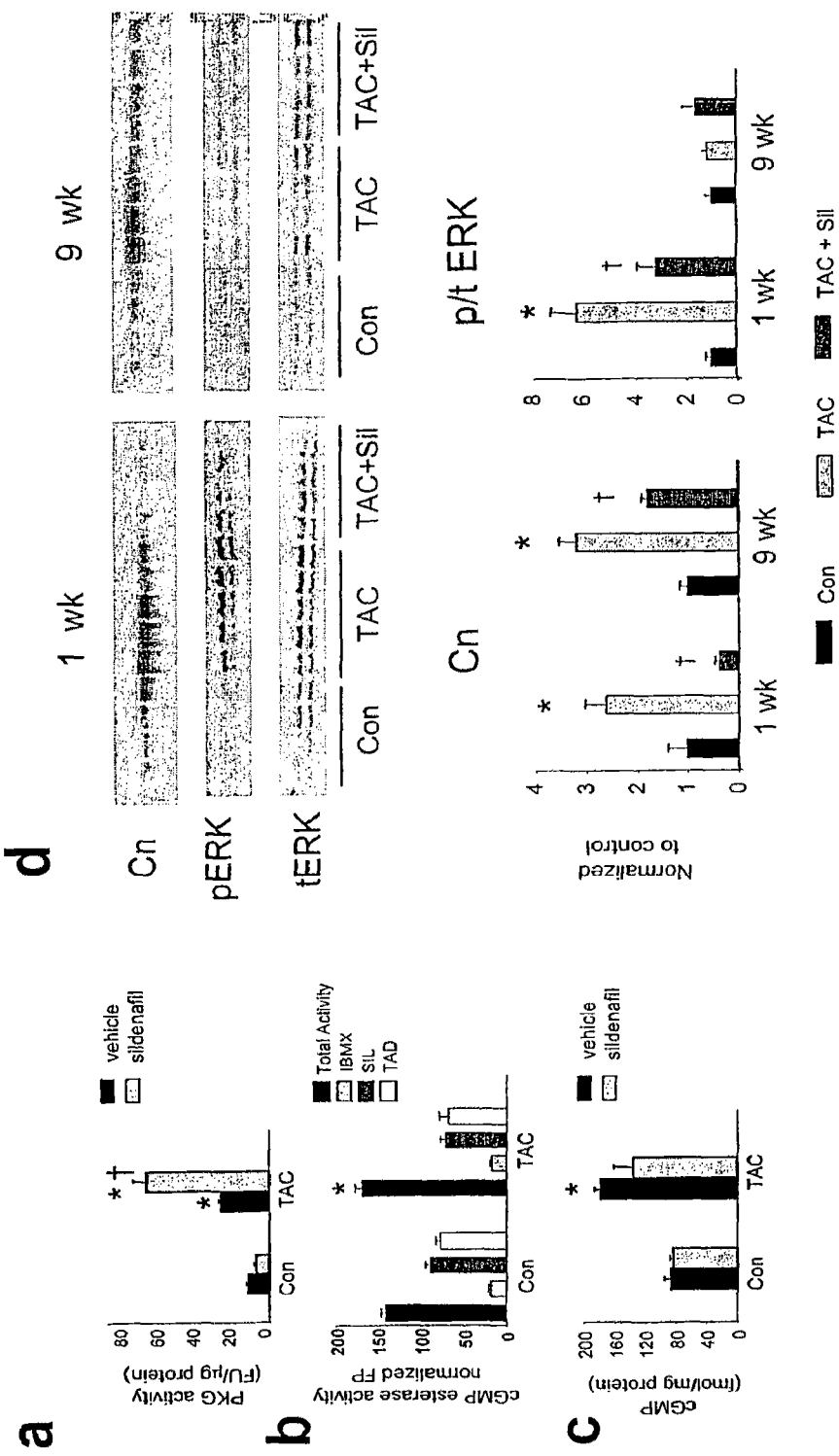
FIGS. 6A-6D show that PDE5A activity was increased in hearts stimulated to undergo hypertrophy and remodeling by pressure-overload. The stimulation of protein kinase G-1 by PDE5a was inhibited by sildenafil in this condition.

The impact of PDE5A inhibition on cGMP-dependent signaling was not, however, mirrored by total myocardial cGMP levels (FIG. 6C). Baseline cGMP did not change with sildenafil treatment in sham controls. While cGMP rose in TAC hearts, it declined when these hearts were co-treated with sildenafil. Identical findings were confirmed in separate studies using an alternative PDE5A inhibitor (FIG. 5D). This likely reflects concomitant changes in cGMP synthesis (i.e. associated with the prevention of hypertrophy and wall stretch) as suggested by a decline in natriuretic peptide expression (FIG. 5C). PDE5A-inhibition did not alter myocardial cAMP levels in either basal or TAC conditions.

Example 5

PDE5A-Inhibition Suppresses Calcineurin/NFAT and ERK1/2 Activation

Activation of the phosphatase calcineurin couples to nuclear migration of NFAT (nuclear factor of activated T cell) transcription factors that in turn induce cardiac hypertrophy and chamber remodeling[2,3]. This pathway can be inhibited by PKG-1, as overexpression of activated PKG-1 in neonatal myocytes suppresses calcineurin/NFAT activation and cellular hypertrophy[4]. Accordingly, calcineurin expression in TAC hearts was examined with or without sildenafil treatment. Calcineurin protein expression rose >2-fold after 1 and 9 weeks of TAC, and was significantly reduced by sildenafil at both time points (FIG. 6D).

The mitogen activated kinase ERK1/2 is induced by stretch and $G_{\alpha q}$-receptor coupled signaling[5,6] and by calcineurin activation[7], and is itself a contributor to hypertrophy[8]. After 1-week of TAC, ERK1/2 was activated (increase in phospho/total ERK1/2) and this too was suppressed by sildenafil treatment. However, after 9-weeks, ERK1/2 activation returned to baseline (despite persistent elevation of calcineurin) and sildenafil had no demonstrable effect (FIG. 6D).

Figure 7:
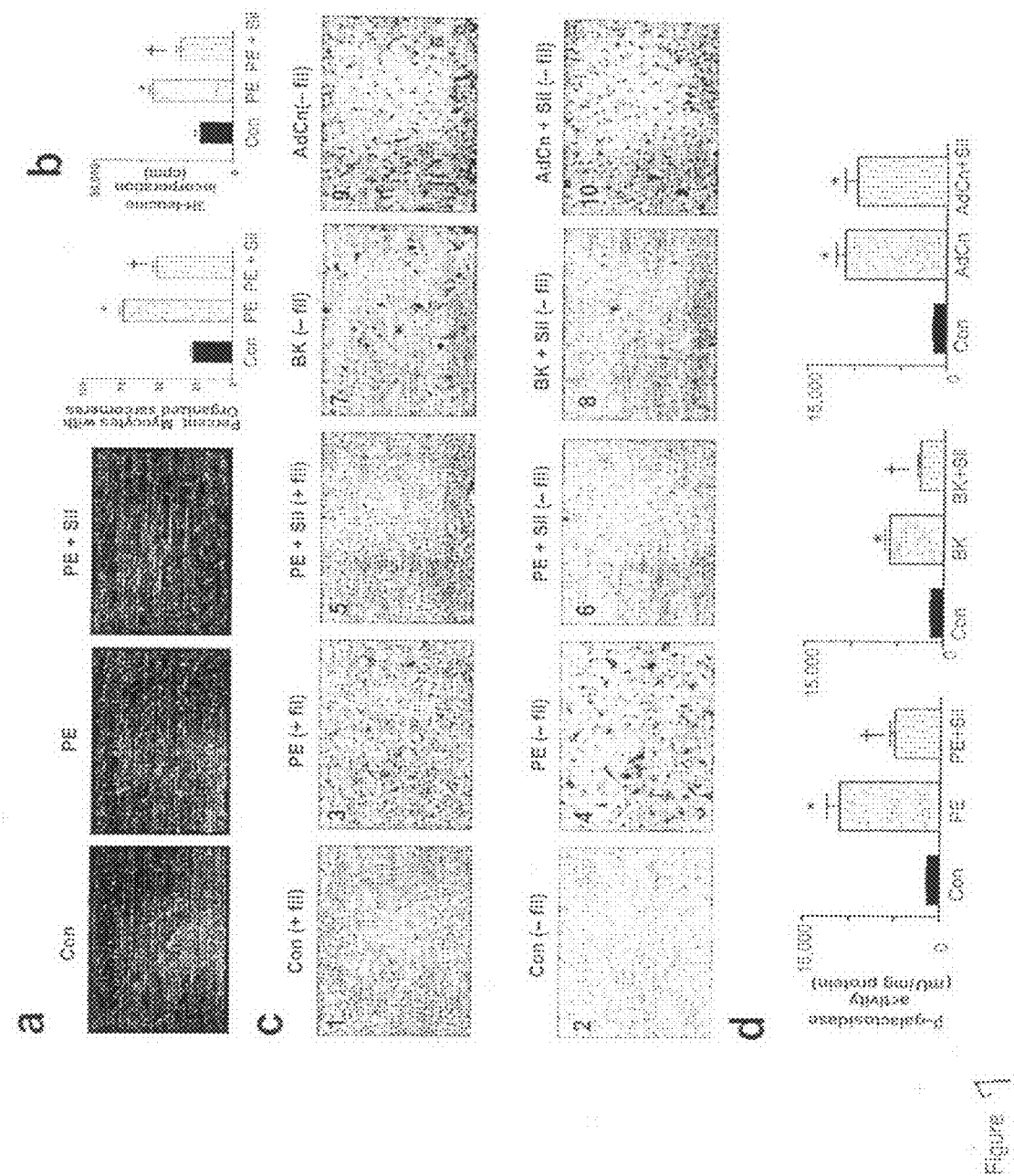
FIGS. 7A-7D show that PDE5A-inhibition with sildenafil prevents neonatal rat cardiomyocyte hypertrophy via calcineurin/NFAT dependent pathway.
Figure 8A:
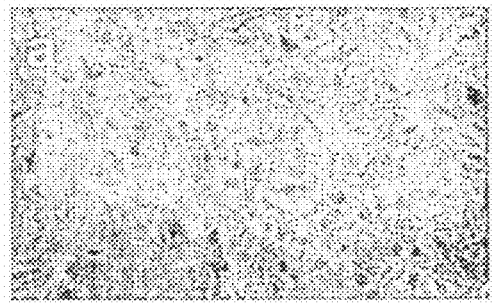
FIGS. 8A-8F are micrographs showing adenoviral transfection efficiency. Panels 8A and 8C display micrographs of neonatal myocytes from separate dishes transfected with adenovirus expressing nuclear targeted β-galactosidase, and stained using X-gal. Corresponding panels 8B and 8D are the same cells observed without phase contrast. Panels 8E and 8F show a lower power view of one dish (8E: with, and 8F: without phase contrast) to demonstrate uniformity of transfection. Transfection efficiency was consistent and near 95%.
Figure 8B:
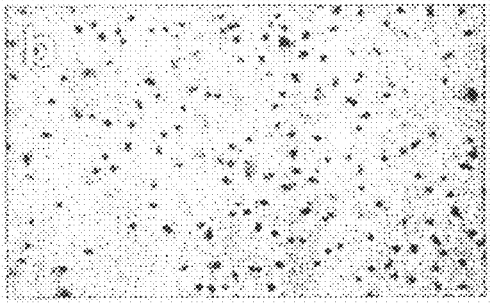
Figure 8C:
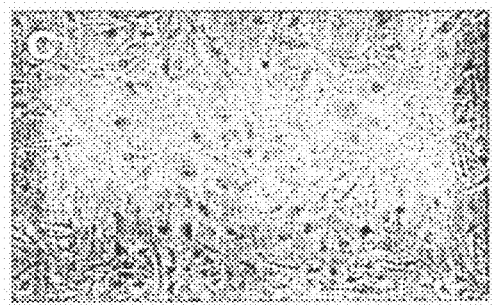
Figure 8D:
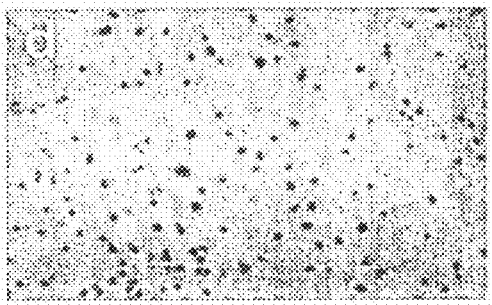
Figure 8E:
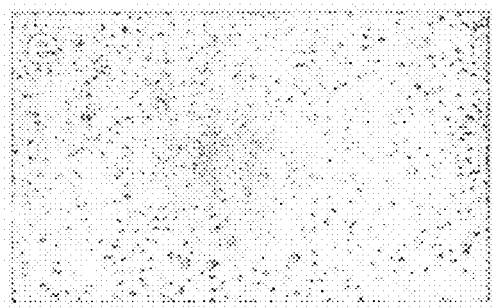
Figure 8F:
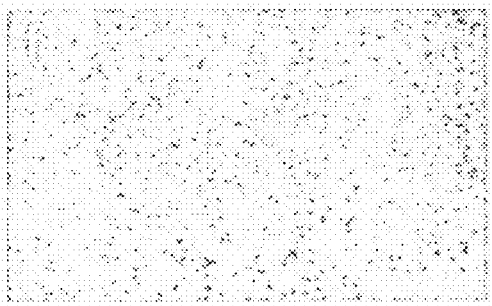

To clarify how PDE5A inhibition influenced calcineurin/NFAT-dependent hypertrophy this signaling in neonatal rat myocytes, was assessed. Incubation with phenylephrine (PE) induced cellular hypertrophy as assessed by sarcomere organization α-actinin, FIG. 7A) and de novo protein synthesis ([$^3$H]-leucine incorporation, FIG. 7B). This was suppressed by concomitant sildenafil treatment. To test whether sildenafil inhibited NFAT activation, myocytes were transfected with an adenovirus expressing the NFAT promoter coupled to β-galactosidase. Transfection efficiency was consistently >95% (FIGS. 8A-8F). Myocytes were then incubated with PE, the calcium activator BayK8644 (BK), or an adenovirus expressing constitutively active murine calcineurin A (AdCn). All three triggers enhanced NFAT promoter activity. Sildenafil suppressed activation stimulated by PE or BK, but not AdCn (FIG. 7C). Summary results based on β-galactosidase activity assay are shown in FIG. 7D. Studies performed using an alternative adenovirus with the NFAT promoter coupled to luciferase yielded identical results (FIGS. 9A-9C). These findings are concordant with prior data in which neonatal myocytes were transfected with constitutively active PKG-1[4], and support a target upstream of calcineurin itself.

Example 6

PDE5A-Inhibition Inactivates Akt by Upstream Inhibition

Figure 10:
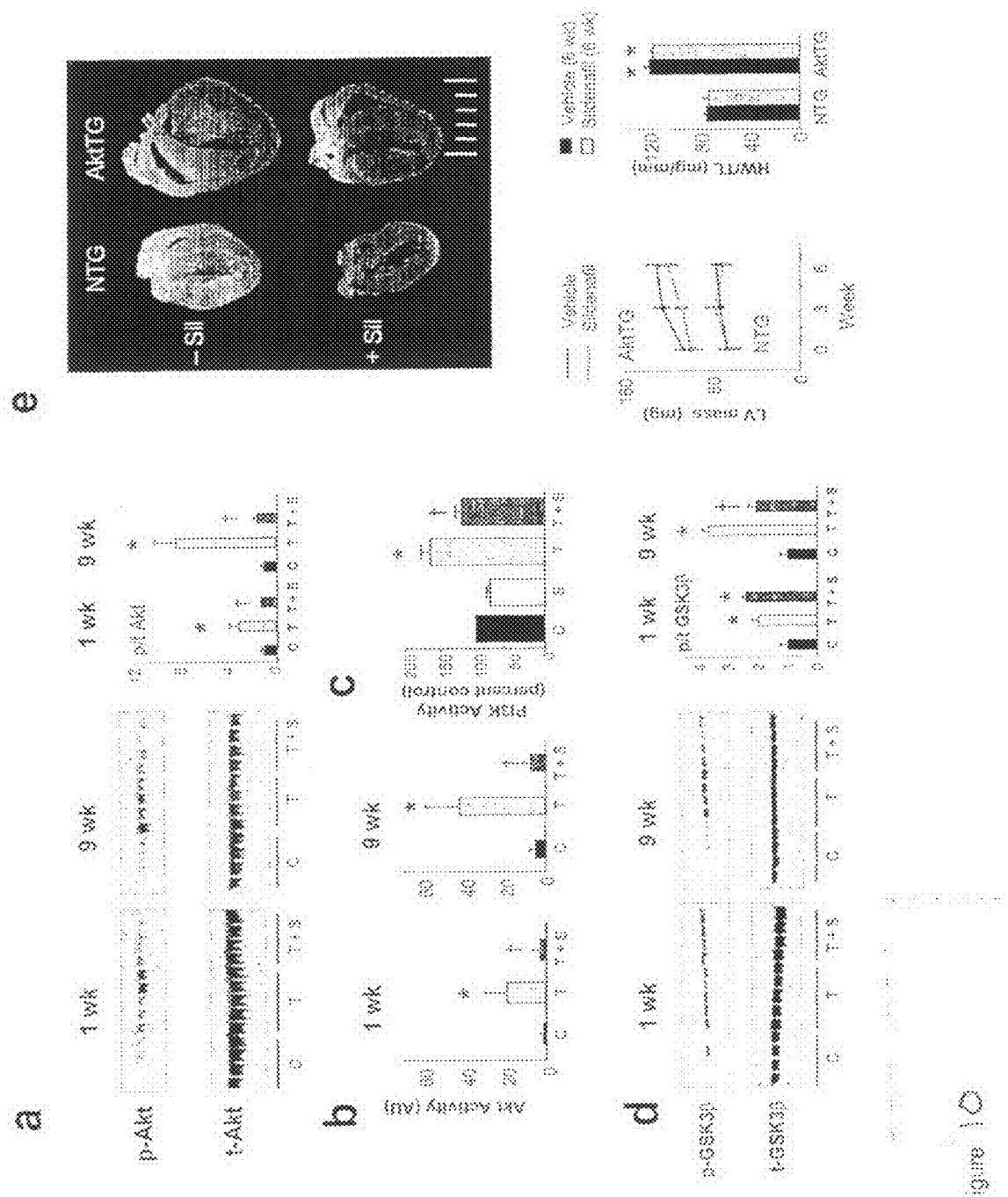
FIGS. 10A-10E show the inactivation of the Akt pathway by PDE5A inhibition.
Figure 11:
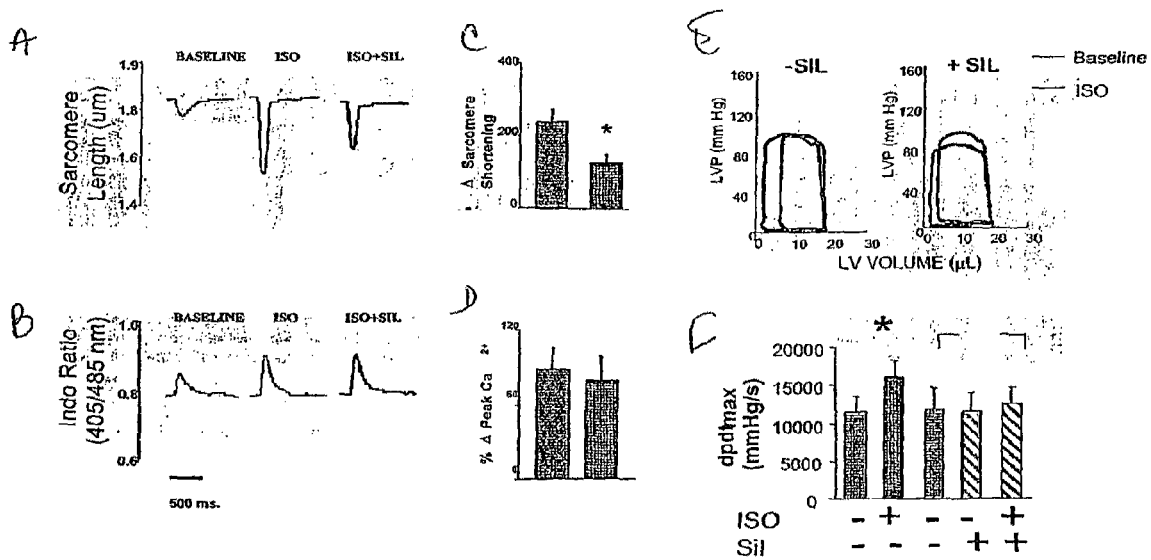
FIGS. 11A-11F show the anti-adrenergic effect of PDE5A inhibitors on isolated adult murine myocytes that were exposed to isoproterenol (ISO), and then to ISO in combination with sildenafil (ISO+SIL).

Another prominent signaling cascade stimulated by pressure-overload and whose hyperactivation is associated with cardiac hypertrophy and remodeling is the Akt/PI3K pathway. Akt activation occurs at modest levels with physiologic stress, but at higher levels, triggers pathologic remodeling and heart failure[9,10,11]. TAC increased Akt activity as shown both by the ratio of phosphorylated/total Akt protein expression (FIG. 10A) and activity assay (FIG. 10B). This was particularly prominent in the later-stage of pressure-load (9 weeks). Sildenafil suppressed this response at both time points to near baseline (FIGS. 10A and 10B). Akt is activated by phosphoinositide-3 kinase (PI3K)[11,12]. In particular, PI3Kα hyperactivity has been linked to myocyte hypertrophy[13], whereas the gamma isoform is associated with contractile dysfunction due to suppression of cAMP[13,14]. Given the preserved contractile function (FIG. 3) and unaltered cAMP at 3-week TAC, PI3Kα activity was assessed. PI3Kα activity increased with TAC. This increase was suppressed by sildenafil co-treatment (FIG. 10C).

To test whether PDE5A-inhibition interferes with downstream Akt signaling, we examined the glycogen synthase kinase 3β(GSK3β)[15], which is phosphorylated by Akt as well as other kinases[16] (e.g. PKA[17], and PKC[18]), leading to disinhibition of its intrinsic anti-hypertrophic activity[19]. At 1-week, phosphorylated/total GKS3β expression rose 2-fold by TAC, yet despite the decline in Akt activity by sildenafil treatment, GSK3β activation remained unchanged (FIG. 10D). After 9-weeks of TAC, however, Akt and GSK3β activation were much more stimulated, and PDE5A inhibition now reduced both. These data support Akt-independent activation of GSK3β particularly in early (non-dilated) phases of TAC not influenced by cGMP/PKG-1/PDE5A, and Akt-dependent activation of GSK3β that is blunted by sildenafil.

To further test whether inhibition of Akt-activation by sildenafil operates through downstream signaling pathways, transgenic mice with cardiac-targeted overexpression of constitutively activated Akt (AktTG) were chronically treated with vehicle or sildenafil. In vehicle-treated animals (age 4-5 months), AktTG hearts were larger and had reduced heart function (FIG. 10E and Table 3).

TABLE 3

Hemodynamic analysis of non-transgenic controls (NTG) and transgenics with cardiac-targeted Akt overexpresion (AktTG). Data are from invasive pressure-volume analysis.

|  | NTG | AktTG | $p^1$ | NTG | AktTG | $p^2$ | $p^3$ |
|  | Vehicle | | | Sildenafil | | | |
|---|---|---|---|---|---|---|---|
| HR | 538.7 ± 9.7 | 515.3 ± 24.6 | NS | 511.6 ± 31.4 | 569.5 ± 47.4 | NS | NS |
| ESP | 96.1 ± 2.1 | 93.4 ± 4.6 | NS | 96.7 ± 4.7 | 90.1 ± 0.9 | NS | NS |
| EDP | 7.5 ± 0.7 | 8.1 ± 1.6 | NS | 4.9 ± 1.2 | 8.9 ± 1.1 | NS | NS |
| ESV | 17.6 ± 1.9 | 36.4 ± 6.1 | <0.05 | 19.4 ± 3.0 | 39.6 ± 4.5 | <0.01 | NS |
| EDV | 45.9 ± 5.8 | 55.0 ± 6.3 | 0.33 | 44.5 ± 4.9 | 57.6 ± 5.4 | 0.05 | NS |
| EF | 61.4 ± 0.9 | 34.7 ± 5.5 | <0.005 | 56.7 ± 3.5 | 31.8 ± 2.1 | <0.001 | NS |
| $dPdt_{max}$ | 9447 ± 556 | 7188 ± 354 | <0.02 | 10133 ± 791 | 6993 ± 156 | <0.005 | NS |
| $dPdt_{min}$ | −9051 ± 573 | −6248 ± 349 | <0.006 | −9267 ± 417 | −6241 ± 289 | <0.001 | NS |
| PMXI | 27.1 ± 1.8 | 18.2 ± 2.7 | <0.05 | 25.9 ± 2.2 | 17.8 ± 1.9 | <0.05 | NS |
| Tau | 6.8 ± 0.2 | 10.5 ± 1.4 | <0.05 | 7.4 ± 0.6 | 10.0 ± 0.6 | <0.02 | NS |
| $dP/dt_{max}/IP$ | 173.1 ± 6.6 | 144.5 ± 9.2 | <0.05 | 176.4 ± 14.8 | 128.5 ± 2.9 | <0.02 | NS |
| $Ees_n$ | 46.7 ± 5.5 | 22.7 ± 4.1 | <0.02 | 39.9 ± 1.5 | 21.5 ± 2.9 | <0.001 | NS |

Data are mean ± sem.
Abbreviations are as described above.
$p^1$ - p-value for unpaired t-test between NTG and AktTG treated with vehicle;
$p^2$ - p-value for unpaired t-test between NTG and AktTG both treated with sildenafil 100 mg/kg/day;
$p^3$ - p-value for unpaired t-test between AktTG treated with vehicle versus sildenafil.

Sildenafil did not blunt progressive hypertrophy over a 6-week period as shown by serial echocardiography and heart weight/tibia length ratios (FIG. 10E). Both systolic and diastolic function remained depressed in AktTG animals despite sildenafil treatment (Table 3). These findings suggest that sildenafil acts upstream of Akt activation, consistent with the PI3K enzyme activity results.

These results indicate the novel and potent efficacy of PDE5A inhibition to suppress chamber, cellular, and molecular remodeling while enhancing cardiac function in hearts exposed to sustained pressure-overload. Inhibition of PDE5A also reversed pre-existing hypertrophy while improving function—again despite persistent load increase. Small molecule approaches that suppress (or reverse) hypertrophy to the extent observed in the present study are uncommon, suggesting the underlying mechanism(s) linked to PDE5A/cGMP/PKG-1 modulation are potent and likely interfere with several pathways. Given the simplicity of the therapy and existing wide clinical experience and safety record of PDE5A inhibitors, they are useful for the treatment of virtually any cardiac condition characterized by morphologic, cellular, or molecular hypertrophic remodeling.

These findings are particularly intriguing in light of the minimal influence that PDE5A inhibition has been previously thought to have on the heart[19,20]. Earlier studies focused almost exclusively on acute effects and/or responses in normal hearts at rest. Cardiac PDE5A expression levels are low[1,21], and the acute effect of PDE5A inhibition on basal function is minimal[1,19,21]. Recent studies in two different species have found PDE5A can potently regulate beta-adrenergic heart and cardiac myocyte stimulation, and that this effect is coupled to its strategic localization at z-band structures[1,21]. The current study shows that even chronic PDE5A inhibition has negligible effect on the normal heart, but that this situation changes dramatically in hearts under chronic loading stress. This is explained in part by greater PDE5A-dependent cGMP-esterase activity in the pressure-loaded hearts than controls, which resulted in much larger changes in PKG-1 activation following PDE5A inhibition. Analogous counter regulation of cGMP catabolic enzymes when cGMP synthesis is stimulated has been reported in vasculature (PDE1A increasing with chronic nitrate infusion as a mechanism of nitrate intolerance[22]) and the kidney (PDE5A increasing with chronic volume load as a mechanism for renal desensitization to natriuretic peptide[23]). The current results are the first to reveal such regulation in the heart.

Without wishing to be bound by any particular theory, enhanced activation of PDE5A and its role in cGMP homeostasis may be explained by several mechanisms. PDE5A activity is enhanced by cGMP—both by direct binding to a GAF domain[24], and by activating PKG-1 which phosphorylates PDE5A in a regulatory domain to enhance catalytic activity[25]. Both events enhance esterase activity—serving as a negative feedback loop to modulate cGMP levels. In addition, cGMP-dependent signaling appears generally more potent in hearts under stress—much like an automotive brake. For example, nitric oxide stimulated cGMP synthesis has minimal effects on basal contractility, but is more potent under adrenergic or other stress[26,27]. Acute PDE5A-inhibition also has minimal effects on basal function, yet suppresses β-adrenergic stimulated cardiac contractility[1] in the conscious dog.

Prior studies regarding cGMP/PKG-1 suppression of hypertrophy have primarily targeted natriuretic peptide-dependent synthesis. Cardiac deletion of the ANP receptor[28,29,30,40,41] exacerbates load-induced hypertrophy, whereas modest chamber hypertrophy can be prevented by myocyte-targeted overexpression of a constitutively activated ANP-receptor guanylate cyclase domain[31]. These changes are accompanied by decreases or increases in myocardial cGMP. However, unlike ANP-coupled signaling, inhibiting PDE5A generates a potent anti-hypertrophic effect without an apparent increase in total myocardial cGMP—and despite greatly enhanced PKG-1 activity. This indicates that total myocardial levels do not necessarily reflect cGMP-signaling. It is highly likely that alterations in cGMP signaling exist within localized sub-domains within the cell. Recent studies from other laboratories support this contention, and in particular the notion that specific PDEs target the degradation of cGMP depending upon the enzyme responsible for its synthesis. cGMP binding to PKG-1 allosteric sites is thought to be an important mechanism for its sequestration from the cytosol and a means of protecting it from PDE5A hydrolysis[32]. This could underlie enhanced PKG-1 activation despite the lack of commensurate increases in cGMP. Compartmentalized signaling is further supported by enhanced PDE5A expression near z-band structures in heart muscle cells and the loss of physiologic activity when this localization is altered[1]. Total cGMP may particularly reflect the synthetic pathway involved, with higher levels induced by natriuretic peptide stimulation. Hearts treated with sildenafil had reduced wall stress and ANP/BNP expression; thus, some decline in cGMP might be expected.

Sustained pressure-load activates multiple kinases and phosphatases, and selective targeting of many of these proteins by genetic engineering has revealed potent involvement in the cardiac hypertrophic response. PDE5A inhibition appeared to counter several pathways, and while it is always possible that the observed changes were secondary to an as yet unidentified primary effector, this seems to be unlikely because of the following reasons. First, as with PKA-dependent signaling, it is known that cGMP/PKG-1 signaling can impact multiple enzyme cascades[4,33,34] including calcineurin. Secondly, the changes observed in ERK1/2, Akt, PI3Kγ, and calcineurin in response to sustained pressure-load were each in ranges shown individually to stimulate myocardial hypertrophy and/or remodeling in various genetic models[2,8,10,13], making a single culprit less likely. And thirdly, the amplitudes and time-course of the changes observed are incompatible with a single effector based on results from genetically engineered models. For example, although ERK 1/2 activation increases in mice overexpressing calcineurin[35,36], ERK1/2 phosphorylation was negligible after 9-weeks TAC despite persistent calcineurin stimulation. Genetic inhibition of calcineurin in TAC-mice does not reverse ERK1/2 activation[35], yet declines in both were observed with sildenafil administration. Calcineurin-overexpression also triggers Akt activation[36], but at much lower levels than was observed with TAC. This could not explain the temporal disparities in Akt and calcineurin changes. Mice lacking the PI3K inhibitor PTEN develop myocyte hypertrophy and systolic dysfunction, as well as Akt and GSK3β activation, but do not display ERK1/2 activation[13]. In addition, genetic enhancement of Akt or PI3K activity to levels similar to those achieved by TAC in the present study induces systolic dysfunction[13] and chamber dilation[10,37], yet is not associated with calcineurin co-stimulation[38]. Collectively, these discrepancies suggest that more than one pathway is targeted by PDE5A-inhibition.

The apparent discrepancy between Akt and GSK3β suppression by sildenafil after 1-week TAC deserves comment. GSK3β is activated by TAC, and by itself is associated with hypertrophyl[19] and cardiac dysfunction[39]. However, GSK3β can also be phosphorylated by PKA via anchoring kinase AKAP220[17], by PKCγ[18], and other kinases[16]. Given the decline in Akt activation despite sustained GSK3β phosphorylation, one or more of these Akt-independent pathways appear to be involved—yet not regulated by PDE5A-inhibition. The later stage of hypertrophy was marked by substantial remodeling and greater Akt and GSK3β activation. Inhibition of both by sildenafil at this stage could underlie the sustained benefit.

Although cardiac hypertrophy has been traditionally thought of as an adaptive response to loading stress, evidence suggests it may not be a required compensation[37]. While sildenafil did not fully reverse or impede the marked hypertrophy, chamber and molecular remodeling observed after weeks to several months of TAC, cardiac function improved despite the sustained load. The current findings are of clinical interest given the high prevalence of hypertensive heart disease and hypertrophy that play a prominent role in many forms of heart failure. The expanding use of oral PDE5A inhibitors to treat disorders such as pulmonary hypertension[40] and not only erectile dysfunction, is supporting their use as a chronic therapy.

Example 7

PDE5a Inhibitor Blunts Cardiac Muscle Cell Response to Isoproterenol

Figure 14A:
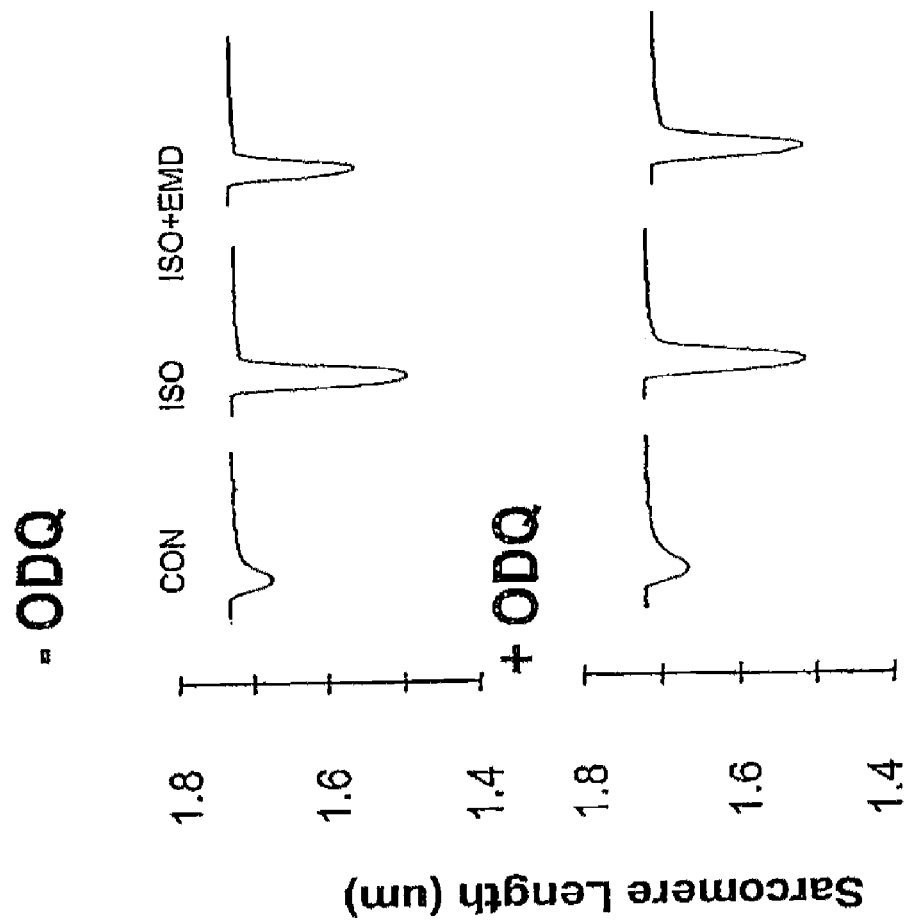

Isoproterenol, a β-adrenergic receptor agonist stimulates cardiac muscle cell contraction. A PDE5a inhibitor (sildenafil, 100 nM) blunted the enhanced contraction of primary isolated cardiac muscle cells in response to stimulation by the adrenergic agonist-isoproterenol (FIGS. 11A-11D). This blunting is prevented if soluble guanylate cyclase is inhibited with ODQ, a soluble guanylate cyclase (sGC) inhibitor (FIGS. 14A and 14B). This indicates that PDE5a inhibitors modify cardiac function by regulating cGMP, which is generated by sGC. Thus, the mechanism of action for PDE5a inhibitors is likely to be different from the mechanism proposed for activation of ATP sensitive potassium channels which may modify post-ischemic function. These data also definitively show that the effect of PDE5 inhibitors does not depend on arterial vasodilation or in fact on any arterial changes at all.

Example 8

PDE5A Inhibition Stimulates PKG-1 and cGMP

Figure 15:
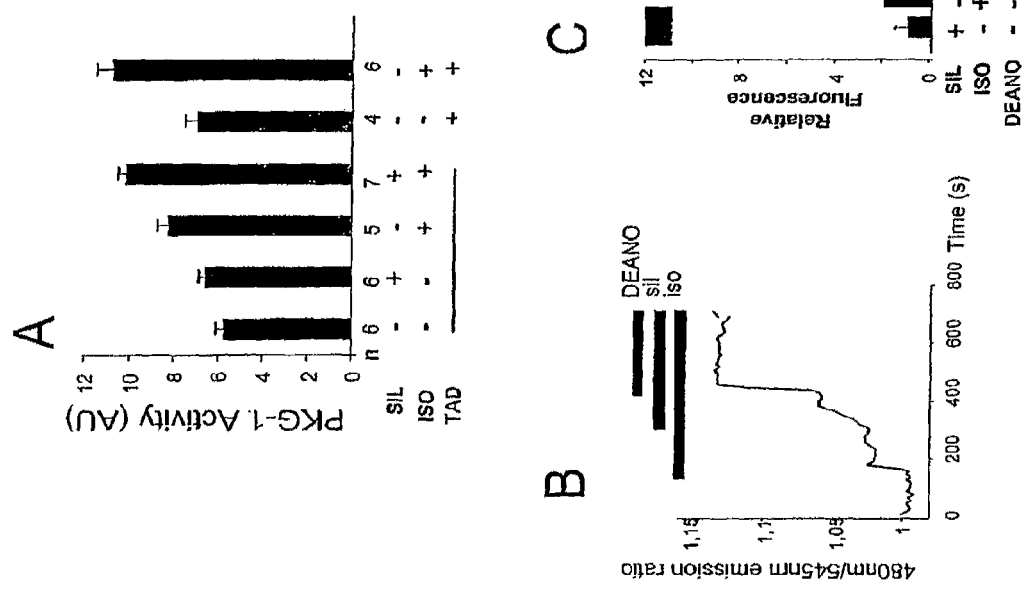
FIGS. 15A, 15B, and 15C are graphs showing that a PDE5a inhibitor enhances cGMP in isolated adult cardiac muscle cells.

To directly determine whether PDE5A inhibition stimulated PKG-1 in adult myocytes (FIG. 15A), the effect of PDE5A inhibition on protein kinase G1 (PKG-1) was tested with sildenafil alone, isoproterenol alone, both combined, tadalafil alone, and tadalafil combined with isoproterenol. PDE5A inhibition slightly enhanced PKG-1 activity under basal conditions (~10%, $p<0.05$). When isoproterenol was combined with either PDE5a inhibitor, there was a marked 50% rise in PKG activity. This is consistent with the anticipated effect of inhibiting PDE5a, which is expected to increase cGMP levels, which then activate PKG. To directly monitor intracellular cGMP production, a fluorescence resonance energy transfer probe sensitive to cGMP levels was used in neonatal rat myocytes (FIGS. 15B and 15C). Isoproterenol, sildenafil, and the NO donor (DEA/NO) all enhanced the FRET signal, providing the first direct demonstration that PDE5A inhibition enhances cGMP in myocytes (FIGS. 15A-15C).

Example 9

PDE5a Inhibition Blocks β-Adrenergic Stimulated Contractility, and Chronically Prevents Adrenergic-Stimulated Cardiac Hypertrophy Acute increases in cardiac chamber contractility were induced by isoproterenol infusion in control C57bl6 mice. The increase in cardiac systolic function was assessed by in vivo pressure-volume relations (FIG. 11E), and is reflected by a widening of the loop and shift of the upper left corner to the left. Sildenafil delivered intravenously at a dose that yielded a free plasma concentration of 30 nM results in a marked suppression of this adrenergic stimulation response. This supports the myocyte effects at the intact heart level. Furthermore, if isoproterenol is infused chronically by means of an implanted osmotic mini-pump, the heart responds by increasing the cardiac mass (hypertrophy) and with some dilation. This is shown for a group of control C57b16 mice (FIGS. 12A and 12B). Co-treatment with a PDE5a inhibitor (EMD 360527) markedly inhibited the development of cardiac hypertrophy.

Figure 13A:
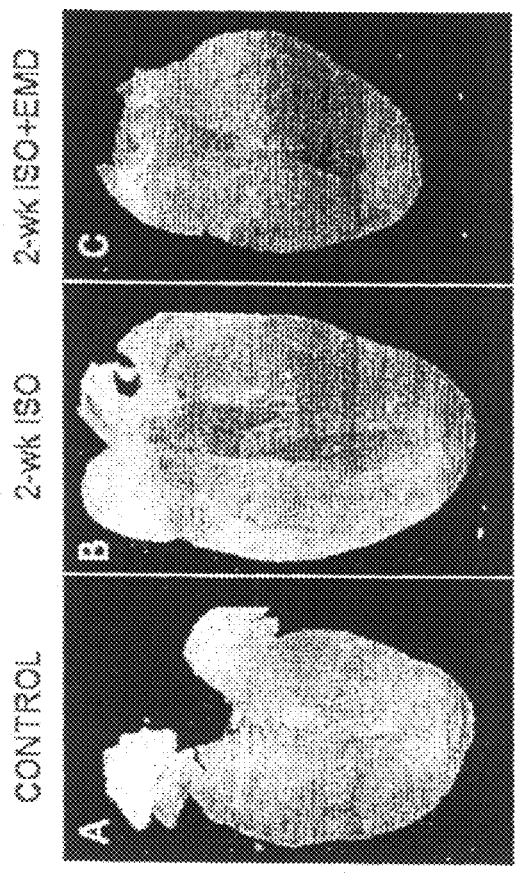
FIGS. 13A and 13B are graphs showing that atrial natriuretic peptide (ANP) does not suppress cardiac alterations associated with β-adrenergic stimulation as PDE5A inhibition does. When ANP was infused intravenously, it resulted in a marked increase in myocardial cGMP (right panel). This did not inhibit isoproterenol-stimulated contractility (left panel displays the maximal rate of pressure rise; $dP/dt_{max}$ at baseline, with ISO, rebaseline, ANP alone, and ANP+ISO). This was very different to what was observed with a PDE5a inhibitor as shown above. The cGMP measurements with PDE5a inhibition showed little change. Without wishing to be tied to any particular theory, these results likely indicate that novel highly compartmentalized signaling underlies PDE5a's myocardial effects.
Figure 13B:
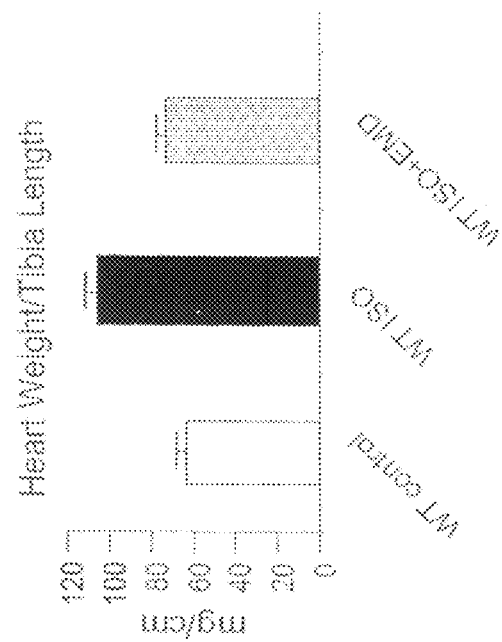

Importantly, the efficacy of PDE5a inhibition to block β-adrenergic stimulation is specific to the intervention, and not duplicated by other methods to enhance myocardial cGMP. FIG. 13A shows the effect of stimulating cGMP in the myocardium by atrial natriuretic peptide (ANP) infusion on the isoproterenol cardiac response. Unlike the data provided in FIG. 11F using a PDE5a inhibitor, ANP had no effect on the ISO response in the intact heart. FIG. 13B shows the measured levels of cGMP in the myocardium in hearts under control conditions, and those exposed to intravenous PDE5a inhibition (EM 360527) or ANP. The latter induced a marked rise in myocardial cGMP—yet had no effect on the sympathetic stimulatory response. The PDE5a inhibitor, on the other hand, had negligible effect on measured whole myocardial cGMP, yet this was very potent as a negative regulator of beta-adrenergic stimulation. Lack of measured cGMP rise in heart due to PDE5a inhibitors has been previously used to support a lack of significant physiologic role in the heart. However, these data show that the signal is highly compartmentalized, an that precisely the correct region is modulated by PDE5a inhibition to have the impact on cardiac contractility, and that this is not simply mimicked by enhancing cGMP by synthetic means.

Example 10

PDE5a Expression and In Vitro Activity

Figures 16B, 16C:
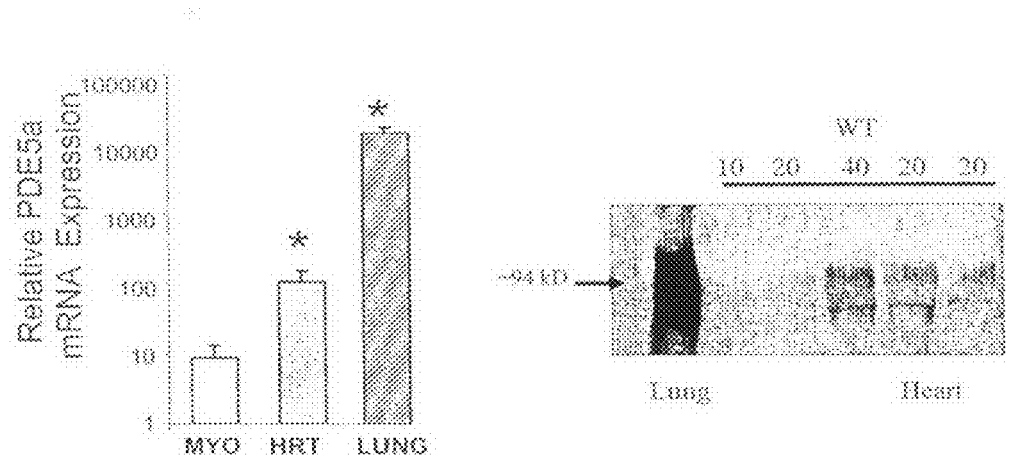

PDE5A mRNA expression was 100-fold lower in isolated myocytes than in lung (FIG. 16B). Protein expression was observed in isolated adult cardiac myocytes, but again the level was much lower than in lung (FIG. 16A). The SDS-PAGE gel shows loading with 1 μg in lung, compared to 100× that amount for the heart to match the density level. Previous reports had shown that PDE5A is expressed at low levels in myocytes, and this low level of expression had lead to the assertion that PDE5A does not play a functionally significant role in cardiac muscle cells. Protein and gene expression was also found to be diminished in whole heart compared with lung (FIG. 16C). In lung, it resides primarily in the vascular smooth muscle cells. Here, the SDS-PAGE gel was loaded with 20 μg of myocardial-derived or lung-derived protein, and the relative expression differences are very apparent. This is supported by disparities in the mRNA expression between these tissues (FIG. 16A). In the whole heart, a prominent band was observed at 95 kDa in isolated myocytes that was approximately the same size as the band observed in lung. A second ~70 kDa band was consistently observed in heart tissue that either reflected a splice variant or a proteolytic fragment. Similar findings were obtained with alternative antibodies[41,42].

Total cGMP and PDE5a-dependent cGMP esterase activity were determined for adult isolated myocytes and for intact heart myocardium (FIGS. 16D and 16E). Co-incubation of either tissue with IBMX, a broad spectrum PDE inhibitor, lowered cGMP-esterase activity by ~90%. Co-incubation of either tissue extract with sildenafil (SIL)—a selective PDE5a inhibitor, revealed only the component of cGMP normally catabolized by PDE5A. This was approximately 30% in both isolated myocytes, and the whole heart. Similar results for PDE5A-dependent cGMP-esterase activity were obtained by radio-enzyme assay[41] (32±17.3%-NTG (n=9)).

Prior studies have reported low-levels of PDE5A expression in the myocardium[43,44] and minimal effects of PDE5A inhibition on resting heart function[41,45,46,47], which led to the erroneous conclusion that PDE5A plays little role in the heart. In contrast to previous reports, the present studies show that this low level of expression does not indicate that PDE5A lacks physiologic function. Rather, the current results indicated that PDE5A plays an important function in β-adrenergic stimulation, and in cardiac remodeling, hypertrophy, and dysfunction to chronic stress. The effects from preventing cGMP catabolism by inhibiting PDE5a appear to be substantially greater than those reported from increasing cGMP synthesis by natriuretic peptide-coupled synthesis[48,49], or adrenergic stimulated contractility changes. This supports a very novel mechanism that has not been previously appreciated or recognized by which targeted cGMP manipulation can directly influence the heart muscle cell and thus heart itself.

Example 11

Myocyte Localization of PDE5A

Figure 17:
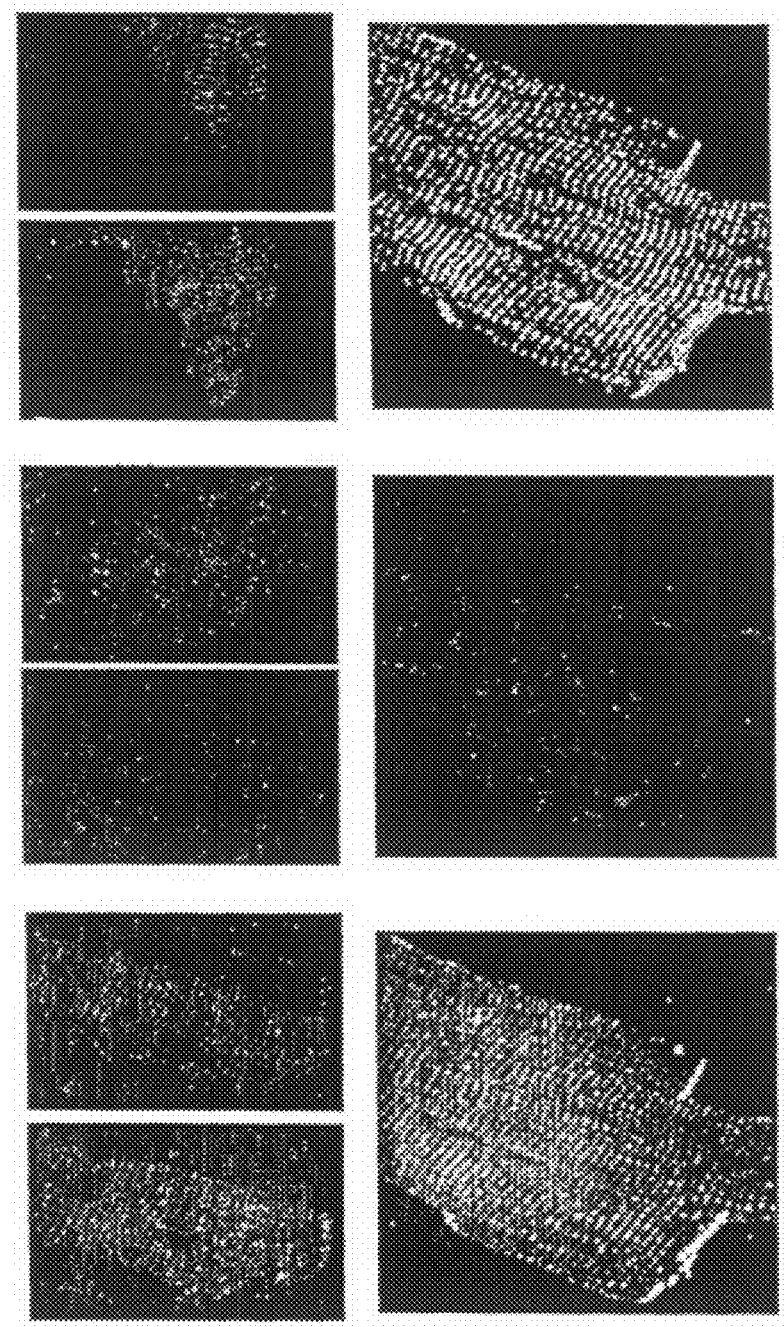
FIGS. 17A-17F show confocal immunostaining of cardiomyocyte PDE5A distribution.

PDE5A was present throughout the cardiomyocyte (FIGS. 17A-17F) and also localized to z-band striations (FIG. 17A (left panel), (right panel)-α-actinin). PDE5A immunostaining was inhibited by a specific blocking peptide (FIG. 17B, left) whereas this same peptide did not block PDE1C staining (FIG. 17C, left), supporting assay specificity. PDE5A was present at z-band striations (FIGS. 17D and 17F), and colocalizes with the NO synthetic enzyme NOS3.

Example 12

Baseline Analysis and Sildenafil Effect

PDE5A is expressed at low levels in the myocardium[51-53], and its inhibition by sildenafil or other agents has not been thought to directly affect heart function as these drugs induce only a slight decline in arterial pressure and have no apparent effect on cardiac ejection fraction or output at rest[54,55] or during exercise.[56,57] As reported above, despite low expression levels, PDE5A can exert potent localized regulation over adrenergic stimulation[58,59], and its chronic inhibition markedly limits and reverses cardiac hypertrophy and remodeling stimulated by pressure overload.[60] These results support the therapeutic use of PDE5A inhibitors in treating or preventing cardiac hypertrophy and remodeling.

To determine whether sildenafil pretreatment suppresses beta-adrenergic stimulated cardiac contractility in healthy human subjects, a randomized, double-blinded, placebo-controlled, non-invasive hemodynamic study was performed, employing dobutamine stress testing before and after administration of oral sildenafil or placebo.

Dobutamine is an adrenergic beta-1 agonist that has a positive inotropic effect and is used clinically to pharmacologically stimulate (and stress) cardiac tissue and increase heart pump function. Sildenafil inhibits phosphodiesterase 5 (PDE5A) to elevate intracellular cyclic GMP and induce vasodilation. As reported herein, sildenafil also potently effected hearts stimulated by beta-adrenergic receptor agonists or pressure overloads. To determine whether sildenafil blunts dobutamine-stimulated cardiac function in humans, thirty-five healthy volunteers underwent a randomized, double-blind, placebo-controlled study in which cardiac function was assessed in response to dobutamine before and after oral sildenafil (100 mg, n=19) or placebo (n=16). Echo-Doppler and noninvasive blood pressure data yielded load-independent contractility indexes (maximal power index and end-systolic elastance), ejection fraction, and measures of diastolic function.

Free plasma sildenafil concentration was 44±29 nM in the active treatment group, and 22±18 nM for its metabolite—desmethyl-sildenafil, (50% of parent drug level is anticipated)[21]. In four of the subjects receiving sildenafil, plasma concentrations were very low (all <6 nM, mean 3.6 nM) at the time of the study (i.e., 10-fold below the group average). In addition, each of these subjects also had low metabolite levels, arguing against rapid metabolism to explain the subtherapeutic concentrations. Since testing our hypothesis required establishing a therapeutic sildenafil level, these subjects were excluded from analysis. One additional subject was excluded as their blood sample was lost. There were no adverse events during the study.

There were no baseline differences between the placebo and sildenafil treated groups with respect to age (30±6 vs.30±8 years, respectively; p=0.95), gender (50 vs. 79% female; p=0.1), body mass index (23.9±3.5 vs 22.9±2.5 kg/m$^2$; p=0.45), or cardiac function indexes (Table 4).

TABLE 4

Analysis of Systolic and Diastolic Baseline Data for First versus Second Dobutamine Study

| | Placebo (n = 16) | | Sildenafil (n = 19) | | P value | |
| --- | --- | --- | --- | --- | --- | --- |
| | $B_1$ | $\Delta(B_2 - B_1)$ | $B_1$ | $\Delta(B_2 - B_1)$ | a | b |
| Systolic Variables | | | | | | |
| Systolic Blood Pressure (mmHg) | 106 ± 13 | −3 ± 9 | 107 ± 12 | −6 ± 3* | 0.79 | 0.26 |
| Diastolic Blood Pressure (mmHg) | 59 ± 7 | −2 ± 6 | 62 ± 6 | −6 ± 5* | 0.18 | 0.05 |
| Heart Rate (min$^{-1}$) | 61 ± 9 | −2 ± 4 | 66 ± 12 | +0 ± 3 | 0.24 | 0.44 |
| Stroke Volume (mL) | 77 ± 17 | +3 ± 7 | 72 ± 16 | +5 ± 6* | 0.34 | 0.44 |
| Total Peripheral Resistance (dyne * s/cm$^5$) | 1310 ± 280 | −55 ± 130 | 1370 ± 310 | −170 ± 60* | 0.57 | 0.03 |
| Peak Power Index (mmHg/sec) | 297 ± 42 | +6 ± 31 | 312 ± 61 | +21 ± 13* | 0.42 | 0.26 |
| End Systolic Elastance (mmHg/mL) | 2.3 ± 0.8 | +0.2 ± 0.6 | 2.6 ± 0.9 | +0.4 ± 0.2* | 0.40 | 0.25 |

TABLE 4-continued

Analysis of Systolic and Diastolic Baseline Data for First versus Second Dobutamine Study

|  | Placebo (n = 16) | | Sildenafil (n = 19) | | P value | |
| --- | --- | --- | --- | --- | --- | --- |
|  | $B_1$ | $\Delta(B_2 - B_1)$ | $B_1$ | $\Delta(B_2 - B_1)$ | a | b |
| Ejection Fraction | 61 ± 5 | +3 ± 4 | 61 ± 6 | +6 ± 2* | 0.99 | 0.05 |
| Diastolic Variables | | | | | | |
| E velocity (cm/sec) | 87 ± 12 | +0 ± 12 | 92 ± 19 | −4 ± 12 | 0.32 | 0.24 |
| A velocity (cm/sec) | 59 ± 8 | +5 ± 8 | 57 ± 17 | −3 ± 8 | 0.59 | 0.63 |
| E/A ratio | 1.5 ± 0.2 | +0.1 ± 0.2 | 1.7 ± 0.4 | −0.1 ± 0.4 | 0.06 | 0.18 |
| E' velocity (cm/sec) | 19 ± 6 | −1 ± 3 | 18 ± 5 | +0 ± 3 | 0.68 | 0.66 |
| E/E' ratio | 4.8 ± 1.4 | +0.2 ± 0.8 | 5.2 ± 1.4 | −0.3 ± 0.8 | 0.45 | 0.13 |
| IVRT (msec) | 84 ± 22 | −2 ± 13 | 71 ± 13 | +8 ± 12 | 0.06 | 0.05 |

Table 4 Legend:
Comparison of initial baselines and difference between first and second baselines in the two patient groups.
$B_1$: Initial baseline;
$B_2$ re-baseline after initial dobutamine test;
$\Delta(B_2 - B_1)$ - difference between second and first baselines.
P values:
a unpaired t-test between initial baselines ($B_1$) for two study groups;
b 2-way RMANOVA, interaction of baseline order and study drug (sildenafil versus placebo).
*p < 0.005 (within group, paired t-test between first and second baseline)
E - Early diastolic filling wave;
A - Atrial filling wave;
E' - mitral annular tissue velocity during early filling;
IVRT: Isovolumic relaxation time.

Changes between the first and second baseline data for placebo and sildenafil treatment groups are also provided in Table 4. There was a slight decline in arterial pressures and systemic vascular resistance along with a tandem increase in ejection fraction in subjects given sildenafil. Contractility also rose slightly in this group, which might have reflected a reflex response to the vasodilation, a direct effect, or slight residual dobutamine effects. Importantly, inter-group analysis found no significant influence of drug treatment (sildenafil versus placebo) on baseline contractility or diastolic function changes ($B_2 - B_1$, RMANOVA), but only on arterial resistance, with borderline changes in diastolic arterial pressure, and EF.

Example 13

Sildenafil Blunts Dobutamine-Stimulated Contractility

Figure 2:
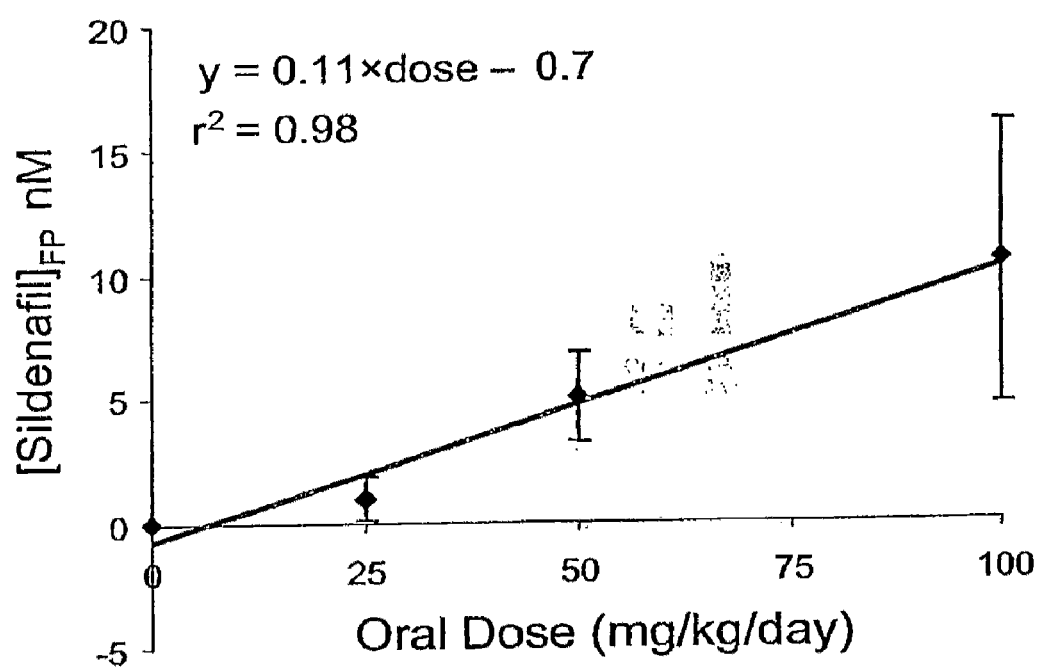
FIG. 2 is a dose response curve showing free plasma sildenafil concentrations in mice achieved at varying daily oral doses. At 100 mg/kg/day, the dose used for the studies outlined in FIG. 1 and throughout this application, free plasma sildenafil concentration was 10.4±5.7 nM, very near the $IC_{50}$ for the compound.
Figure 18:
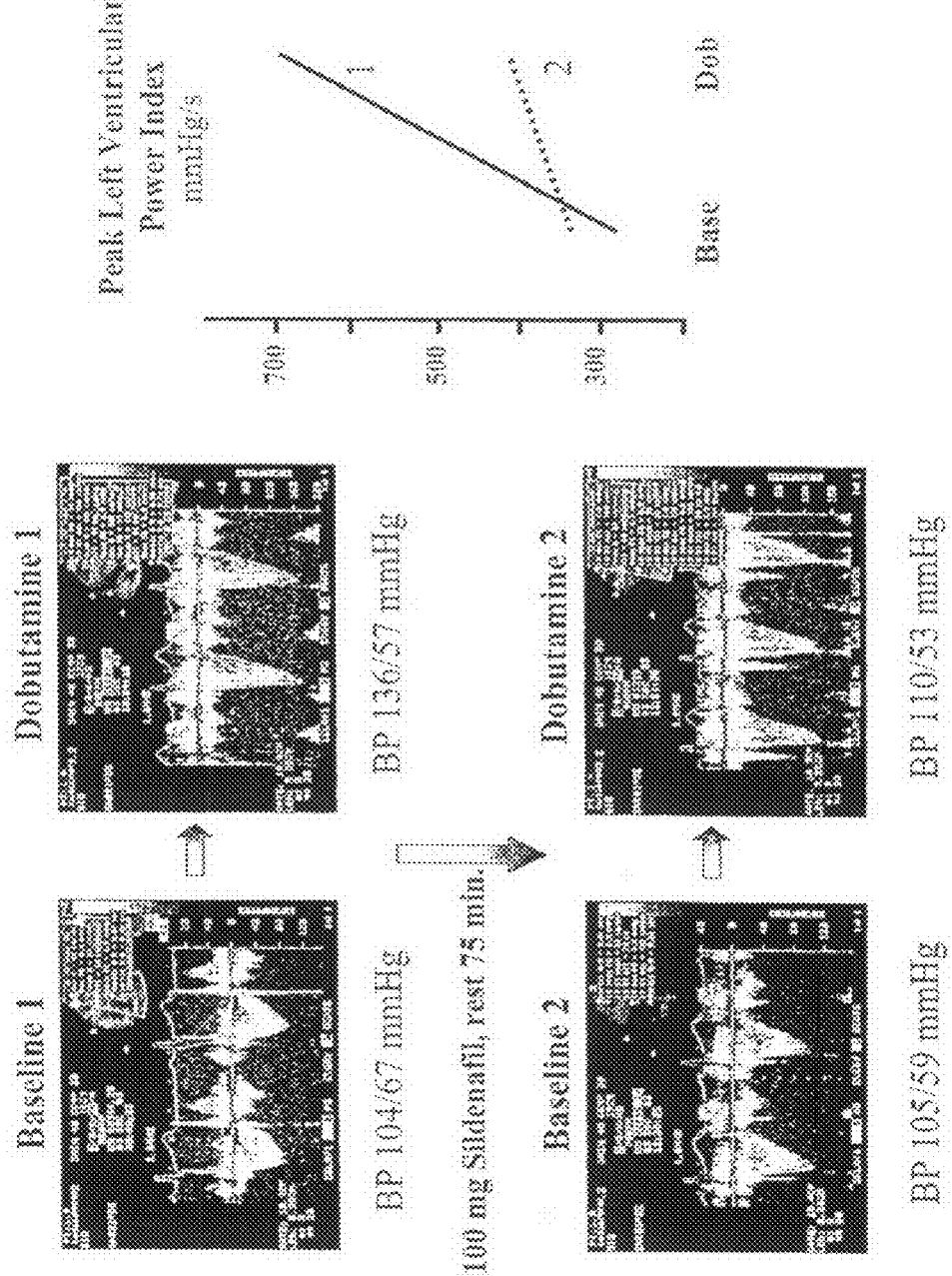
FIGS. 18A and 18B show data from a healthy human subject before and after stimulation with the β-adrenergic agonist-dobutamine, and with each such test performed before and after taking a single oral dose of sildenafil (100 mg, po).
Figure 19:
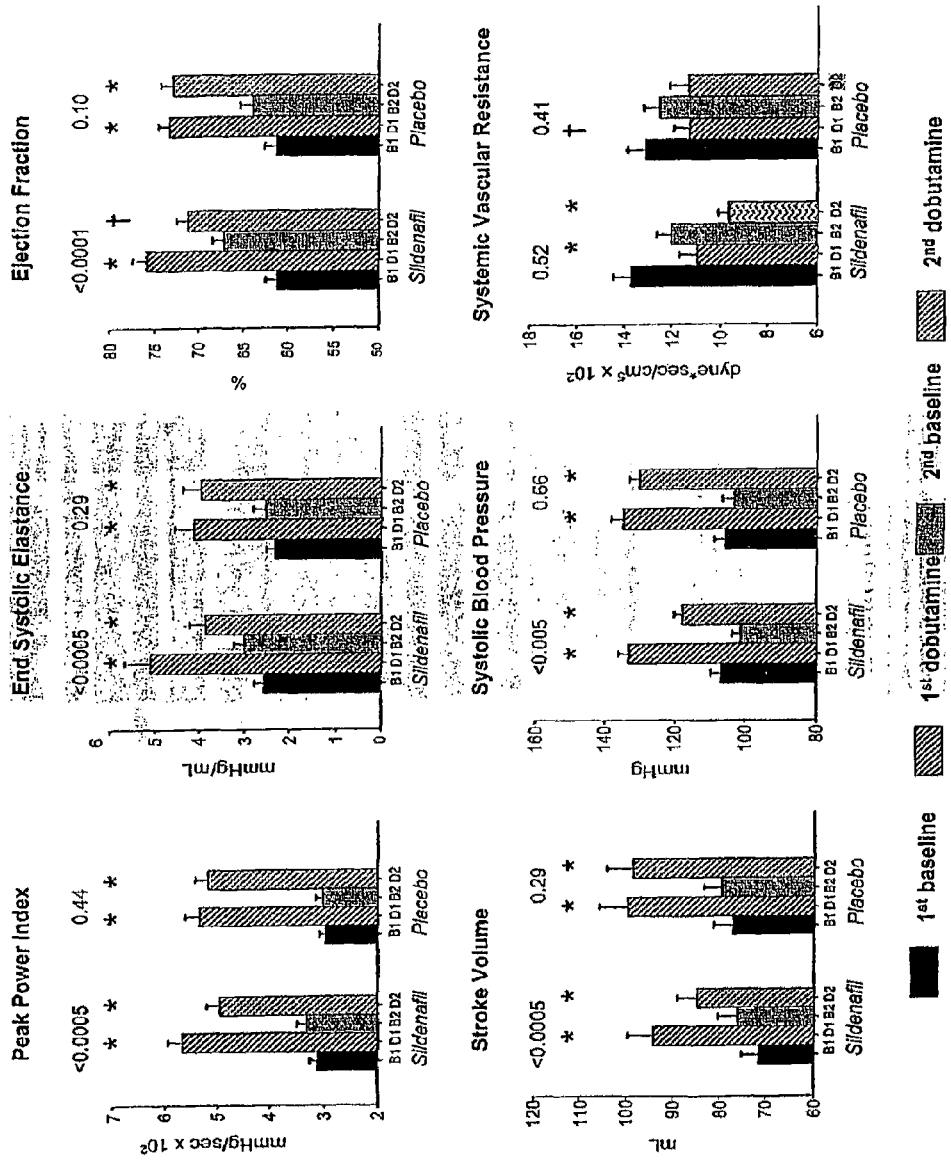
FIG. 19 is a series of six graphs showing absolute values for peak power index (peak LV power divided by end-diastolic volume), end systolic elastance, ejection fraction, stroke volume, systolic blood pressure and total peripheral resistance at each stage of the protocol. These provide a summary of results for a placebo controlled, double blind, randomized trial of sildenafil in healthy human volunteers. In each subject, a dobutamine stimulation challenge test was performed before and then after taking an oral study drug (placebo or sildenafil). $B_1$ and $B_2$ refer to the initial and second (i.e. after study drug) baselines, and $D_1$ and $D_2$ refer to data measured during dobutamine infusion before and after study drug, respectively. P values are from within-group RMANOVA testing for a change in the dobutamine-stimulated response before versus after receiving the study drug. Paired t-tests are also shown for within group comparisons of $D_1$ versus $B_1$ and $D_2$ versus $B_2$ (*$p<0.001$, †$p<0.005$ for this test). Sildenafil markedly reduced the dobutamine enhanced contractility as compared with placebo. There was no significant effect on total peripheral resistance however.
Figure 20:
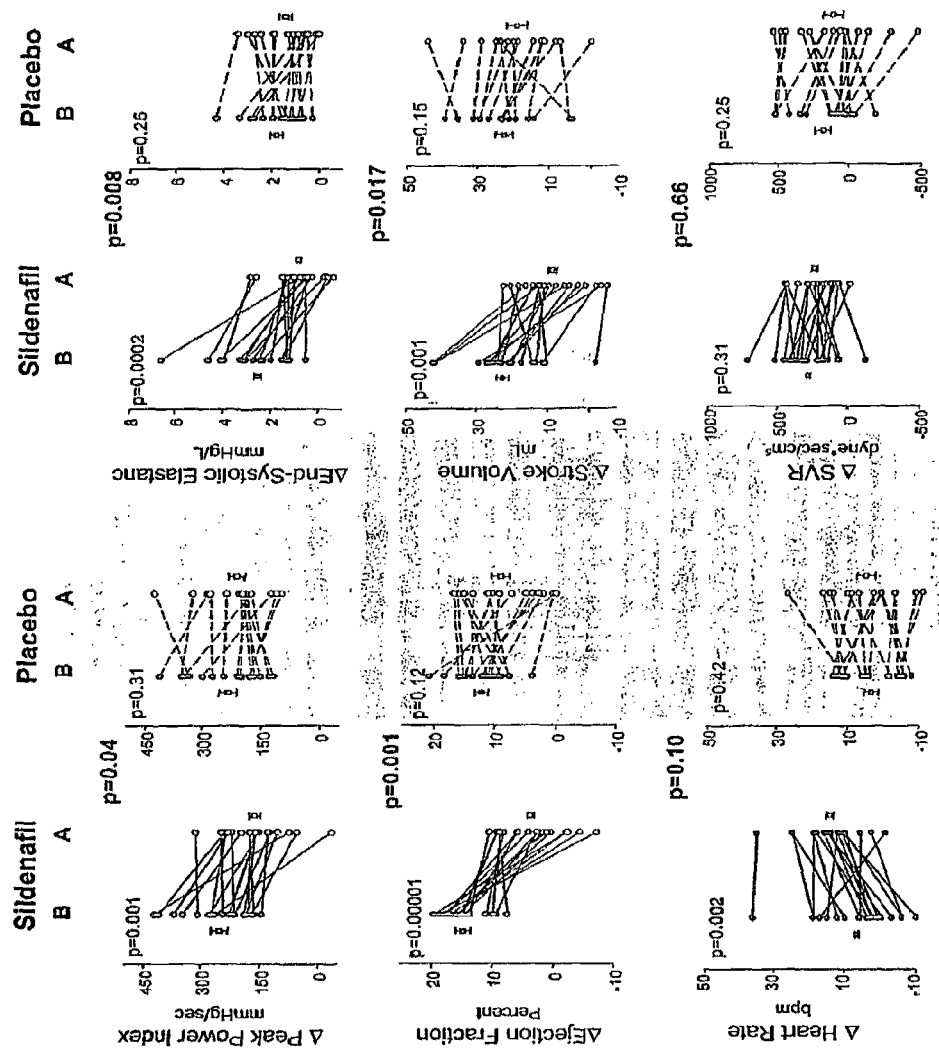
FIG. 20 is a series of twelve panels showing the change in hemodynamic function due to dobutamine before (B, •) versus after (A, ○) receipt of study drug—sildenafil or placebo. Within-group pairings for each patient are identified by the lines connecting data points. Mean values are shown by the boxes to the right or left of each data set. The p-values above each individual graph are for a comparison between the first and second dobutamine response (change versus baseline) in each group. The p-values in bold above each pair of plots is for RMANOVA based on a 3-way interaction of dobutamine test (pre or post study drug), dobutamine (present or not), and study drug (sildenafil vs placebo).

FIG. 1SA displays exemplary Doppler aortic flow data and corresponding pressures and calculated peak power index before and after dobutamine stimulation in a subject who received sildenafil as the study drug. Aortic flow and systolic pressure rose with the initial dobutamine test, increasing the power index by nearly 200%, whereas this response was substantially blunted in the same patient after they received oral sildenafil (FIG. 18B). Group data are shown in FIGS. 19 and 20. The systolic response to the first dobutamine test was identical in both groups (sildenafil versus placebo) and characterized by enhanced contractility and blood pressure along with reduced peripheral resistance. Contractile changes were largely reversed at the second baseline. After receiving the study drug, however, there were marked differences in the second dobutamine test with subjects receiving sildenafil displaying a diminished contractile response (FIG. 20). This change was not simply due to the slightly higher baseline in the sildenafil treated group (i.e. lowering net change), as peak responses (second versus first test) were themselves significantly reduced by sildenafil over placebo (p<0.015 for power index; p<0.01 for ejection fraction, and p<0.002 for end-systolic elastance). In contrast to contractility, the vasodilator response to dobutamine was unaltered. The p-values above each set of bars reflect within-group tests of study-drug effect on the dobutamine response.

FIG. 20 displays the results as absolute change in function induced by dobutamine before (first test) and after (second test) administration of the study drug. Data for each subject was paired. Peak power index rose+254±82 mmHg/s (from a baseline of ~300 mmHg/s before sildenafil treatment but by only 164±80 mmHg/s after (p=0.001), whereas changes before and after placebo were similar (236±89 vs 215±83 mmHg/s, p=0.31; p=0.04 for between group comparison). Similar findings were observed for mean power index (p=0.04), and for ventricular end-systolic elastance (2.52±1.5 vs 0.84±0.9 mmHg/ml, p<0.001 with sildenafil; 1.8±1.1 vs 1.4±1.1 mmHg/ml, p=0.25; with placebo; p=0.008 between groups). Dobutamine also increased ejection fraction by 15±3% (absolute change) before but only 4±5% after sildenafil (p<0.001), while in the placebo group, EF rose similarly with both tests (p=0.12; p=0.001 between groups). Similar differences were observed in the change in stroke volume induced by dobutamine.

Importantly, changes in contractile response were not due to altered vascular loading. The dobutamine-mediated drop in peripheral resistance was not modified by sildenafil (p=0.66, FIG. 3), and there was no difference between groups in cardiac preload (end-diastolic volume) at all stages of the study. End-systolic volumes declined with dobutamine, and this too was blunted in the sildenafil group compared to placebo (p=0.03). With the first dobutamine test, heart rate rose only modestly on average in both groups (3.5±7.7 and 6.7±2.2 bpm, placebo and sildenafil, respectively, FIG. 20), and even declined in some subjects. The latter was likely related to the low dose used which generated more contractile then chronotropic effects, but that elicited a reflex response to the rise in pressure and flow. After sildenafil, heart rate increased more with dobutamine (+14.5±4.7, p<0.01), but this did not reach statistical significance when compared by RMANOVA to the placebo group response (p=0.1).

Example 14

Effects on Diastolic Function

Table 5 provides the absolute change in diastolic function by dobutamine, before and after administration of the study drug.

TABLE 5

Influence of Sildenafil on Dobutamine-induced Changes in Diastolic Function

| Variable | Placebo | | Sildenafil | | p value- |
|---|---|---|---|---|---|
| | $D_1 - B_1$ | $D_2 - B_2$ | $D_1 - B_1$ | $D_2 - B_2$ | RMANOVA |
| E velocity (cm/sec) | 25 ± 10 | 21 ± 16 | 20 ± 18 | 12 ± 11‡ | 0.19 |
| A velocity (cm/s) | 5 ± 8 | 7 ± 11 | 5 ± 9 | 11 ± 7† | 0.33 |
| E/A ratio | 0.3 ± 0.3 | 0.2 ± 0.3 | 0.3 ± 0.3 | −0.1 ± 0.3* | 0.14 |
| E' velocity (cm/s) | 3.9 ± 2.3 | 2.9 ± 3.1 | 4.1 ± 3.4 | 1.5 ± 2.4* | 0.19 |
| E/E' ratio | −0.2 ± 0.9 | −0.3 ± 1.0 | +0.1 ± 0.8 | −0.2 ± 0.7 | 0.21 |
| IVRT | −28 ± 14 | −24 ± 15 | −17 ± 11 | −20 ± 13 | 0.30 |

Table 5. Data are for the change in each parameter comparing dobutamine stimulated to preceding baseline values for first ($D_1 - B_1$) and second ($D_2 - B_2$) dobutamine tests.
Within group paired t-tests:
*p < 0.01,
†p < 0.05,
‡p = 0.06.
The p-value is for a 3-way RMANOVA, testing for three way interaction between dobutamine test order (before or after receiving study drug), presence or absence of dobutamine, and treatment group (sildenafil vs placebo).
Abbreviations are as defined in Table 1.

For the first test, early (E) and late (A) diastolic filling rates rose similarly in both groups, and E/A ratio rose slightly. Sildenafil resulted in a borderline decline in E velocity (p=0.06), slightly raised A velocity (p=0.03), and thus decline in E/A ratio (p=0.007). Dobutamine-stimulated an increase in tissue Doppler. E' velocity was also blunted by sildenafil (p=0.002). Dobutamine's effect on E/E' ratio, an index of LV end-diastolic pressure, and isovolumic relaxation time were unaltered by the study drug in either group. Importantly, between-group analysis revealed no significant interaction of study drug on the dobutamine-change in diastolic function for any of the parameters (p values shown are for 3-way RMANOVA as used in the systolic analysis).

In the initial dobutamine test, systolic and diastolic function improved similarly in both treatment groups (e.g. peak power index rose 80±28%—placebo, 82±31%—sildenafil group, p=NS). In subjects who then received sildenafil, their second dobutamine response was significantly blunted, with peak power, ejection fraction, and end-systolic elastance changes all reduced by 32±34%, 66±64%, and 56±63%, respectively (each p<0.001 versus the initial response). This contrasted to the placebo group that displayed similar functional responses with both dobutamine tests. Sildenafil treatment did not significantly alter diastolic changes induced by dobutamine when compared to results with placebo. Thus, PDE5A inhibition by sildenafil blunts systolic responses to beta-adrenergic stimulation. This supports activity of PDE5A in the human heart and its role in modifying stimulated cardiac function.

This study reports the first direct evidence that sildenafil influences cardiac function in healthy humans, suppressing beta-adrenergic stimulated systolic function while having minimal effect under resting conditions. Importantly, this inhibitory effect did not depend on afterload or cardiac preload changes. This indicates that PDE5A inhibition can modify the cardiac stress response in humans.

PDE5A inhibitors have potent effects on vascular beds and tissues[61,62]. In addition, Sildenafil reduces pulmonary arterial resistance and may be effective in the treatment of pulmonary hypertension.[63,64] It also improves endothelial function, a marker of nitric oxide bioavailability and overall vascular health, in smokers[65] and patients with heart failure[66]. Animal studies have shown that sildenafil impressively reduces infarct size via an ischemic preconditioning-like effect.[67,68]

Following an early case report suggesting that PDE5A inhibitors might increase the risk of heart attack[69], several studies have attempted to define the cardiac effects of this class of drugs. In a study of 14 men with coronary artery disease, Herrmann, et al. reported that 100 mg of oral sildenafil slightly reduced resting systemic and pulmonary pressures, but had no effect on heart rate, left ventricular filling pressures or cardiac output.[54] In a subsequent study, men with known or suspected coronary disease underwent supine bicycle exercise testing, and sildenafil again slightly lowered blood pressure, but did not alter baseline or exercise-stimulated heart rate, blood pressure, exercise duration, or functional reserve.[56] Other investigations found only modest improvement in exercise performance[57] or prolongation of the time required to reach ischemic ST segment depression.[70]

Direct analysis of cardiac effects has been obtained in vitro, but these results remained limited and conflicting. PDE5A gene expression is present in human heart[52,59], although protein expression and enzyme activity have been questioned[51,53,71] Recent evidence has found that while gene and protein expression are indeed low, PDE5A is compartmentalized within the myocyte, and its inhibition is capable of altering heart and myocyte function. This is not observed under rest conditions, but only when the heart is stimulated, for example by beta-adrenergic agonists[58,59] or pressure overload[60]. Beta-stimulation co-activates adenylate cyclase to increase cyclic 3'5'-adenosine monophosphate (cAMP) as well as guanylate cyclase to generate cGMP.[72] The former activates protein kinase A, which enhances contractility by targeting calcium handling and myofilament interaction, whereas the latter acts as a "brake" to oppose this effect. This is achieved in part by activating dual-substrate PDEs that break down cAMP[73], and protein kinase G, which counteracts multiple cAMP/protein kinase A effects within heart cells.[72,74,75]

The results reported herein provide the first description of anti-adrenergic efficacy of PDE5a inhibition in humans. Cardiac function was studied both at rest and during adrenergic stimulation using various parameters specific to the heart and less dependent on changes in cardiac loading[76,77] Although re-baseline contractility was slightly (but significantly)

higher in the group receiving sildenafil, this did not explain the findings since the peak response was itself significantly lowered. Without wishing to be tied to one particular theory, these results cannot rule out a possible role of receptor desensitization due to sildenafil, although the prior evidence supporting a primary role of intracellular cGMP/PKG signaling[59] supports a more distal mechanism. The dobutamine-stress test rather than exercise was employed as this provided a more specific assessment of adrenergic regulation by sildenafil. Indeed, even healthy subjects acutely administered beta blockers display no change in overall exercise stress test performance or maximal cardiac output—despite clear effects on adrenergic stimulated contractility.[78] The cardiac power index provides a sensitive load-independent index of contractility[51-64,72,74,76,77,79-84] that is little influenced by arterial or venous vasodilation[76].

Unlike systolic changes, dobutamine-stimulated diastolic function was not significantly blunted by sildenafil treatment when compared between groups. Within group analysis did show that subjects that received sildenafil had an attenuated rise in early ventricular filling and relaxation (E and E' velocities, respectively) and greater increase in atrial filling (A velocity). While this could reflect a slight diminution in diastolic function, it is consistent with reduced contraction and increased end-systolic volumes with dobutamine infusion after sildenafil. This decline in net ventricular ejection could limit early diastolic recoil (suction) effects that contribute to early rapid filling of the heart. This in turn would result in augmented filling during atrial systole, particularly as end diastolic volumes were similar in both groups. The E/E' velocity ratio had been shown to correlate well with left ventricular diastolic pressure.[39] E/E' was similar in both groups at baseline or with dobutamine, and importantly there was no evidence that left ventricular diastolic pressure increased with sildenafil, despite blunted systolic augmentation. The sample size may also have contributed to the lack of diastolic effects, since noninvasive measures of diastole can have greater variance.

Sildenafil has been reported to increase sympathetic nerve activity without altering heart rate or blood pressure[85], and this could have played a role in the slight rise in basal contractility at second baseline in subjects receiving sildenafil. Such activity might be anticipated to down-regulate adrenergic stimulation, thereby blunting a dobutamine response. The changes were small but consistent with slight increases in plasma catecholamines with sildenafil (~70 pg/mL)[86], and about 3-4 orders of magnitude lower than that expected from dobutamine. Furthermore, there was no statistical difference in the between-group analysis. Sildenafil has also been reported to decrease vagal inhibition on heart rate[87] and in one study increased heart rate by nearly 10% after a single dose.[88] This may explain the enhanced heart rate response to dobutamine after sildenafil in this study. A higher heart rate per se would be expected to increase contractility, by the force-frequency relationship, whereas the opposite effect was true in this analysis of the sildenafil group.

Sildenafil can potently suppress adrenergic-stimulated contractility in the intact human heart. Previous studies have shown that Sildenafil and other PDE5A inhibitors are safe and effective for the treatment of erectile dysfunction in healthy individuals[80], patients with coronary disease[54,56], and patients with heart failure[57]. In contrast to previous reports that indicated that PDE5A inhibitors have no effect on the human heart, the results reported herein indicate that PDE5A inhibitors are important regulators of cardiac function in the presence of catecholamine stimulation. Blunting of adrenergic stimulation will likely prove beneficial for other disorders in which neurohormonal stimulation is enhanced, such as hypertension, left ventricular hypertrophy, and heart failure.

Example 15

PDE5A Inhibits Cardiac Molecular Remodeling

Figure 21:
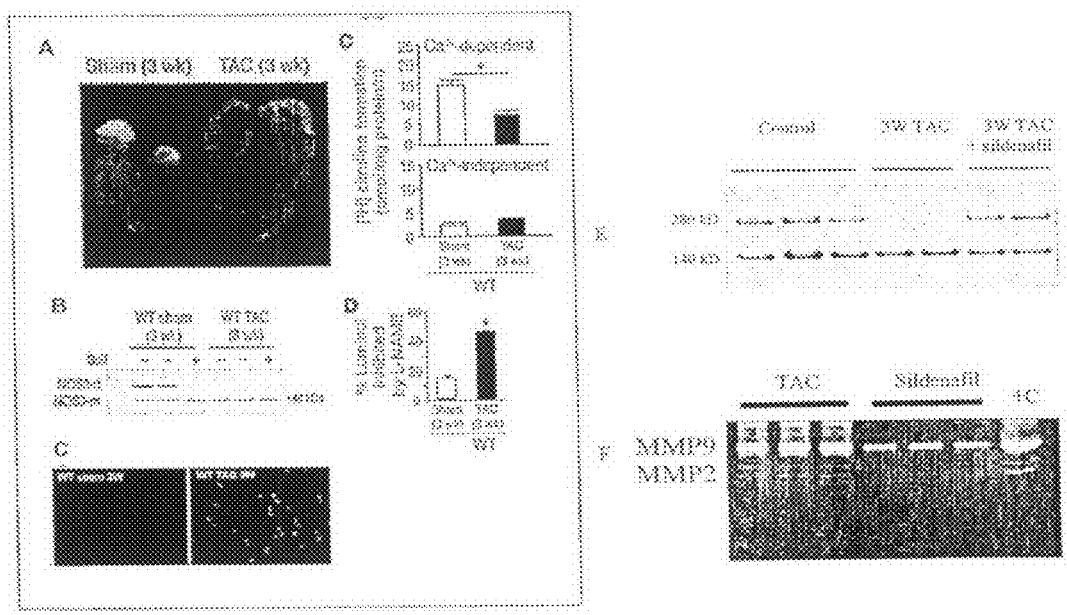
FIGS. 21A-21F show the effect of PdE5A inhibition on NOS3 coupling and metalloproteinase activation.

While the morphological changes in the heart are the most dramatic changes associated with cardiac remodeling, these morphological changes arise in response to earlier alterations gene transcription and protein activity (FIGS. 21A-F). PDE5A inhibition treatment prevents eNOS(NOS3) uncoupling and limits activation of metalloproteinases. Chronic aortic banding (TAC) results in loss of the normal dimer (higher mw form) of NOS3 (FIG. 21B). This resulted in activation of reactive oxygen species as shown in FIG. 21C. This figure shows positive staining detected by dihydroethidide. This is accompanied by a reduction in the calcium dependent NOS3 activity (FIG. 21C), and an increase in the amount of superoxide formed by NOS3 (FIG. 21D).

In addition, PDE5A inhibition prevents the loss of NOS dimer formation—supporting an important novel mechanism by which PDE5a inhibition can limit oxidant stress in the hypertrophied and failing heart (FIG. 21E). FIG. 21F shows that sildenafil inhibits the metalloproteinase activity of gelatinase. Marked gel lysis is observed with chronic TAC FIG. 21E (3W TAC). This activity is largely inhibited by co-treatment with sildenafil. Since activation of gelatinases are coupled to cardiac chamber remodeling and dilation, this indicates that that PDE5a inhibition can inhibit metalloproteinase's role in the molecular remodeling that is associated with heart failure and hypertrophy.

Figure 22A:
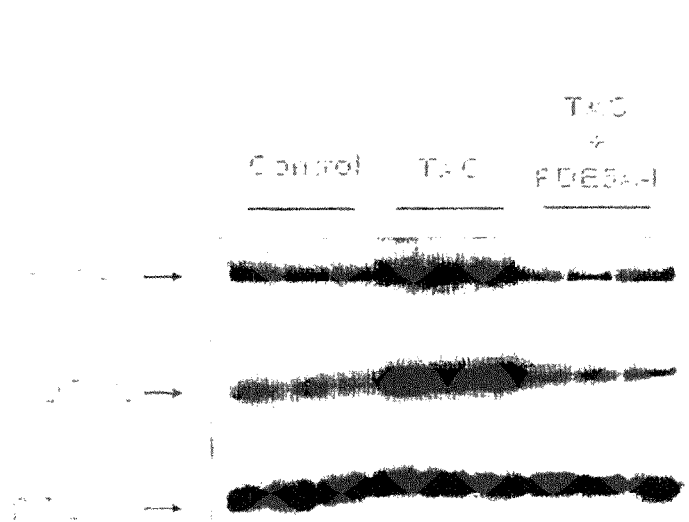
FIGS. 22A, 22B and 22C are a Western blot (FIG. 22A) and two summary graphs (FIGS. 22B and C) showing the effect of TAC and sildenafil treatment with TAC on the expression and activation of the small GTP-binding protein Rho A and its downstream kinase Rho kinase (ROCK 1 and ROCK 2).
Figure 22B:
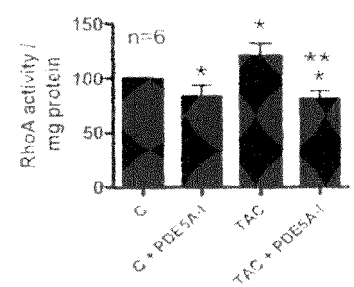
Figure 22C:
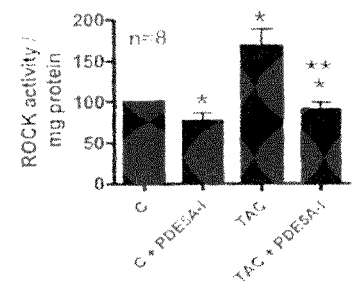

Increases in RhoA and Rho-kinase expression and activity are observed in chronic aortic banding (TAC) (FIGS. 21A-21C). Sildenafil inhibits RhoA, Rho-Kinase1 (ROCK1) and Rho-Kinase2 protein expression and activity (ROCK2) (FIGS. 22A-22C). Increases in rhoA and rho-kinase are associated with the molecular remodeling that precedes cardiac hypertrophy and dilation. By inhibiting alterations in these molecules, sildenafil is useful for the treatment of molecular remodeling.

Increases in STAT3 phosphorylation, which activate STAT3, are associated with TAC (FIGS. 23A and B). Sildenafil inhibits activation of STAT3 (FIG. 23A). Thus, sildenafil inhibits the molecular remodeling associated with alterations in STAT3 activity.

Example 16

Sildenafil Improves Myocardial Energetics

Figure 24:
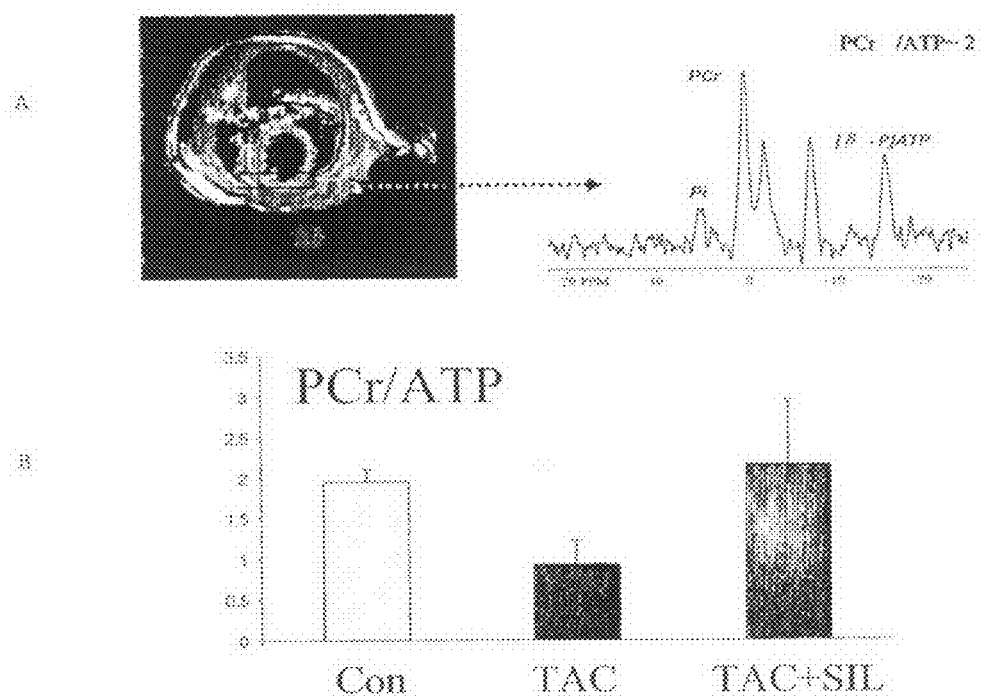
FIGS. 24A and 24B show that sildenafil treatment enhances myocardial energetics.

Sildenafil treatment improves myocardial energetics. Mice were exposed to TAC for three weeks. Hearts were then evaluated using in vivo NMR spectroscopy to assess high energy phosphate metabolism. An exemplary image and spectra are shown at FIGS. 24A and 24B. The ratio of phosphocreatine (PCr) to total ATP is used as a measure of energy reserve and balance. TAC significantly lowers this ratio, while treatment with sildenafil preserves the normal energy balance. This indicates that PDE5A inhibition improves myocardial energetics and enhances cardiac energy reserves under stress.

The results reported herein were carried out with the following materials and methods.

Animal Models

Male C57BL/6 mice (8-11 weeks, Jackson Laboratories) were used. Pressure overload was produced by transverse aortic constriction. Acute and chronic mortality of the banding procedure was <5%. Sham-operated mice underwent the same operation, but without aortic constriction. Oral treatment with PDE5 inhibitors was provided by mixing drug into semi-soft rodent chow (Bioserv; 4-6 g/day) that also provided full daily nutrition. Controls were treated with drug vehicle mixed in the food. Male transgenic mice with cardiac specific overexpression of a constitutively active Akt (16-20 weeks),[89] and litter mate controls were treated with vehicle or PDE5 inhibitor in the same way.

PDE5A Inhibitors

Sildenafil citrate (Viagra®, Pfizer), EMD 360527 (Merck KgA) and tadalafil (Clalis®, Eli Lilly) were used in the study. For in vivo chronic studies, 100 mg/kg/day of sildenafil was used yielding a mean free plasma concentration of 10.4±2.3 nM ($IC_{50}$ 5-10 nM). This is comparable to levels obtained in humans at 1 mg/kg/day, and reflects the near 100-fold higher metabolism of sildenafil in the mouse. 1.5 g/kg/day of EMD 360527 was used yielding a plasma concentration of 4 µM for EMD 360527 ($IC_{50}$ 1 µM in ex vivo vascular rings). 100 nM or 1 µM of sildenafil was used[58] for cGMP-PDE activity assay and neonatal rat cardiomyocytes studies. 50 nM of tadalafil was used in cGMP-PDE activity assay.

Physiological Studies

Transthoracic two-dimensional guided M-mode echocardiography was performed in non-anesthetized mice. Measurements were done using an echocardiography system, the SEQUOIA C256 (Siemens, Munich, Del.) with the 15 MHz linear-array transducer. Intact heart hemodynamic analysis was performed as described[90]. These studies employed a four-electrode pressure-volume catheter (model SPR-839, Millar Instruments) placed through the left ventricular apex in the open chest anesthetized animal and positioned along the longitudinal axis to record chamber volume by impedance and pressure by micromanometry.

RNA Dot Blot Analysis

RNA samples were prepared from snap-frozen hearts using a ready-to-use reagent for the isolation of total RNA TRIZOL reagent (Life Technology, Gaithersburg, Md.) according to the manufacturer's protocol. RNA dot-blot analysis was performed using a published protocol with a set of oligonucleotide probes[59]. Data are shown normalized to GAPDH measured for each respective sample.

Western Blotting

Protein was prepared from snap-frozen heart tissue using extraction buffer as described previously[90]. Antibodies included calcineurin (1:2000 dilution, BD Transduction Laboratories (San Diego, Calif.), GSK3β, Ser9-phospho-GSK313, Akt, Ser473-phospho-Akt, ERK, Thr202/Thr204-phospho-ERK (1:1000 dilution, Cell Signaling Technology, Beverly, Mass.). Primary antibody binding was visualized by horse radish peroxidase-conjugated secondary antibodies and enhanced chemiluminescence (Pierce, Rockford, Ill.).

Cyclic Nucleotide Assay

Hearts were washed in ice-cold PBS, homogenized in 6% trichloroacetic acid, centrifuged and extracted with water-saturated ether. The aqueous layer was transferred, vacuum dried, and the pellet resuspended in sodium acetate buffer for cAMP and cGMP enzyme immunoassay (Amersham Pharmacia Biotech, Buckinghamshire, UK).

PDE5A, PI3Kα, Akt, and PKG-1 Activity

Total low $K_m$ cGMP phosphodiesterase activity was assayed at 1 µM/L substrate using a fluorescence polarization assay (Molecular Devices) under linear conditions with and without PDE5A inhibitor (sildenafil 0.1-1 µM, or tadalafil 50 nM) or IBMX (50 µM). PDE-assays at 1 µM cGMP detected several high affinity cGMP-PDEs (PDE5A, PDE9A) and dual specificity PDEs (e.g., PDE1C, PDE3A, PDE10A and PDE11A). PI3Kα activity was assessed by Elisa assay following immunoprecipitation of PI3K (Seize X IP Kit, Pierce) using a p85α monoclonal antibody (Cell Signaling), with activity measured by fluorescence polarization (Molecular Devices, Perkin-Elmer Victor 3 plate reader). Akt activity (IP with s473-pAkt Ab, GSK-3 fusion protein substrate) was performed using a commercial kit (Cell Signaling Technology, Beverly, Mass.). PKG-1 activity was assayed by calorimetric analysis, CycLex (Clinisciences, Montrouge, FR) from whole heart lysates.

Histology

Hearts were fixed with 10% formalin overnight, then embedded in paraffin, sectioned at 5 µm thickness and stained with PAS methenamine. Cardiomyocyte diameter and interstitial collagen fraction were determined using computer-assisted image analysis (Adobe Photoshop 5.0, NIH Image J), with the observer blinded as to tissue source. At least 4-5 different hearts, with five separate fields of cells (total 50-70 cells for each heart) were quantified for cellular analysis.

Neonatal Rat Cardiac Myocyte Studies

Rat neonatal cardiac myocytes were isolated from 1- to 2-day-old Sprague-Dawley rats as described[50]. Cell cultures were stimulated by forty-eight hour incubation with phenylephrine (PE; 1 µM; Sigma Chemical (St. Louis, Mo.) or BayK8644 (1 µM; Sigma) in the presence or absence of co-incubation with sildenafil 100 nM or 1 µM. To assess NFAT activation, cells were transfected with adenovirus expressing the three NFAT-binding sites linked to β-galactosidase (p3xNFAT-GL), using previously described methods[72]. Additional studies were performed using an alternative reporter adenovirus encoding luciferase driven by the NFAT promoter. This was performed twenty-four hours prior to PE, BayK8644, or activated calcineurin stimulation. The latter was achieved by a co-transfection with a replication-deficient adenovirus encoding a $Ca^{2+}$-independent, constitutively active, truncated mouse calcineurin A (AdCnA[72]). Transfection was performed at a MOI of 100 PFU in 2 mL (6-cm culture dishes) DMEM for two hours at 37° C. in a humidified, 5% $CO_2$ incubator after which the medium was replaced with medium containing 1 µM sildenafil or vehicle. After an additional forty-eight hours, NFAT activation was assessed by β-galactosidase histology/activity or luciferase activity. Myocytes were fixed in 2% paraformaldehyde and 0.2% glutaraldehyde in PBS for 10 minutes, incubated in X-gal stain (in PBS, 20 mmol/L $K_4Fe[CN]_6 3H_2O$, 20 mmol/L $K_3Fe[CN]_6$, 2 mmol/L $MgCl_2$, and 1 mg/mL X-gal [Promega] in DMSO) for two hours at 24° C., rinsed in PBS, and postfixed in 7% buffered formalin for six hours. β-galactosidase activity was assayed using a commercial test kit (Galacto-Light Plus, Applied Biosystems) with light emission measured by microplate luminometer (Turner Biosystems, Sunnyvale, Calif.). Luciferase activity was assayed by commercial kit (Stratagene, La Jolla, Calif.) and read on a plate luminometer.

$^3H[\ ]$-Leucine Incorporation

Twenty-four hours after the onset of serum starvation, neonatal cardiac myocytes were incubated in triplicate in 12-well plates with 1 µM PE in the presence or absence of sildenafil (100 nM or 1 µM) for twenty-four hours and then incubated in the same medium with 1.0 µCi/ml [$^3H$]-leucine for an additional twelve hours. The medium was aspirated and the cells were washed with ice-cold PBS and fixed on ice for 30 minutes with cold 10% trichloroacetic acid (TCA). After washing twice with 5% TCA, and once with water, the radioactivity incorporated into the TCA-precipitable material was determined by liquid scintillation counting after solubilization in 0.25 M NaOH.

Statistical Analysis

Data were expressed as mean±sem. Differences between multiple groups were compared by ANOVA followed by a Tukey's multiple comparisons test. Two-group analysis was performed by t-test (paired or unpaired as appropriate). Serial studies ere tested by repeated measures ANOVA.

Specific Hemodynamic Index Methods:

All hemodynamic data were recorded using custom developed software, digitizing signals at 2 KHz. End-diastolic and end-systolic volumes were the average of volumes measured during isovolumic contraction and relaxation, respectively. ESP was the pressure at maximal chamber elastance (P/V ratio)[1]. EDP was the diastolic pressure at the lower right hand corner of the pressure-volume loop. Cardiac output was determined from a perivascular flow probe (Transonics, Ithica, N.Y.) placed around the thoracic aorta. Ea was equal to the ratio of end-systolic pressure divided by stroke volume. The volume catheter signal was calibrated for both gain and offset. Gain was determined by setting the catheter-derived cardiac output (equal to pressure-volume loop width times heart rate) to that obtained from the calibrated flow probe value. Offset was determined using the hypertonic saline method Ventricular power was equal to the instantaneous product of pressure times flow, and the peak power was divided by EDV to obtain the power index PMXI[79]. $Ees_n$ was obtained by the set of end-systolic pressure-volume points (maximal P/[V–Vo]) measured during transient inferior vena caval occlusion. The slope of this relation Ees was normalized by heart mass and expressed per gm heart mass. Msw was derived from the linear relation between stroke work and EDV from the same set of variably loaded cardiac cycles used to derive $Ees_n$, and is another load-independent assessment of systolic contractile function[4]. Tau was obtained from the model: $P = P_o + ae^{-t/\square}$ ... fitting data during isovolumic relaxation. dP/dt was derived from a digital filter (5-point weighted slope). PFR/EDV was derived from the maximal first derivative of the volume signal during early diastole, divided by EDV.

Animal Studies for Examples 7-11

Male wild type and NOS3$^{-/-}$ mice (C57BL6, Jackson Labs, 6-8 wks) were studied. PDE5A was inhibited in vivo with sildenafil (100 μg/kg/min; 37±5.2 nM free plasma concentration); or EMD-360527/5 (Merck KgA, Germany, 160-300 μg/kg/min). Both compounds have an $IC_{50}$ of ~10 nM for purified PDE5A (vs 1-20 μM for PDE1 or PDE3). In vitro studies used 0.1-1 μM sildenafil (SIL), 0.05 μM tadalafil (prepared in 1×PBS), or 0.1 μM EMD-360527/5 in buffered 1% propanediol. In vivo and in vitro studies of vehicles alone confirmed no effects.

In Vivo Studies

Isoproterenol (ISO: 20 ng/kg/minutes i.v.×5 min) with or without PDE5A inhibitor was given to anesthetized intact mice, and in vivo heart function assessed by pressure-volume relations at a fixed atrial pacing rate of 600-650 min$^{-1}$. Data were measured at baseline, with ISO, re-baseline, PDE5A-inhibition, and PDE5A inhibition+ISO. The ISO-only response was highly reproducible.

Isolated Myocyte Studies

Excised hearts were retroperfused by buffer containing BDM (1 mg/ml) and taurine (0.628 mg/ml) for 3 min, 0.9 mg/ml collagenase (Worthington Biochemical Co., Lakewood, N.J., type 2; 299 U/mg) and 0.05 mg/ml protease (Sigma Chemical, St. Louis, Mo.) for 6-7 min. Ventricles were gently chopped, filtered (150μ mesh), centrifuged (500 RPM×1 min), and rinsed in Tyrode's solution with increasing calcium (final 1.8 mM $Ca^{2+}$). Cells were incubated with 5 μM Indo-1 AM (Molecular Probes), rinsed, and studied at 27° C. by field stimulation in an inverted fluorescence microscope (Diaphot 200; Nikon, Inc). Sarcomere length (IonOptix, MA) and whole cell calcium transients were measured. Following baseline, cells were exposed to 10 nM ISO, then ISO+SIL, or ISO+EMD-360527/5 at pH 7.45. SIL was diluted in 0.1% DMSO and EMD in 0.001% propanediol; control solutions contained similar vehicle concentrations.

Gene and Protein Expression

PDE5A gene expression was assessed by quantitative real-time PCR. Residual genomic DNA was removed from mRNA by treatment with DNase I, and cDNA synthesized with the SuperScript First-Strand Synthesis System for RT-PCR (Invitrogen). Relative abundance of PDE5A mRNA was determined by SYBR Green I assay (QuantiTect SYBR Green PCR, Qiagen), using the following primers: PDE5A (GenBank: NM_153422.1) upper-primer-1493 5'-TGAGCAGT-TCCTGGAAGCCT-3' (SEQ ID NO:1), lower-primer-1596 5'-ATGTCACCATCTGCTTGGCC-3' (SEC) ID NO:2), product 104 bp; GAPDH (NM_008084.1) upper-primer-263 5'-ACCATCTTCCAGGAGCGAGAC-3' (SEQ ID NO:3), lower-primer-363 5'-GCCTTCTCCATGGTGGTGAA-3' (SEQ ID NO:4), product 101 bp; with a GeneAmp 5700 Sequence Detection System (Applied Biosystems). PCR samples were run in triplicate, and GAPDH content used to normalize PDE5A content of different samples. Reactions (20 μl) were performed with 300 nM of the specific primer pairs for 40 cycles of amplification (denaturation at 95° C. for 15 s, annealing at 60° C. for 30 s, and extension at 72° C. for 30 s). Amplification specificity of PCR products was confirmed by melting curve analysis[24]. Subsequent to the final PCR cycle, reactions were heat denatured over a 35° C. temperature gradient at 0.03° C/s from 60-95° C.

Protein lysates from whole myocardium and isolated cardiac myocytes were extracted in lysis buffer (#9803, Cell Signaling Technology, Beverly, Mass.) with mini-protease inhibitor (#1-836-153, Roche, 1N) and 5% Triton (Sigma). Following 12,000 g centrifugation for thirty minutes, protein was quantified (#23235, Pierce, Rockford, Ill.), NUPage LDS sample buffer added (#161-0737, Biorad, Hercules, Calif.), and lysates electrophoresed on NuPAGE 4-12% Bis-Tris polyacrylamide gels (Invitrogen, San Diego, Calif.). Membranes were incubated with rabbit polyclonal antibodies raised against purified bovine lung PDE5A (Cell Signaling, MA) [1:5,000], the amino terminal PDE5A domain (gift from Mauro Giorgi) [1:5,000], or recombinant PDE5A [1:10,000].

Fluorescence Resonance Energy Transfer (FRET) Imaging

Ventricular myocytes from 1-2 days old Sprague Dawley rats (CharlesRiver Lab, MA) were prepared and transfected with the vector carrying the cGMP sensor cygnet-2.1[77] in which EYFP was substituted with the less pH sensitive variant citrine[89], and imaged eighteen-twenty-four hours after transfection as described[90]. Images (50-80 ms exposure) were acquired every 10 seconds using custom software and processed by Imagej (NIH, MD). FRET was the change in 480 nm/545 nm emission intensities (ΔR) upon 430 nm excitation[91] expressed as percent change over the basal intensity ($R_0$). Cells were bathed in HEPES buffered Ringer's modified saline (1 mmol/L $CaCl_2$), at room temperature (20-22° C.).

PDE5A and PKG-1 Activity Analysis

Total low $K_m$ cGMP phosphodiesterase activity was assayed at 1 μMol/L substrate by fluorescence polarization (Molecular Devices, CA) under linear conditions, or a 2-step radiolabeled method[18], with or without added sildenafil (0.1-1 μM), tadalafil (50 nM), or IBMX (50 μM). PDE-assays at 1 μM cGMP detected several high affinity cGMP-PDEs (PDE5A, PDE9A) and dual specificity PDEs (e.g., PDE1C, PDE3A, PDE10A and PDE11A).

PKG-1 activity was assayed by colorimetric analysis (CycLex, Nagano, Japan) performed in whole myocytes incubated with or without added ISO (10 nM), SIL (1 □M), tadalafil (50 nM), or sGC inhibitor ODQ (3 □M, Sigma). After 10 min, cells were lysed and PKG-1 activity determined.

Immunofluorescent Histology

Wild-type cardiomyocytes were fixed in 50% methanol/50% acetone, and incubated overnight with sequence-specific PDE5A antibody (gift of K. Omori) at 1:5,000 dilution and either mouse monoclonal α-actinin (1:500 dilution; Chemicon Intern. CA), or NOS3 (1:3000; Transduction Labs, KY). Secondary incubation used anti-rabbit Alexa 488 and anti-mouse Alexa 546 (Molecular Probes, OR) (1 hours, 27° C.). Cells were imaged on a Zeiss inverted epifluorescence microscope with argon-krypton laser confocal scanning system (UltraVIEW, PerkinElmer Life Sciences, MA).

Human Studies

Forty healthy volunteers were recruited from the general population in response to advertisements posted in the surrounding community. Subjects were screened by medical history, physical examination, and transthoracic echocardiogram. Individuals with heart disease, atherosclerosis, hypertension, diabetes mellitus, pulmonary hypertension, renal or hepatic disease, smoking, pregnancy, or under treatment with nitrates, adrenergic-blocking drugs, or medicines known to interfere with sildenafil pharmacokinetics were excluded. The study design followed a randomized, double-blind, placebo-controlled protocol, using a 3:2 assignment ratio that favored sildenafil. All subjects were instructed to fast for >6 hours prior to study. An intravenous cannula was placed in the forearm, and 15-20 minutes later, initial baseline ($B_1$) measurements of blood pressure, electrocardiogram, and echo-Doppler assessment of heart function were obtained in the supine position. Intravenous dobutamine (5 μg/kg/min) was then administered for 5 minutes to achieve a stable response, and measurements repeated ($D_1$). Dobutamine was discontinued, and 15 minutes provided to return to the baseline state. Subjects then received either 100 mg oral sildenafil or placebo. After 75 minutes (mean time to peak level)[82], a blood sample was obtained to confirm sildenafil level. Data were again recorded for a second baseline (B2), and during a second dobutamine infusion ($D_2$) using the identical protocol as for the first test.

Heart Function Analysis

Systolic function was determined by cardiac-specific indexes that combined measurements of pressure, dimension, and flow. Arterial pressure was determined by an oscillometric arm cuff (Dinemap, Critikon, Tampa, Fla.), and 2-dimensional echo-Doppler measurements by an Agilent Sonos 5500 (Philips, The Netherlands) employing a 3 MHz probe. All echo-Doppler measurements were digitally acquired to optical disc and analyzed offline by a single blinded investigator. Each measurement reflected the average of at least 3 separate beats. Aortic flow was equal to the velocity time-integral from pulse-wave Doppler in the left ventricular outflow tract multiplied by cross sectional diameter.[83] Stroke volume, peak, and mean flow were determined from this waveform. Cardiac output was the product of heart rate and stroke volume. Systemic vascular resistance was the ratio of mean arterial pressure (⅓ pulse pressure+diastolic blood pressure) to cardiac output.

Cardiac contractility was assessed by several load-independent indexes. The primary outcome variable was peak power index (maximal power divided by end-diastolic volume), which reflects heart contractile state independent of afterload and preload as previously demonstrated.[76,77,84] Maximal power was approximated by the product of peak aortic flow and systolic pressure, which strongly correlates with the maximal instantaneous product of pressure and flow ($y=1.08x+0.002$, $r^2=0.97$, $p<0.0001$; based on analysis of reported invasive data from patients with a broad range of heart conditions[77]). Load-independent secondary outcome contractility parameters were mean ventricular power index and the end-systolic pressure/volume ratio, an approximation for ventricular end systolic elastance.

Other secondary outcome variables included routine measures of cardiac systolic and diastolic function. Ejection fraction was determined from cardiac end-diastolic and systolic volumes determined by Simpson's method using apical 4- and 2-chamber views. End-diastolic volume was equal to stroke volume (from Doppler) divided by ejection fraction, with end-systolic volume equal to the difference of the former and latter. Pulse-wave Doppler spectra of transmittal inflow and tissue Doppler imaging of the lateral mitral annular (E') velocities were used to assess diastolic function.[89] The ratio of E/E' was determined as a surrogate marker of left ventricular filling pressures as previously validated[90]. Isovolumic relaxation time was measured by continuous wave Doppler as the time between aortic flow cessation and onset of mitral inflow.

Plasma Sildenafil Levels

Plasma sildenafil and its metabolite desmethylsildenafil were measured in each subject by liquid chromatography and mass spectrometry (SFBC Analytical Labs, North Wales, Pa.).

Statistical Analysis

Sample size estimates were set to detect a>20% decline in peak left ventricular power index in response to dobutamine, with an $\alpha=0.05$ and 80% power. In prior animal studies, dobutamine-stimulated power declines ~50% with PDE5A inhibition, and for humans, dobutamine increases power by >100% from a baseline of ~300 mmHg/sec[76]. To detect a 20% decline in this response (60 mmHg/sec) with a standard deviation of 50 mmHg/sec (from prior data), a sample size of 15 placebo controls and 23 sildenafil treated subjects was estimated.

All statistical analysis was performed using Systat® software. Results are expressed as mean±standard deviation. Hemodynamic data were analyzed using a three-way repeated measures ANOVA, with the three grouping factors being: 1) presence or absence of dobutamine; 2) placebo versus sildenafil; and 3) first versus second dobutamine challenge study. The primary test was a test between group analysis of whether sildenafil (versus placebo) altered the disparity between the first and second dobutamine response, and determined by a three-way interaction term that included each grouping factor. This model also included a term testing for an overall effect of sildenafil (versus placebo) that did not solely relate to the relative dobutamine response. Within group analysis was also performed using a 2-tailed Student's paired t-test to assess individual dobutamine responses (i.e. $D_1$-$B_1$; $D_2$-$B_2$), and a 2-way ANOVA to test whether study drug altered this response within in each group. Categorical variables were compared using the Chi-squared test.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

DHE Staining Method

Fresh frozen LV myocardium (8 μm slices) was incubated for 1 hour at 37° C. with dihydroethidium (DHE; Molecular Probes, Eugene, Ore; 2 μM) which assesses $O_2$— formation (typically nuclear localization). Imaging was performed on a Zeiss inverted epifluorescence microscope attached to an argon-krypton laser confocal scanning microscope (Ultra-VIEW, Perkin Elmer Life Sciences, Inc.). The excitation/emission spectrum for DHE was 488 and 610 nm, respectively, with detection at 585-nm.

Cardiac Gelatinase Analysis

In Vitro gelatin lysis by MMP-2 and MMP-9 was assessed by zymography. Briefly, modified Laemmli buffer without mercaptoethanol was added to lysed tissue samples and loaded on 10% gelatin (Invitrogen Corp., San Diego, Calif.). After electrophoresis, gels were washed twice with renaturing buffer at room temperature followed by developing buffer (Invitrogen Corp., San Diego, Calif.), then stained with a commercially available Coomassie stain to visualize lytic bands (SIMPLYBLUe, Invitrogen Corp., San Diego, Calif.).

RboA Activity Assay

RhoA activity assay was performed by immunoprecipitation using a commercially available immobilized antibody (SEIZE X IP, Pierce Biotechnology, IL). The antibody used was a rabbit polyclonal antibody raised against RboA (Upstate, NY [1:2500]) and subsequent commercial activity assay according to manufacturer's specification (Upstate Biotechnology, NY).

Western Analysis

Protein lysates from whole myocardium and isolated cardiac myocytes were obtained using lysis buffer (Cell Signaling Technology, Beverly, Mass.) with mini-protease inhibitor (Roche, Ind.) and 5% Triton (Sigma Chemical (St. Louis, Mo.). Following 12,000 g centrifugation for 30 minutes, protein was quantified (Pierce Rockford, Ill.), NUPage LDS sample buffer added (Biorad, Hercules, Calif.), and lysates electrophoresed on NuPAGE 4-12% Bis-Tris polyacrylamide gels (Invitrogen, San Diego, Calif.). Membranes were incubated with rabbit polyclonal antibodies raised against ROCK1 or ROCK2 (Cell Signaling Technology, Beverly, Mass.) [1:3,000].

STAT3 Activation Studies:

Myocardial tissue extract was electrophoresed in SDS-New Page gel, and probed for both tyrosine phosphorylated (Tyr705) and total Stat3. In additional studies, rat neonatal myocytes were cultured, then exposed to interleukin 6 (IL-6, Cell Signaling, 100 ng/ml) for one hour. In some studies, cells were pre-treated with sildenafil (1 μM) for 30 minutes prior to IL-6, and then during IL-6 exposure as well. In other studies, cells were pre-transfected (Lipofectamine™, Invitrogen) with mixed oligonucleotide silencing RNAs for STAT3 (siRNA, SmarTTpool Stat3). Protein extracts were obtained from myocyte extracts after the 1 hour incubation period, and probed for phosphorylated and total protein levels of Stat1 (Tyr701) and Stat3 (Tyr705) (Cell Signaling Inc.). siRNA was transfected into neonatal myocytes.

Other Embodiments

From the foregoing description, it will be apparent that variations and modifications may be made to the invention described herein to adopt it to various usages and conditions. Such embodiments are also within the scope of the following claims. All patents and publications mentioned in this specification are herein incorporated by reference to the same extent as if each independent patent and publication was specifically and individually indicated to be incorporated by reference.

REFERENCES

1. Senazaki, et al., (2001) FASEB J. 15:1718-1726
2. Molkentin, et al., (1998) Cell 93:215-228
3. Semeniuk, et al., (2003) Am. J. Physiol Heart Circ. Physiol 284:H425-H430
4. Fiedler, et al., (2002) Proc. Natl. Acad. Sci. U.S.A. 99:11363-11368
5. Bueno, et al., (2002) Circ. Res. 91:776-781
6. Minamino, et al., (2002) Proc. Natl. Acad. Sci. U.S.A. 99:3866-3871
7. Zou, et al., (2001) Circulation 104:102-108
8. Bueno, et al., (2000) EMBO J 19:6341-6350
9. Condorelli, et al., (2002) Proc. Natl. Acad. Sci. U.S.A. 99:12333-12338
10. Matsui, et al., (2002) J. Biol. Chem. 277:22896-22901
11. Matsui, et al., (2003) Cell Cycle 2:220-223
12. Oudit, et al., (2004) J. Mol. Cell. Cardiol 37:449-471
13. Crackower, et al., (2002) Cell 110:737-749
14. Patrucco, et al., (2004) Cell 118:375-387
15. Hardt, et al., (2002) Circ. Res 90:1055-1063
16. Juhaszova, et al., (2004) J. Clin. Invest 113:1535-1549
17. Tanji, et al., (2002) J. Biol. Chem. 277:36955-36961
18. Shin, et al., (2002) Exp. Mol. Med. 34:444-450
19. Antos, et al., (2002) Proc. Natl. Acad. Sci. U.S.A. 99:907-912
20. Corbin, et al., (2003) Curr. Med. Res. Opin. 19:747-752
21. Takimoto, et al., (2004) Circ Res. In Press
22. Kim, et al., (2001) Circulation 104:2338-2343
23. Ni, et al., (2004) J. Am. Soc. Nephrol. 15:1254-1260
24. Rybalkin, et al., (2003) EMBO J. 22:469-478
25. Francis, et al., (2002) J. Biol. Chem. 277:47581-47587
26. Massion, et al., (2003) Circ. Res. 93:388-398
27. Champion, et al. (2004) Circ. Res. 94:657-668
28. Knowles, et al. (2001) J. Clin. Invest 107:975-984
29. Holtwick, et al., (2003) J. Clinic Invest 111:1399-1407
30. Oliver, et al., (1997) Proc. Natl. Acad. Sci. U.S.A. 94:
31. Zahabi, et al., (2003) J. Biol. Chem. 278:47694-47699
32. Kotera, et al., (2003) Biochem J. 372:419-426
33. Wollert, et al., (2002) Hypertension 39:87-92
34. Pilz, et al., (2003) Circ. Res. 93:1034-1046
35. De Windt, et al., (2000) J. Biol. Chem. 275:13571-13579
36. De Windt, et al., (2000) Circ. Res. 86:255-263
37. Esposito, et al., (2002) Circulation 105:85-92
38. Wilkins, et al., (2004) Circ. Res. 94:110-118
39. Michael, et al., (2004) J. Biol. Chem. 279-21383-21393
40. Sastry, et al., (2004) J. Am. Coll. Cardiol. 43:1149-1153
41. Senzaki, et al., (2001) FASEB J. 15:1718-1726
42. Giordano, et al., (2001) Biochem Biophys Acta. 1539: 16-27
43. Kotera, et al., (2000) J Histochem Cytochem. 48:685-693
44. Loughney, et al. (1998) Gene. 216:139-147
45. Corbin, et al., (2003) Curr. Med. Res. Opin. 19:747-752

46. Cremers, et al., (2003) J. Cardiovasc Pharmacol. 41:734-743
47. Herrmann, et al., (2000) N Engl J Med. 342:1622-1626
48. Kishimoto, et al., (2001) Proc Natl Acad Sci U.S.A. 98:2703-2706
49. Holtwick, et al., (2003) J Clin Invest. 111:1399-1407
50. Wollert, et al., (2002) Hypertension 39:87-92
51. Corbin, et al., (2003) Curr Med Res Opin. 19:747-752
52. Loughney, et al., (1998) Gene. 216:139-147
53. Wallis, et al., (1999) Am J. Cardiol. 83:3C-12C
54. Herrmann, et al., (2000) N Engl J Med. 342:1622-1626
55. Jackson, et al., (1999) Am J Cardiol. 83:13C-20C
56. Arruda Olson, et al., (2002) JAMA 287:719-725
57. Bocchi, et al., (2002) Circulation 106:1097-1103
58. Senzaki, et al., (2002) FASEB J 15:1718-1726
59. Takimoto, et al., (2005) Circ Res. 96:100-109
60. Takimoto, et al., (2005) Nat Med. 11:214-222
61. Raja, et al., (2004) Ann Thora Surg. 78:1496-1506
62. Reffelmann, et al., (2003) Circulation 108:239-244
63. Humbert, et al., (2004) N Engl J. Med. 351:1425-1436
64. Michelakis, et al., (2003) Circulation 108:2006-2069
65. Kimura, et al., (2003) Hypertension 41:1106-1110
66. Katz, et al., (2000) J Am Coll Cardiol 36:845-851
67. Salloum, et al. (2003) Circ. Res. 92:595-597
68. Kukreja, et al., (2003) Cardiovasc Res. 60:700-701
69. Feenstra, et al., (1998) Lancet 352:957-958
70. Thadani, et al., (2002) J Am Coll Cardiol. 40:2006-2012
71. Cremers, et al., (2003) J Cardiovasc Pharmacol. 41:734-743
72. Massion, et al., (2003) Circ Res. 93:388-398
73. Rivet-Bastide, et al., (1997) J Clim Invest. 99:2710-2718
74. Hare, et al., (1995) Circulation. 92:2198-2203
75. Massion, et al., (2003) J Physiol 546:63-75
76. Sharir, et al., (1994) Circulation 89:2045-2053
77. Nakayama, et al., (1998) Am Heart J. 136:281-288
78. Fleg, et al., (1994) Circulation 90:2333-2341
79. Feil, et al., (2003) Circ Res. 93:907-916
80. Goldstein, et al., (1998) N Engl. J. Med. 338:1397-1404
81. Pilz, et al., (2003) Circ. Res. 93:1034-1046
82. Pfizer Labs, Product Information: Viagra®, Sildenafil Citrate (2002)
83. Lewis, et al., (1984) Circulation 70:425-431
84. Marrnor, et al., (1997) J Am Coll Cardiol. 29:422-428
85. Phillips, et al., (2000) Circulation. 102:3068-3073
86. Daly, et al., (1997) Am J. Cardiol. 79:1381-1386
87. Piccirillo, et al. (2002) Am Heart J. 143:703-710
88. Schalcher, et al. (2002) Hypertension 40:763-767
89. Sohn, et al., (1997) J Am Coll Cardiol. 30:474-480
90. Ommen, et al., (2000) Circulation. 102:1788-1794
91. Traverse, et al., (2000) Circulation 102:2997-3002

---

The invention claimed is:

1. A method of enhancing cardiac function in a subject having left ventricular hypertrophy, the method comprising administering to the subject an effective amount of a PDE5 inhibitor, wherein the administration of the inhibitor enhances cardiac function.

2. The method of claim 1, wherein the method reduces or reverses cardiac chamber remodeling.

3. The method of claim 2, wherein the method reduces or reverses cardiac dilation.

4. The method of claim 1, wherein the method reduces or reverses cardiac muscle cell remodeling.

5. The method of claim 4, wherein the method reduces myocyte hypertrophy.

6. The method of claim 1, wherein the method reduces or reverses molecular remodeling.

7. The method of claim 6, wherein the PDE5 inhibitor reduces expression of an agent selected from the group consisting of metalloproteinases, calcineurin, mitogen activated kinase, Akt kinase, nuclear factor of activated T-cells (NFAT), RhoA and Rho kinase, PI3 kinase, components of a gp130/Stat-3 pathway, nitrotyrosine, nitric oxide synthase, an agent associated with nitric oxide synthase uncoupling, and an agent associated with oxidative stress.

8. The method of claim 6, wherein the PDE5 inhibitor reduces the biological activity of an agent selected from the group consisting of metalloproteinases, calcineurin, mitogen activated kinase, Akt kinase, NFAT, Rho A and Rho kinase, PI3 kinase, components of the gp130/Stat-3 pathway, nitrotyrosine, nitric oxide synthase, an agent associated with nitric oxide synthase uncoupling and an agent associated with oxidative stress.

9. The method of claim 1, wherein the PDE5 inhibitor enhances cGMP-dependent signaling via Protein Kinase G.

10. The method of claim 1, wherein the cardiac chamber, cellular or molecular remodeling is induced by a stimulus.

11. A method of reducing left ventricular hypertrophy in a subject having left ventricular hypertrophy, the method comprising administering to the subject an effective amount of a PDE5 inhibitor, wherein the administration of the inhibitor reduces cardiac hypertrophy.

12. The method of claim 11, wherein the method reverses cardiac hypertrophy.

13. A method of reversing left ventricular cardiac hypertrophy in a subject, the method comprising administering to a subject identified as having left ventricular cardiac hypertrophy an effective amount of a PDE5 inhibitor, wherein the administration of the inhibitor reverses left ventricular cardiac hypertrophy.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tgagcagttc ctggaagcct        20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
atgtcaccat ctgcttggcc        20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
accatcttcc aggagcgaga c        21

<210> SEQ ID NO 4
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gccttctcca tggtggtgaa                                              20
```